(12) United States Patent
Hamilton et al.

(10) Patent No.: US 11,780,915 B2
(45) Date of Patent: Oct. 10, 2023

(54) BINDING PROTEINS TO THE HUMAN THROMBIN RECEPTOR, PAR4

(71) Applicant: Monash University, Clayton (AU)

(72) Inventors: Justin Hamilton, Clayton (AU); Mark Sleeman, Clayton (AU)

(73) Assignee: MONASH UNIVERSITY, Clayton (AU)

( * ) Notice: Subject to any disclaimer, the term of this patent is extended or adjusted under 35 U.S.C. 154(b) by 27 days.

(21) Appl. No.: 16/646,554

(22) PCT Filed: Sep. 11, 2018

(86) PCT No.: PCT/AU2018/050985
§ 371 (c)(1),
(2) Date: Mar. 11, 2020

(87) PCT Pub. No.: WO2019/046912
PCT Pub. Date: Mar. 14, 2019

(65) Prior Publication Data
US 2021/0179707 A1   Jun. 17, 2021

(30) Foreign Application Priority Data
Sep. 11, 2017   (AU) ................................ 2017903685

(51) Int. Cl.
*C07K 16/28* (2006.01)
*A61K 47/68* (2017.01)
*A61P 7/02* (2006.01)

(52) U.S. Cl.
CPC .......... *C07K 16/28* (2013.01); *A61K 47/6849* (2017.08); *A61P 7/02* (2018.01); *C07K 2317/34* (2013.01); *C07K 2317/524* (2013.01); *C07K 2317/526* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS 6,180,370 B1 * 1/2001 Queen ..................... A61P 31/12
435/69.6

FOREIGN PATENT DOCUMENTS

| WO | 1999043809 A2 | 9/1999 | |
|---|---|---|---|
| WO | 2001007072 A1 | 2/2001 | |
| WO | WO-0107072 A1 * | 2/2001 | ............. A61K 38/08 |
| WO | WO2001007072 A1 * | 2/2001 | ............. A61K 38/08 |

OTHER PUBLICATIONS

Monnier, Philippe P., Robin J. Vigouroux, and Nardos G. Tassew Antibodies 2.2 (2013): 193-208 (Year: 2013).*
Stryer, Biochemistry 4th, WH Freeman, New York. 1995 (Year: 1995).*
Colman, Research in Immunology 145.1 (1994): 33-36 (Year: 1994).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
French, et al., "Inhibition of protease-activated receptor 4 impairs platelet procoagulant activity during thrombus formaiton in human blood", J Thromb Haemost., 14(8): 1642-54, Aug. 2016.
French, S.L., et al., "A function-blocking PAR4 antibody is markedly antithrombotic in the face of a hyper-reactive PAR4variant", Blood Adv., 2(11):1283-1293, Jun. 12, 2018.
International Search Report and Written Opinion dated Nov. 22, 2018 for PCT application No. PCT/AU2018/050985.
Lee, H., et al., "PAR4 mediates thrombin-induced pro-coagulant activity in human platelets", Journal of Thrombosis and Haemostasis, (Jul. 2011) vol. 9, Supp. Suppl. 2, pp. 70. Abstract No. P-MO-038. Meeting Info: 23rd Congress of the International Society on Thrombosis and Haemostasis 57th Annual SSC Meeting. Kyoto, Japan, Jul. 23, 2011-Jul. 28, 2011. ISSN: 1538-7933.
Mumaw, M.M., et al., "Development and characterization of monoclonal antibodies against Protease Activated Receptor 4 (PAR4)", Throm Res. 135(6): 1165-71, Jun. 2015.
Sambrano GR., et al., "Cathepsin G activates protease-activated receptor-4 in human platelets", J Biol Chem., 275(10): 6819-23, Mar. 10, 2000.
Sangawa, T., et al., "A murine monoclonal antibody that binds N-terminal extracellular segment of human protease-activated receptor-4", Hybridoma (Larchmt), 27(5): 331-5, Oct. 2008.

* cited by examiner

Primary Examiner — Michael Szperka
Assistant Examiner — Lia E Taylor
(74) Attorney, Agent, or Firm — Storella & Witt, LLP

(57) ABSTRACT

The present disclosure is directed to human protease activated receptor 4 (PAR4) binding proteins (e.g. antibodies). In particular, anti-PAR4 binding proteins which are antagonists of human PAR4, as well as methods and uses thereof.

20 Claims, 26 Drawing Sheets
Specification includes a Sequence Listing.

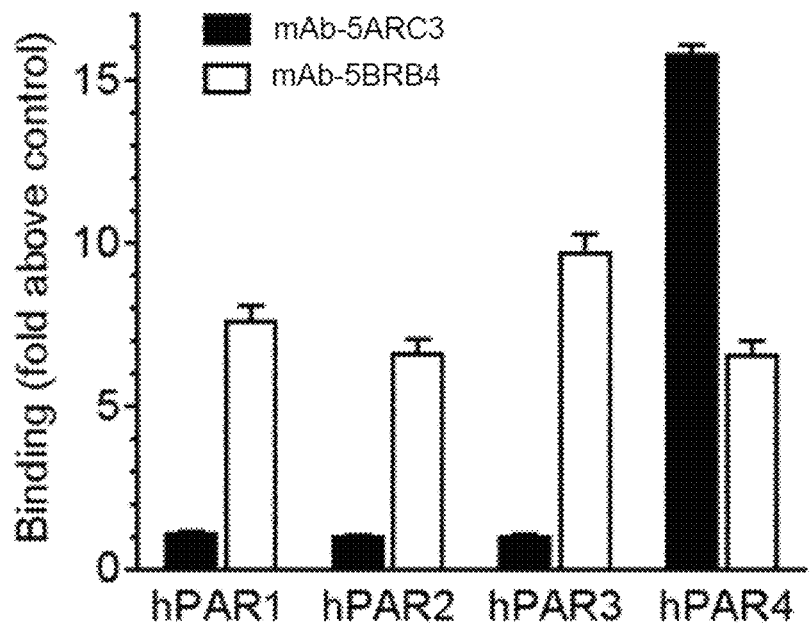
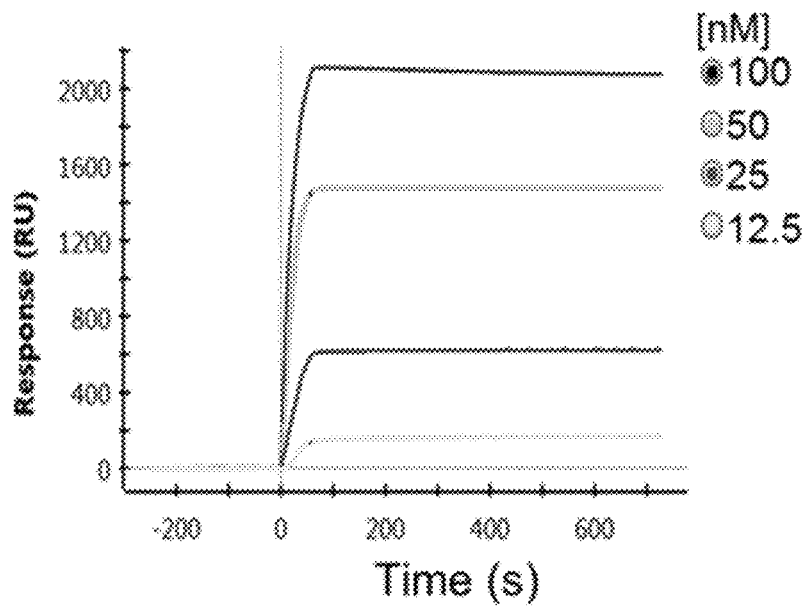
FIGURE 5

A.

| FWR1 | CDR1 (SEQ ID NO: 13) |

QVQLVESGGGVVQPGRSLRLSCAASGFTLSNYGMHWV

| FWR2 | CDR2 (SEQ ID NO: 14) | FWR3 |

RQAPGKGLEWVSVIWYDGSNKHYADSVKGRFTISRDN

CDR3 (SEQ ID NO: 15)

SKNTLYLQMNSLRAEDTAVYYCARESIVEVLPPFDYW

GQGTLVTVSS (SEQ ID NO: 11)

B.

| FWR1 | CDR1 (SEQ ID NO: 16) |

KIVLTQSPGTLSLSPGERVTLSCRASQRVRNNYLAW

| FWR2 | CDR2 (SEQ ID NO: 17) | FWR3 |

FQQKPGQAPRLFIYGASSRATGIPDRFSGSGSGTDF

CDR3 (SEQ ID NO: 18)

IFTISRLEPEDFAVYYCQQYGNSYTFGQGTKLEIK (SEQ ID NO: 12)

Antibody Cell-line Name: Mo85A.RC3.H4b

```
            FWR1                              CDR1 (SEQ ID NO: 34)
EVQLVESGGDLVKPGGSLRLSCSAS GFTFFNTW MNWV
        FWR2           CDR2 (SEQ ID NO: 35) FWR3
RQAPGKGLEWVGR VKSKNDGGTK DYAAPVTGRFTISR
                                        CDR3 (SEQ ID NO: 36)
DDSKDTLYLQMNSLKTEDTAVYYC TTDPHYDFWSAY W

GQGTLVTVSS (SEQ ID NO: 32)
```

B.

```
            FWR1                              CDR1 (SEQ ID NO: 37)
DIVMTQTPLSSPVTLGQPASISCRSS QSLVHSDGNT
        FWR2           CDR2 (SEQ ID NO: 38) FWR3
Y LSWLQQRPGQPPRLLIY KIS NRFSGVPDRFSGSGA
                                        CDR3 (SEQ ID NO: 39)
GTDFTLKISRVEAEDVGFYYC LQATQFMYT FGQGTK

LEIK (SEQ ID NO: 33)
```

Antibody Cell-line Name: Mo85H RD2.B10.A7b

FWR1　　　　　　　　　　　　　　　　　　CDR1 (SEQ ID NO: 24)

QVQLVQSGAEVKKPGASVKVSCKTSAYTFTNYGISWV

FWR2　　　　　　CDR2 (SEQ ID NO: 25)　　FWR3

RQAPGQGLEWMGWISPYNGNTNYAQKLQGRVTMTTDT

CDR3 (SEQ ID NO: 26)

STRTAYMELRSLRSDDTAVYYCAREYNRSSRGRYYYY

GMDVWGQGTTVTVSS (SEQ ID NO: 22)

B.

FWR1　　　　　　　　　　　　　　　　　　CDR1 (SEQ ID NO: 27)

EIVLTQSPGTLSLSPGERATLSCRASQSVSSNYLAW

FWR2　　　　　CDR2 (SEQ ID NO: 27) FWR3

YQKKPGQAPRLLISGASSRATGIPDRFSGSGSGTDF

CDR3 (SEQ ID NO: 29)

TLTISRLEPEDFAVYYCQQYGSSPWTFGQGTKVEIK (SEQ ID NO: 23)

Antibody Cell-line Name:　　MoB5F RF3.A7b.A1

```
G D D S T P S I L P A P R G Y P G Q V C    hPAR4 peptide  (SEQ ID NO:4)
G D D S T P S I L                          hPAR4 1-9      (SEQ ID NO:119)
        I L P A P R G Y                    hPAR4 8-15     (SEQ ID NO:120)
              A P R G Y P G Q V C          hPAR4 11-20    (SEQ ID NO:121)
```

FIGURE 22

BINDING PROTEINS TO THE HUMAN THROMBIN RECEPTOR, PAR4

INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

The present application claims priority from Australian Patent Application 2017903685 filed 11 Sep. 2017, the entire contents of which are herein incorporated by reference.

REFERENCE TO SEQUENCE LISTING

The instant application contains a Sequence Listing which has been submitted electronically in ASCII format and is hereby incorporated by reference in its entirety. Said ASCII copy, created on Dec. 29, 2021, is named 525571US_Updated sequence listing.txt and is 66,279 bytes in size.

FIELD OF THE DISCLOSURE

The present disclosure is directed to human protease activated receptor 4 (PAR4) binding proteins (e.g. antibodies). In particular, anti-PAR4 binding proteins which are antagonists of human PAR4, as well as methods and uses thereof.

BACKGROUND OF THE DISCLOSURE

Activated platelets are the key cellular components of arterial thrombosis, the most common cause of death and disability in the world (Rosendaal F R et al. (2014) 384: 1653-4), accounting for almost 40% of deaths in many countries (Mozaffarian D et al. (2015) Circulation 131 e29-322), including Australia (Australian Bureau of Statistics, Causes of Death, Australia, 2011 3303 Chapter 42011 (2013)). Arterial thrombosis causes heart attacks and ischaemic strokes.

Platelets are the cells that form arterial thrombi. Platelets are activated by a combination of endogenous agonists that trigger platelet aggregation and the promotion of coagulation, which together facilitate pathologic thrombus formation. Anti-platelet drugs therefore constitute the main pharmacotherapy for the prevention of arterial thrombosis. However, despite an array of such agents, limitations in safety and/or efficacy necessitate the rationalisation of new drug targets. There is a major need for improved anti-platelet drugs in a wide range of clinical settings and there is much interest in the development of new agents.

Thrombin is the most potent known activator of human platelets and is also the key effector protease of the coagulation cascade. Thrombin activates platelets predominantly via protease activated cell-surface receptors (PARs), PAR1 and PAR4, to be the body's most potent platelet activator (Vu T-K H et al (1991) Cell 64:1057-68; Coughlin S R (1992) J Clin Invest 89:351-5; Coughlin S R (2000) Nature 407:258-64). The receptors belong to a unique family of seven transmembrane receptors, G-protein Coupled Receptors (GPCRs) that are activated by proteolysis of their N-terminus. Once cleaved, the newly exposed N-terminus serves as a tethered ligand that activates the receptor by binding extracellular loop 2 (Vu T-K H et al (1991) Cell 64:1057-68). There are 4 members of the PAR family (PAR1-4) which are widely expressed and activated by multiple proteases.

Mice lacking all platelet PAR function (PAR4$^{-/-}$) are protected against thrombosis without showing spontaneous bleeding (Hamilton J et al. (2004) Thromb Haemost 2:1429-35; Hamilton J et al. (2009) Blood Rev 23:61-5), indicating the potential of targeting these receptors for antithrombotic therapy. There are two predominant PARs on human platelets, PAR1 and PAR4. Of these, PAR1 is the higher-affinity thrombin receptor and has been the focus of anti-platelet drug development with two PAR1 antagonists, atopaxar (E5555) (Goto S et al. (2010) Eur Heart J 31:2601-13) and vorapaxar (Tricoci P et al. (2012) New Engl J Med 366:20-33; Morrow D A et al (2012) New Engl J Med 366:1404-13) having been evaluated in clinical trials. Vorapaxar was approved by the US FDA in late 2014 and scheduled by the TGA in mid-2016 for the prevention of myocardial infarction and peripheral artery disease. However, vorapaxar in combination with single or dual antiplatelet therapy was associated with significantly increased rates of intracranial bleeding, particularly in patients with a history of stroke or other predisposing factors (Tricoci P et al. (2012) New Engl J Med 366:20-33; Morrow D A et al (2012) New Engl J Med 366:1404-13).

Consequently, the development of PAR4 antagonists has become of great interest. The functional roles of PAR4 have primarily been elucidated on platelets. A key feature that distinguishes PAR4 is its ability to form hetero-oligomers with both PAR1 and the ADP receptors P2Y12 which allows PAR4 to influence both thrombin and ADP initiated signalling (Li D et al. (2011) J Biol Chem 286:3805-14). One major distinction between the two platelet PARs relates to the kinetics of intracellular signalling (Holinstat M et al. (2006) J Biol Chem 281:26665-74; Voss B et al. (2007) Mol Pharmacol 71:1399-406; Holinstat M et al. (2007) Mol Pharmacol 71:686-94). Both PAR1 and PAR4 signal via Gq to mobilise intracellular calcium and drive platelet functions, including integrin activation, granule secretion and phosphatidylserine (PS) exposure. However PAR4 activation induces a slower and more sustained intracellular calcium signal than PAR1 activation (Covic L et al. (2002) PNAS 99:643-8). This temporal difference in calcium signalling may be attributable in part to an anionic sequence C-terminal to the PAR4 cleavage site (Jacques S et al. (2003) Biochem J 376:733-40). The cellular consequences of such sustained platelet activation downstream of PAR4 have not yet been completely characterised, but may involve sustained platelet secretion kinetics (Jonnalagadda D et al. (2012) 120:5209-16) and platelet procoagulant function, given the reliance of these phenomena on sustained, elevated, intracellular calcium levels (Williamson P et al. (1995) 34:10448-55; Dachary-Prigent J et al. (1995) Biochemistry 34:11625-34).

There have been no studies examining the contribution of PAR4 to pro-coagulant activity in the setting of human thrombus formation, likely due to the limited availability of appropriate PAR4 antagonists required for such studies. The most commonly used PAR4 antagonists are the small molecule YD-3 (Wu C C et al. (2000) Br J Pharmacol 130: 1289-96), the peptidomimetic tc-YPGKF-NH$_2$ (Hollenberg M D et al. (2001) 79:439-42), and the pepducins P4pal-10 and P4pal-il (Leger A J et al. (2006) Circulation 113:1244-54; Covic L et. al.. (2002) PNAS 99:643-8; Stampfuss J J et al. (2003) Nat Med 9:1447). However, these agents are either not widely available (e.g. YD-3) or have been reported to lack specificity (e.g. pepducins) and/or efficacy (e.g.

tc-YPGKF-NH$_2$) in studies using human platelets (Stampfuss J J et al. (2003) Nat Med 9:1447; Hollenberg M D et al. (2004) Br J Pharmacol 143:443-54; Wu C C et al. (2002) Thromb Haemost 87:1026-33). A PAR4 antagonist (BMS-986141) in early clinical trials is being examined for treatment of thrombosis, however a common PAR4 variant (present in 19-82% of people, depending on the population) renders the receptor insensitive to small molecule inhibitors such as BMS-986141.

Based on the foregoing, it will be apparent to the skilled artisan that the identification of improved human PAR4 binding proteins for medical treatment of thrombosis would be useful. Furthermore, the treatment of thrombosis, with minimal adverse side effects is a significant unmet medical need. Thus, there is a need in the art for PAR4 antagonists that provide advantages over existing strategies and which provide an improved therapeutic profile over targeting PAR1 in the treatment or prevention of thrombosis.

SUMMARY OF DISCLOSURE

Current clinical programs are developing small molecule orthosteric PAR4 inhibitors. However, it was recently revealed that this approach is completely ineffective in a large percentage of patients. Specifically, a single nucleotide polymorphism (SNP; rs773902) in PAR4 renders the receptor insensitive to orthosteric PAR4 antagonism (Edelstein L C et al (2014) Blood 124:3450-3458). This small nucleotide polymorphism (SNP) determines whether amino acid 120 is an alanine (Ala120) or a threonine (Thr120). Pharmacological studies have shown that orthosteric PAR4 antagonism potently inhibits PAR4-induced platelet activation in patients genotyped as Ala120 but is entirely without effect on platelets from patients genotyped as Thr120 even at high concentration. Heterozygosity results in partial inhibition only (Edelstein L C et al (2014) Blood 124:3450-3458). The frequency of inhibitor-resistant Thr120 form of PAR4 is remarkably high (>80% in some populations), indicating the impact of this antagonism insensitivity is significant. The Thr120 allele is racially dimorphic, occurring in 63% of self-identified blacks in a cohort of 154 North Americans compared with 19% of whites. Data from the Human Genome Diversity Project (HGDP) shows SNP rs773902 is not region-specific, with up to 80% of people in sub-Saharan Africa and about two-thirds of Papuans and Melanesians having Thr120 PAR4 variant.

In addition to rendering PAR4 resistant to orthosteric inhibitors, SNP rs773902 also increases the sensitivity of PAR4 to receptor activation, resulting in hyper-active platelets in patients with the Thr120 variant (Edelstein L C et al. (2013) Nat Med 19:1609-1616). This increased PAR4 function persisted in patients treated with standard-of-care anti-platelet drugs (aspirin and/or a P2Y12 inhibitor).

The present inventors have developed monoclonal antibodies which bind specifically to human PAR4 and inhibit PAR4 activation by thrombin. Accordingly, these antibodies are antagonists of PAR4 cleavage induced by thrombin. The antibodies identified by the inventors are capable of antagonising or reducing a PAR4-mediated event (e.g. thrombosis). Furthermore, the inventors have found that targeting PAR4 is less likely to invoke bleeding complications compared to targeting PAR1 (a common target of prior art antibodies) due to its distinct mechanism of action and overall broader safety profile.

In particular, the antibodies identified by the inventors are effective against both PAR4 receptor variants, namely Ala120 and Thr120 which means they are effective for treatment of thromboembolic disorders in all subjects, not merely those with the sensitive PAR4 variant. Additionally, because the antibodies bind specifically to PAR4 with minimal cross-reactivity to PAR1, bleeding complications can be minimised or avoided. Accordingly, the present antibodies are thus distinguished from the PAR1 antagonists and PAR4 small molecule inhibitors of the prior art.

Additionally, the inventors found that the antibodies markedly inhibit thrombin-induced PAR4 cleavage and aggregation of human platelets. Moreover, these effects could be reversed by competing off the antibody with the immunising peptide.

Thus, the present disclosure provides various reagents for diagnosing or prognosing thrombosis in a subject. The present disclosure also provides methods for treating, preventing or ameliorating thrombosis or a thromboembolic disorder in a subject.

The present disclosure provides a PAR4-binding protein comprising an antigen-binding domain, wherein the antigen-binding domain binds specifically to human PAR4 and wherein the protein antagonises at least one PAR4-mediated event (e.g. thrombosis). In one example, the protein antagonises at least one PAR4-mediated event (e.g. thrombosis) in the presence of thrombin.

In one example, the antigen binding domain is from, or derived from, a non-antibody PAR4 binding protein. In one example, the PAR4-binding protein is not a small molecule antagonist e.g. imidazothiadiazole derivatives for example as described in WO2013/163244 or synthetic peptide analogs for example as described in U.S. Pat. No. 7,879,792.

The present disclosure also provides a human PAR4 binding protein comprising an antigen-binding domain of an anti-PAR4 antibody, wherein the antigen binding domain binds specifically to PAR4 and wherein the protein antagonizes at least one PAR4-mediated event (e.g. thrombosis) when contacted to a cell expressing PAR4. In one example, the protein antagonises at least one PAR4-mediated event (e.g. thrombosis) in the presence of thrombin.

In one example, the PAR4-binding protein inhibits externalisation of phosphatidylserine (PS) on the cell surface of a cell expressing PAR4 (e.g. platelets). In one example, the PAR4-binding protein reduces thrombus volume when measured by a whole blood thrombosis assay.

The present disclosure provides a protease activated receptor 4 (PAR4) binding protein which is an anti-PAR4 recombinant or synthetic or monoclonal antibody or antigen-binding fragment thereof, wherein the PAR4-binding protein substantially inhibits human PAR4 cleavage induced by thrombin.

Persons skilled in the art will be able to measure PAR4 cleavage using appropriate in vitro assays. By way of non-limiting example, PAR4 cleavage can be assessed in a cell line expressing a fluorescently labelled tagged PAR4 protein on its surface. Cleavage of PAR4 in the presence of thrombin causes loss of FLAG from the cell surface which can be quantified. In a particular example, PAR4 cleavage can be determined in transfected HEK293 cells comprising nucleic acid encoding PAR4 containing a fluorescently labelled FLAG tag. Cleavage of PAR4 in the presence of thrombin (e.g. 0.1 U/ml) causes loss of FLAG from the cell surface which can be quantified by the use of flow cytometry.

In one example, the binding protein inhibits cleavage of cell surface expressed human PAR4 by equal to or greater than 50% in the presence of thrombin.

In one example, the PAR4 binding protein specifically binds to an epitope which spans the thrombin cleavage site of human PAR4. In one example, the PAR4-binding protein binds specifically to an epitope comprising residues contained within the sequence set forth as GDDSTPSILPAPR-GYPGQVC (SEQ ID NO:2). In one example, the peptide consists of SEQ ID NO:1 or SEQ ID NO:2. For example, the peptide is displayed on the surface of a phage.

In another example, the epitope comprises the sequence APRGY (SEQ ID NO:42), wherein the thrombin cleavage site corresponds to RG. In another example, the epitope comprises or consists of a sequence selected from ILPA-PRGY (SEQ ID NO: 43) or APRGYPGQV (SEQ ID NO:44). In another example, the PAR4-binding protein binds specifically to an epitope comprising the sequence set forth as PRGYPG (SEQ ID NO:1).

In one example, the PAR4-binding protein specifically binds to either the Ala120 or the Thr120 variant of human PAR4. In another example, the PAR4-binding protein binds to both the Ala120 and the Thr120 variant of human PAR4.

In one example, the PAR4-binding protein binds to a thrombin-cleavage site in the human PAR4 sequence according to SEQ ID NO:19. In one example, the PAR4-binding protein binds to a sequence matching residues 35-54 of the human PAR4 sequence set forth in SEQ ID NO:19. In another example, the PAR4-binding protein binds to the sequence set forth as SEQ ID NO:2 optionally additionally comprising a keyhole limpet hemocyanin (KLH) or other immune-stimulating molecule. In a further example, the PAR4-binding protein binds to the sequence set forth in SEQ ID NO:4.

In another example, the PAR4-binding protein binds to the sequence set forth as SEQ ID NO:2, optionally additionally comprising a C-terminal GGGG and streptavidin-k/biotin (SKB). In one example, the PAR4 protein binds to the sequence set forth as SEQ ID NO:7.

In one example, the PAR4-binding protein does not bind, or does not substantially bind to, human PAR3, PAR2 or PAR1.

In a further example, the PAR4-binding protein does not bind, or does not substantially bind to a PAR sequence selected from the group consisting of SEQ ID NO:3 (mouse PAR4), SEQ ID NO:8 (human PAR3), SEQ ID NO:9 (human PAR2) or SEQ ID NO:10 (human PAR1).

In one example, the level of binding is assessed by immobilizing the peptide (e.g. a peptide according to SEQ ID NO:2 or SEQ ID NO:7) and contacting the peptide with the PAR4-binding protein.

Exemplary PAR4-binding proteins described herein having such binding characteristics comprise the variable regions and/or CDRs of an antibody designated 5ARC3.F10b.H4b (hereinafter referred to as 5A.RC3) or 5F.RF3.A7b.A1 (hereinafter referred to as 5F.RF3).

In one example, the PAR4-binding protein binds to a peptide consisting of the sequence set forth in SEQ ID NO:1, SEQ ID NO:2, SEQ ID NO:4, or SEQ ID NO:7 or to human PAR4 at a similar or substantially the same level, or with a similar or substantially the same affinity as the antibody designated 5A.RC3, 5I.RG1, 5F.RG3, 5G.RA1, 5D.RH4, 5H.RH4, 5G.RF6, 5G.RD6, 5H.RA3, 5G.RG1, 5H.RG4, 5G.RC5, 5F.RE6, 5H.RF2.

In another example, the PAR4-binding protein competitively inhibits binding of the antibody designated 5A.RC3, 5I.RG1, 5F.RG3, 5G.RA1, 5D.RH4, 5H.RH4, 5G.RF6, 5G.RD6, 5H.RA3, 5G.RG1, 5H.RG4, 5G.RC5, 5F.RE6, 5H.RF2 to human PAR4. In a further example, the protein competitively inhibits binding of the antibody designated 5A.RC3, 5I.RG1, 5F.RG3, 5G.RA1, 5D.RH4, 5H.RH4, 5G.RF6, 5G.RD6, 5H.RA3, 5G.RG1, 5H.RG4, 5G.RC5, 5F.RE6, 5H.RF2 to a peptide consisting of the sequence set forth in SEQ ID NO:2, SEQ ID NO:4, or SEQ ID NO:7.

In one example, the PAR4-binding protein binds to a peptide consisting of a sequence set forth in SEQ ID NO:2, SEQ ID NO:4, or SEQ ID NO:7 in an amount within 75% of the amount of bound by an antibody comprising a VH comprising a sequence set forth in SEQ ID NO:11, SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107 and a VL comprising a sequence set forth in SEQ ID NO:12,SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108.

In one example, the amount of protein or antibody bound is assessed by contacting the PAR4-binding protein to a peptide consisting of the sequence set forth in SEQ ID NO:2, SEQ ID NO:4, or SEQ ID NO:7 and an amount of the PAR4-binding protein (e.g. 10 μg/ml) brought into contact with the peptide. The amount of PAR4-binding protein bound to the peptide is then determined and compared to the amount of an antibody comprising a VH comprising a sequence set forth in SEQ ID NO:11, SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107 and a VL comprising a sequence set forth in SEQ ID NO:12, SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108 respectively bound to the peptide. In one example, the amount of PAR4-binding protein bound to the peptide is within about 80%, or 70% or 60% or 40% of the amount of antibody bound.

The present disclosure also provides a PAR4-binding protein which competitively inhibits binding of an antibody designated:

(i) 5A.RC3 said antibody comprising a VH comprising a sequence set forth in SEQ ID NO:11 and a VL comprising a sequence set forth in SEQ ID NO:12;

(ii) 5I.RG1 comprising a VH comprising a sequence set forth in SEQ ID NO:45 and a VL comprising a sequence set forth in SEQ ID NO:46;

(iii) 5F.RF3 comprising a VH comprising a sequence set forth in SEQ ID NO:22 and a VL comprising a sequence set forth in SEQ ID NO:23;

(iv) 5G.RA1 comprising a VH comprising a sequence set forth in SEQ ID NO:53 and a VL comprising a sequence set forth in SEQ ID NO:54;

(v) 5D.RH4 comprising a VH comprising a sequence set forth in SEQ ID NO:89 and a VL comprising a sequence set forth in SEQ ID NO:90;

(vi) 5H.RH4 comprising a VH comprising a sequence set forth in SEQ ID NO:91 and a VL comprising a sequence set forth in SEQ ID NO:92;

(vii) 5G.RF6 comprising a VH comprising a sequence set forth in SEQ ID NO:93 and a VL comprising a sequence set forth in SEQ ID NO:94;

(viii) 5G.RD6 comprising a VH comprising a sequence set forth in SEQ ID NO:95 and a VL comprising a sequence set forth in SEQ ID NO:96;

(ix) 5H.RA3 comprising a VH comprising a sequence set forth in SEQ ID NO:97 and a VL comprising a sequence set forth in SEQ ID NO:98;

(x) 5G.RG1 comprising a VH comprising a sequence set forth in SEQ ID NO:99 and a VL comprising a sequence set forth in SEQ ID NO:100;

(xi) 5H.RG4 comprising a VH comprising a sequence set forth in SEQ ID NO:103 and a VL comprising a sequence set forth in SEQ ID NO:104;

(xii) 5G.RC5 comprising a VH comprising a sequence set forth in SEQ ID NO:103 and a VL comprising a sequence set forth in SEQ ID NO:104;

(xiii) 5F.RE6 comprising a VH comprising a sequence set forth in SEQ ID NO:105 and a VL comprising a sequence set forth in SEQ ID NO:106; or (xiv) 5H.RF2 comprising a VH comprising a sequence set forth in SEQ ID NO:107 and a VL comprising a sequence set forth in SEQ ID NO:108 to a peptide comprising, or consisting of the sequence set forth in SEQ ID NO:2, SEQ ID NO:4, or SEQ ID NO:7 or to human PAR4 (e,g. SEQ ID NO:19).

In one example, the PAR4-binding protein reduces thrombin-induced cleavage of human PAR4 (i.e. has PAR4 antagonist activity) expressed on a cell surface (e.g. HEK293 cells transfected with PAR4 containing an N-terminal FLAG tag). In one example, the PAR4-binding protein (e.g. at a concentration of 10 μg/ml) reduces thrombin-induced cleavage (e.g. at 0.1 U/ml) of PAR4 expressing HEK293 cells (e.g. about $5 \times 10^4$ cells). An exemplary antibody having such activity comprises the variable regions or complementary determining regions (CDRs) of antibody 5A.RC3, 5I.RG1, 5F.RF3, 5G.RA1, 5D.RH4, 5H.RH4, 5G.RF6, 5G.RD6, 5H.RA3, 5G.RG1, 5H.RG4, 5G.RC5, 5F.RE6, or 5H.RF2 or an antibody comprising the CDRs thereof.

In one example, the PAR4-binding protein binds to a peptide comprising the thrombin cleavage site of human PAR4 as described herein, or to an N-terminal extracellular region of human PAR4 with an affinity dissociation constant (KD) of 2 nM or less, such as, 1.5 nM or less, for example, 1 nM or less. In one example, the KD is between about 0.01 nM to about 2 nM, such as between about 0.05 nM to about 1 nM, for example, between about 0.1 nM to about 1 nM, for example, between about 0.3 nM to about 1 nM. In one example, the KD is between about 0.01 nM and 1 nM, such as between about 0.05 nM and 0.9 nM, for example, between about 0.09 nM and 0.7 nM, for example, between about 0.1 nM and 0.6 nM.

In one example, the KD is assessed by utilising a streptavidin chip and capturing the biotin-coupled human PAR4 peptide (e.g. peptide according to SEQ ID NO:7) on the surface of the chip and passing the PAR4-binding protein thereover.

In one example, the KD is assessed by utilising a streptavidin chip and capturing the biotin-coupled human PAR4 peptide (e.g. peptide according to SEQ ID NO:7) on the surface of the chip and passing the PAR4-binding protein thereover.

An exemplary PAR4-binding protein of the disclosure has a KD of between about 0.01 and 0.61 when assessed by SA chip biotin peptide SPR. In one example, the PAR4 binding protein has a KD of about 0.4 nM (e.g. +/−0.1 nM). In one example, the PAR4 binding protein has a KD as shown in Table 4 corresponding to any one of the PAR4 binding proteins therein.

In one example, a PAR4-binding protein of the disclosure binds specifically to human PAR4. In one example, the binding of the protein is assessed by ELISA and high-throughput antigen microarray.

In one example, the PAR4-binding protein binds to the same epitope in human PAR4 or to an epitope in human PAR4 that overlaps with the epitope bound by antibody:

(i) 5A.RC3 said antibody comprising a VH comprising a sequence set forth in SEQ ID NO:11 and a VL comprising a sequence set forth in SEQ ID NO:12;

(ii) 5I.RG1 comprising a VH comprising a sequence set forth in SEQ ID NO:45 and a VL comprising a sequence set forth in SEQ ID NO:46;

(iii) 5F.RF3 comprising a VH comprising a sequence set forth in SEQ ID NO:22 and a VL comprising a sequence set forth in SEQ ID NO:23;

(iv) 5G.RA1 comprising a VH comprising a sequence set forth in SEQ ID NO:53 and a VL comprising a sequence set forth in SEQ ID NO:54;

(v) 5D.RH4 comprising a VH comprising a sequence set forth in SEQ ID NO:89 and a VL comprising a sequence set forth in SEQ ID NO:90;

(vi) 5H.RH4 comprising a VH comprising a sequence set forth in SEQ ID NO:91 and a VL comprising a sequence set forth in SEQ ID NO:92;

(vii) 5G.RF6 comprising a VH comprising a sequence set forth in SEQ ID NO:93 and a VL comprising a sequence set forth in SEQ ID NO:94;

(viii) 5G.RD6 comprising a VH comprising a sequence set forth in SEQ ID NO:95 and a VL comprising a sequence set forth in SEQ ID NO:96;

(ix) 5H.RA3 comprising a VH comprising a sequence set forth in SEQ ID NO:97 and a VL comprising a sequence set forth in SEQ ID NO:98;

(x) 5G.RG1 comprising a VH comprising a sequence set forth in SEQ ID NO:99 and a VL comprising a sequence set forth in SEQ ID NO:100;

(xi) 5H.RG4 comprising a VH comprising a sequence set forth in SEQ ID NO:103 and a VL comprising a sequence set forth in SEQ ID NO:104;

(xii) 5G.RC5 comprising a VH comprising a sequence set forth in SEQ ID NO:103 and a VL comprising a sequence set forth in SEQ ID NO:104;

(xiii) 5F.RE6 comprising a VH comprising a sequence set forth in SEQ ID NO:105 and a VL comprising a sequence set forth in SEQ ID NO:106; or (xiv) 5H.RF2 comprising a VH comprising a sequence set forth in SEQ ID NO:107.

The present disclosure also provides a PAR4 binding protein which specifically binds to human PAR4 and which is an anti-PAR4 recombinant or synthetic or monoclonal antibody or antigen-binding fragment thereof.

In one example, the antibody substantially inhibits cleavage of PAR4 by thrombin.

In one example, the PAR4 is expressed on human platelets.

In one example, the PAR4-binding protein is a chimeric antibody comprising human heavy and light chain constant region sequences. In another example, the PAR4-binding protein is a humanised or fully human antibody.

In one example, the PAR4-binding protein inhibits cleavage of cell surface expressed PAR4 by equal to or greater than 60% in the presence of thrombin or a PAR1 antagonist. In further examples, the protein inhibits cleavage of PAR4 by at least 50%, at least 55%, at least 60%, at least 65%, at least 70%, at least 75%, at least 8%, at least 85%, at least 87%, at least 90%, at least 92%, at least 94%, at least 95%, at least 97% or 100%.

In another example, cleavage of PAR4 by thrombin is measured by loss of Flag tag from flag-tagged PAR4 expressing HEK293 cells. In another example, cleavage is measured by flow cytometry.

In one example, the PAR4-binding protein does not bind, or does not substantially bind to human PAR1, PAR2, or PAR3.

In one example, the PAR4-binding protein comprises a variable heavy chain (VH) sequence set forth as (SEQ ID NO:110):

QX$_1$QLVESGGGVVQPGRSLRLSCX$_2$ASGFX$_3$X$_4$SX$_5$X$_6$GMHWVRQAPGKG

LEWVX$_7$VIWX$_8$DGX$_9$X$_{10}$X$_{11}$X$_{12}$YX$_{13}$DSVX$_{14}$GRFX$_{15}$ISRDX$_{16}$SKN

TX$_{17}$X$_{18}$LQMNX$_{19}$LRAEDTAVYYCAREX$_{20}$X$_{21}$X$_{22}$X$_{23}$X$_{24}$X$_{25}$X$_{26}$P

FDYWGQGTLVTVSS wherein
$X_1$ is V or I;
$X_2$ is A or V;
$X_3$ is T or A;
$X_4$ is L or F;
$X_5$ is N or S;
$X_6$ is Y or D;
$X_7$ is S or A;
$X_8$ is Y or F;
$X_9$ is S or R;
$X_{10}$ is N or S;
$X_{11}$ is K or R;
$X_{12}$ is H or Y;
$X_{13}$ is A, L or T;
$X_{14}$ is K or R;
$X_{15}$ is T or D;
$X_{16}$ is N or T;
$X_{17}$ is L or Q;
$X_{18}$ is Y or F;
$X_{19}$ is S or I;
$X_{20}$ is S or T;
$X_{21}$ is I, S or A;
$X_{22}$ is V, I, M or L;
$X_{23}$ is E, S, V or I;
$X_{24}$ is V, T, R or G;
$X_{25}$ is L, R, or G; and
$X_{26}$ is P or V.

In one example, the PAR4-binding protein further comprises a variable light chain (VL) sequence set forth in (SEQ ID NO: 111):

X$_1$IVLTQSPGTLSLSPGERX$_2$TLSCX$_3$X$_4$SQX$_5$X$_6$RX$_7$X$_8$YLAWX$_9$QQKP

GQAPRLX$_{10}$IYGASSRATGX$_{11}$PDRFSGSGSGTDFX$_{12}$X$_{13}$TIX$_{14}$RLEP

EDFAX$_{15}$YYCQQYGX$_{16}$SYTFGQGTKLEIK wherein
$X_1$ is K or E;
$X_2$ is V or A;
$X_3$ is R or G;
$X_4$ is A or T;
$X_5$ is R or S;
$X_6$ is V or I;
$X_7$ is N or S;
$X_8$ is N or S;
$X_9$ is F or Y;
$X_{10}$ is F or L;
$X_{11}$ is I or T;
$X_{12}$ is I or T;
$X_{13}$ is F or L;
$X_{14}$ is S or T;
$X_{15}$ is V or L; and
$X_{16}$ is N, R or S.

In one example, the VH comprises a CDR1 sequence selected from the group consisting of:
(i) GFTLSNYG (SEQ ID NO:13);
(ii) GFTFSSDG (SEQ ID NO:59);
(iii) GFTFSNYG (SEQ ID NO:68);
(iv) GFTFSSYG (SEQ ID NO:55);
(v) GFAFSSYG (SEQ ID NO:70); and
(vi) GFTLSSYG (SEQ ID NO:75).

In one example, the VH comprises a CDR2 sequence selected from the group consisting of:
(i) IWYDGSNK (SEQ ID NO:14);
(ii) IWFDGRNK (SEQ ID NO:60);
(iii) IWYDGSNR (SEQ ID NO:71; and
(iv) IWYDGSSK (SEQ ID NO:76).

In one example, the VH comprises a CDR3 sequence selected from the group consisting of:
(i) ARESIVEVLPPFDY (SEQ ID NO:15);
(ii) ARESSISTRPPFDY (SEQ ID NO:61);
(iii) ARETIMVRGVPFD (SEQ ID NO:69);
(iv) ARETALVRGVPFDY (SEQ ID NO:56);
(v) ARETAMVRGVPFDY (SEQ ID NO:72); and
(vi) ARETILIGGVPFDY (SEQ ID NO:77).

In one example, the VL comprises a CDR1 sequence selected from the group consisting of:
(i) QRVRNNY (SEQ ID NO:16);
(ii) QSVRSSY (SEQ ID NO:57); and
(iii) QSIRSNY (SEQ ID NO:78).

In one example, the VL comprises the CDR2 sequence GAS (SEQ ID NO:28).

In one example, the VL comprises a CDR3 sequence selected from the group consisting of:
(i) QQYGNSYT (SEQ ID NO:18);
(ii) QQYGRSYT (SEQ ID NO:62); and
(iii) QQYGSSYT (SEQ ID NO:58).

In another example, the PAR4-binding protein comprises a variable heavy chain (VH) sequence set forth in:

In another example, the PAR4-binding protein comprises a variable heavy chain (VH) sequence set forth as (SEQ ID NO: 112):

QVQLQQWGAGLLKPSETLX$_1$LX$_2$CAX$_3$X$_4$X$_5$GSX$_6$SX$_7$YX$_8$WX$_9$WIX$_{10}$Q

PPGKGLEWIGEIX$_{11}$HX$_{12}$GX$_{13}$TX$_{14}$YNPSLKSRVTISVDTSKX$_{15}$QX$_{16}$

SLX$_{17}$LSSVTAADTAVYYCX$_{18}$X$_{19}$EX$_{20}$SX$_{21}$SX$_{22}$GX$_{23}$YYYGMDVWG

QGTTVTVSS wherein
$X_1$ is A or S;
$X_2$ is T or A;
$X_3$ is V or I;
$X_4$ is Y or S;
$X_5$ is G or S;
$X_6$ is L or F;
$X_7$ is N, D or T;
$X_8$ is Y or F;
$X_9$ is S or R;
$X_{10}$ is R or H;
$X_{11}$ is N or I;
$X_{12}$ is S or T;
$X_{13}$ is T or S;

$X_{14}$ is N or T;
$X_{15}$ is K or N;
$X_{16}$ is F or L;
$X_{17}$ is K or N;
$X_{18}$ is A or K;
$X_{19}$ is I, F or V;
$X_{20}$ is Y or H;
$X_{21}$ is N or S;
$X_{22}$ is R, G or S; and
$X_{23}$ is V or H.

In one example, PAR4-binding protein further comprises a variable light chain (VL) sequence set forth in (SEQ ID NO: 113):

DIQMTQSPSSLSAS$X_1$GDR$X_2$TITCRASQ$X_3$IS$X_4$YLNWYQQ$X_5$PGKAP$X_6$LLIYAAS$X_7$L$X_8$SGVPSRFSGSGSGTDFTLTISSLQPEDF$X_9 X_{10}$YYC$X_{11}$Q$X_{12}$Y$X_{13}$TPLTFGGGTK$X_{14}$IK wherein
$X_1$ is V or A;
$X_2$ is V or I;
$X_3$ is S or T
$X_4$ is S, Y or N;
$X_5$ is K or I;
$X_6$ is N or K;
$X_7$ is R or S;
$X_8$ is R or Q;
$X_9$ is T or A
$X_{10}$ is T or S;
$X_{11}$ is Q or R;
$X_{12}$ is T, S or N;
$X_{13}$ is N or N;
$X_{14}$ is E or G.

In one example, the VH comprises a CDR1 sequence selected from the group consisting of:
(i) GGSLSDYY (SEQ ID NO:86);
(iii) SGSFSTYF (SEQ ID NO:47); and
(iv) GGSFSNYY (SEQ ID NO:66).

In one example, the VH comprises a CDR2 sequence selected from the group consisting of:
(i) INHSGTT (SEQ ID NO:87);
(ii) IIHTGST (SEQ ID NO:64); or
(iii) INHSGST (SEQ ID NO:48).

In one example, the VH comprises a CDR3 sequence selected from the group consisting of:
(i) AIEYSNSRGYYYGMDV (SEQ ID NO:88);
(ii) AFEYSSSGGYYYGMDV (SEQ ID NO:49); and
(iii) KVEHSSSSGHYYYGMDV (SEQ ID NO:65).

In one example, the VL comprises a CDR1 sequence selected from the group consisting of:
(i) QTISNY (SEQ ID NO:109);
(ii) QSISSY (SEQ ID NO:50); and
(iii) QTISYY (SEQ ID NO:66).

In one example, the VL comprises the CDR2 sequence AAS (SEQ ID NO:51).

In one example, the VL comprises a CDR3 sequence selected from the group consisting of:
(i) RQNYNTPLT (SEQ ID NO:85);
(iii) QQTYSTPLT (SEQ ID NO:52); or
(iv) QQSYSTPLT (SEQ ID NO:67).

The present disclosure also provides a PAR4 binding protein, comprising a variable heavy chain (VH) having a CDR1, CDR2 and CDR3 sequence comprising or consisting of respectively:

(i) SEQ ID NO:13, SEQ ID NO:14 and SEQ ID NO:15;
(ii) SEQ ID NO:47, SEQ ID NO:48 and SEQ ID NO:49
(iii) SEQ ID NO:24, SEQ ID NO:25 and SEQ ID NO:26;
(iv) SEQ ID NO:55, SEQ ID NO:14 and SEQ ID NO:56;
(v) SEQ ID NO:59, SEQ ID NO:60 and SEQ ID NO:61;
(vi) SEQ ID NO:63, SEQ ID NO:64 and SEQ ID NO:65;
(vii) SEQ ID NO:68, SEQ ID NO:14 and SEQ ID NO:69;
(viii) SEQ ID NO:70, SEQ ID NO:71 and SEQ ID NO:72;
(ix) SEQ ID NO:55, SEQ ID NO:73 and SEQ ID NO:74;
(x) SEQ ID NO:75, SEQ ID NO:76 and SEQ ID NO:77;
(xi) SEQ ID NO:79, SEQ ID NO:80 and SEQ ID NO:81;
(xii) SEQ ID NO:82, SEQ ID NO:80 and SEQ ID NO:83;
(xiii) SEQ ID NO:55, SEQ ID NO:73 and SEQ ID NO:74; or
(xiv) SEQ ID NO:86, SEQ ID NO:87 and SEQ ID NO:88.

The present disclosure also provides a PAR4 binding protein, comprising a variable light chain (VL) having a CDR1, CDR2 and CDR3 sequence comprising or consisting of respectively:

(i) SEQ ID NO:16, SEQ ID NO:17 and SEQ ID NO:18;
(ii) SEQ ID NO:50, SEQ ID NO:51 and SEQ ID NO:52;
(iii) SEQ ID NO:27, SEQ ID NO:28 and SEQ ID NO:29;
(iv) SEQ ID NO:57, SEQ ID NO:28 and SEQ ID NO:58;
(v) SEQ ID NO:57, SEQ ID NO:28 and SEQ ID NO:62;
(vi) SEQ ID NO:66, SEQ ID NO:51 and SEQ ID NO:67;
(vii) SEQ ID NO:57, SEQ ID NO:28 and SEQ ID NO:58;
(viii) SEQ ID NO:57, SEQ ID NO:28 and SEQ ID NO:58;
(ix) SEQ ID NO:78, SEQ ID NO:28 and SEQ ID NO:62;
(x) SEQ ID NO:84, SEQ ID NO:51 and SEQ ID NO:85;
(xi) SEQ ID NO:57, SEQ ID NO:28 and SEQ ID NO:58;
(xii) SEQ ID NO:57, SEQ ID NO:51 and SEQ ID NO:58; or
(xiii) SEQ ID NO:109, SEQ ID NO:51 and SEQ ID NO:85.

In one example, the PAR-4 binding protein comprises:
(i) a VH comprising a sequence which is at least 50% identical to the sequence set forth in any one of SEQ ID NO:11, SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107 or a humanized, chimeric or deimmunized version thereof; and/or
(ii) a VL comprising a sequence which is at least 85% identical to the sequence set forth in SEQ ID NO: 12, SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108 or a humanized, chimeric or deimmunized version thereof.

In one example, the VH comprises a sequence which is at least 55%, 60%, 65%, 70%, 75%, 80%, 85%, 90%, 95%, 97%, 98%, 99% or 99.5% identical to any one of SEQ ID NO:11, SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107.

In one example, the VL comprises a sequence which is at least 60%, 65%, 70%, 75%, 80%, 85%, 90%, 95%, 97%, 98%, 99% or 99.5% identical to any one of SEQ ID NO:12, SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108.

In one example, the VH comprises a sequence which is at least 55%, 60%, 65%, 70%, 75%, 80%, 85%, 90%, 97%, 98%, 99% or 99.5% identical to SEQ ID NO:11 SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107, excluding the CDR sequences.

In one example, the VL comprises a sequence which is at least 60%, 65%, 70%, 75%, 80%, 85%, 90%, 95%, 97%, 98%, 99% or 99.5% identical to SEQ ID NO:12, SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108, excluding the CDR sequences.

In one example, the CDRs are defined by the IMGT numbering system.

The present disclosure also provides a PAR4-binding protein comprising:
(i) a VH set forth in SEQ ID NO:11 and a VL set forth in SEQ ID NO:12;
(ii) a VH set forth in SEQ ID NO:45 and a VL set forth in SEQ ID NO:46;
(iii) a VH set forth in SEQ ID NO:22 and a VL set forth in SEQ ID NO:23;
(iv) a VH set forth in SEQ ID NO:53 and a VL set forth in SEQ ID NO:54;
(v) a VH set forth in SEQ ID NO:89 and a VL set forth in SEQ ID NO:90;
(vi) a VH set forth in SEQ ID NO:91 and a VL set forth in SEQ ID NO:92;
(vii) a VH set forth in SEQ ID NO:93 and a VL set forth in SEQ ID NO:94;
(viii) a VH set forth in SEQ ID NO:95 and a VL set forth in SEQ ID NO:96;
(ix) a VH set forth in SEQ ID NO:97 and a VL set forth in SEQ ID NO:98;
(x) a VH set forth in SEQ ID NO:99 and a VL set forth in SEQ ID NO:100;
(xi) a VH set forth in SEQ ID NO:101 and a VL set forth in SEQ ID NO:102;
(xii) a VH set forth in SEQ ID NO:103 and a VL set forth in SEQ ID NO:104;
(xiii) a VH set forth in SEQ ID NO:105 and a VL set forth in SEQ ID NO:106; or
(xiv) a VH set forth in SEQ ID NO:107 and a VL set forth in SEQ ID NO:108.

In one example, the PAR4-binding protein antigen-binding fragment is:
(i) a single chain Fv fragment (scFv);
(ii) a dimeric scFv (di-scFv);
(iii) at least one of (i) and/or (ii) linked to a heavy chain constant region or an Fc or a heavychain constant domain (CH) 2 and/or CH3; or
(iv) at least one of (i) and/or (ii) linked to a protein that binds to platelets (e.g. von Willebrand factor (vWF)).

In another example of the disclosure, the VL and VH are in separate polypeptide chains. For example, the PAR4-binding protein is:
(i) a diabody;
(ii) a triabody;
(iii) a tetrabody;
(iv) a Fab;
(v) a F(ab')2;
(vi) a Fv; or
(vii) at least one of (i) to (vi) linked to a heavy chain constant region or an Fc or a heavy chain constant domain (CH) 2 and/or CH3; or
(viii) at least one of (i) to (vi) linked to a protein that binds to platelets (e.g. vWF).

The present disclosure also provides a chimeric antibody comprising a VH and a VL as described herein wherein the VH is linked to a human heavy chain constant region and the VL is linked to a human light chain constant region.

It will be apparent to the skilled person based on the disclosure herein that the PAR4-binding proteins of the present disclosure encompasses human, humanized, synhumanized, chimeric and primatized proteins.

The antibodies of the present disclosure may belong to any class, including IgM, IgG, IgE, IgA, IgD, or subclass. Exemplary subclasses for IgG are IgG1, IgG2, IgG3 and IgG4.

In one example, the PAR4-binding protein is recombinant. In one example the PAR4-binding protein is synthetic.

In one example, a PAR4-binding protein or antibody of the present disclosure is conjugated to a moiety. For example, the moiety is selected from the group consisting of a radioisotope, a detectable label, a therapeutic compound, a colloid, a toxin, a nucleic acid, a peptide, a protein, a compound that increases the half-life of the PAR4-binding protein in a subject and mixtures thereof.

The present disclosure also provides an isolated nucleic acid encoding the PAR4-binding protein or antibody of the disclosure. In one example, the PAR4-binding protein or antibody comprises a VH nucleic acid sequence set forth in SEQ ID NO:20 and/or a VL nucleic acid sequence set forth in SEQ ID NO:21. In another example, the PAR4-binding protein or antibody comprises a VH nucleic acid sequence set forth in SEQ ID NO:30 and/or a VL nucleic acid sequence set forth in SEQ ID NO:31.

The present disclosure additionally provides an expression construct comprising the nucleic acid of the disclosure operably linked to a promoter. Such an expression construct can be in a vector, e.g., a plasmid.

In examples of the disclosure directed to single polypeptide PAR4-binding proteins, the expression construct may comprise a promoter linked to a nucleic acid encoding that polypeptide chain.

In examples directed to multiple polypeptides that form a PAR4-binding protein, an expression construct of the disclosure comprises a nucleic acid encoding one of the polypeptides (e.g., comprising a VH) operably linked to a promoter and a nucleic acid encoding another of the polypeptides (e.g., comprising a VL) operably linked to another promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide.

For example, the first polypeptide comprises a VH and the second polypeptide comprises a VL, or the first polypeptide comprises a VL and the second polypeptide comprises a VH.

The present disclosure also contemplates separate expression constructs one of which encodes a first polypeptide (e.g., comprising a VH and optionally heavy chain constant region or part thereof) and another of which encodes a second polypeptide (e.g., comprising a VL and optionally light chain constant region). For example, the present disclosure also provides a composition comprising:
(i) a first expression construct comprising a nucleic acid encoding a polypeptide (e.g., comprising a VH operably linked to a promoter); and (ii) a second expression construct comprising a nucleic acid encoding a polypeptide (e.g., comprising a VL operably linked to a promoter), wherein the first and second polypeptides associate to form a PAR4-binding protein of the present disclosure.

The present disclosure additionally provides an isolated cell expressing the PAR4-binding protein or antibody of the present disclosure or a recombinant cell genetically-modified to express a PAR4-binding protein or antibody of the disclosure. In one example, the cell is an isolated hybridoma. In another example, the cell comprises the nucleic acid of or the expression construct of the disclosure or:

(i) a first expression construct comprising a nucleic acid encoding a polypeptide (e.g., comprising a VH) operably linked to a promoter; and (ii) a second expression construct comprising a nucleic acid encoding a polypeptide (e.g., comprising a VL) operably linked to a promoter, wherein the first and second polypeptides associate to form a PAR4-binding protein or antibody of the present disclosure.

The present disclosure additionally provides a composition comprising the PAR4-binding protein or the nucleic acid or the expression construct or the cell of the present disclosure and a suitable carrier. In one example, the composition comprises the PAR4-binding protein of the present disclosure.

In one example, the carrier is pharmaceutically acceptable.

The composition of the present disclosure may be administered alone or in combination with other treatments, therapeutics or agents, either simultaneously or sequentially.

The present disclosure additionally provides a method for treating or preventing thrombosis or a thromboembolic disorder in a subject, the method comprising administering the PAR4-binding protein or the nucleic acid or the expression construct or the cell or the composition of the present disclosure to the subject. In one example, the subject is one who is at risk of a PAR4-mediated event such as thrombosis. In one example, the subject is one who has, or who previously has had a PAR4-mediated event e.g. thrombosis.

In one example, the method comprises administering an antibody to the subject comprising a VH comprising a sequence set forth in any one of SEQ ID NO:11, SEQ ID NO:22, SEQ ID NO:45, SEQ ID NO:53, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, or SEQ ID NO:107, or a humanized or deimmunized version thereof and a VL comprising a sequence set forth in any one of SEQ ID NO: 12, SEQ ID NO:23, SEQ ID NO:46, SEQ ID NO:54, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, or SEQ ID NO:108 or a humanized or deimmunized version thereof.

The present disclosure additionally provides the PAR4-binding protein or the nucleic acid or the expression construct or the cell or the composition of the present disclosure for use in medicine.

The present disclosure additionally provides the PAR4-binding protein or the nucleic acid or the expression construct or the cell or the composition of the present disclosure for use in the treatment or prophylaxis of an PAR4-mediated event (e.g. thrombosis).

In one example, the present disclosure provides a method of treating, preventing or ameliorating thrombosis or a thromboembolic disorder, comprising administering to a subject in need thereof the PAR4-binding protein or the nucleic acid or the expression construct or the cell or the composition of the present disclosure.

In some examples, the disclosure provides a method of treating, preventing or ameliorating thrombosis in a subject in need thereof comprising administering to a subject in need thereof the PAR4-binding protein or the nucleic acid or the expression construct or the cell or the composition of the present disclosure.

In one example, the disclosure provides a method of reducing the risk of thrombosis associated with a surgical procedure, the method comprising administering to the subject the PAR4-binding protein or the nucleic acid or the expression construct or the cell or the composition of the present disclosure either prior to and/or following a surgical procedure. In one example, the surgical procedure is liver transplantation and the thrombosis is hepatic artery thrombosis.

In some examples, the disclosure provides a method for determining if the dose of PAR4-binding protein or antibody according to the present disclosure is appropriate. Such methods comprise (i) obtaining a blood sample from a subject that has been treated with a PAR4-binding protein or antibody or the present disclosure, (ii) treating platelets from the blood sample with a PAR4 agonist in vitro, (iii) measuring platelet activation and (iv) comparing the platelet activation in the blood sample following treatment with the PAR4-binding protein or antibody, with the platelet activation in a blood sample obtained prior to treatment with the PAR4-binding protein or antibody.

Examples of suitable PAR4 agonists will be familiar to persons skilled in the art. Non-limiting examples include agonist peptides such as AYPGKF-$NH_2$ (Tocris).

In one example, platelet activation is measured according to methods exemplified herein in the Examples.

In some embodiments, the present disclosure includes a method of inhibiting or preventing platelet aggregation, which includes the step of administering to a subject (such as a human) in need thereof a therapeutically effective amount of the PAR4-binding protein according to the present disclosure.

In some examples, the disclosure provides a method of treatment or prophylaxis of thrombosis or a thromboembolic disorder involving administering to a subject in need thereof (e.g., a human) a therapeutically effective amount of the PAR4-binding protein according to the present disclosure and inhibits PAR4 cleavage and/or signalling, wherein said subject has a dual PAR1/PAR4 platelet receptor repertoire.

Preferably, the subject is a human.

The present disclosure additionally provides for use of the PAR4-binding protein or the nucleic acid or the expression construct or the cell or the composition of the present disclosure in medicine.

The present disclosure additionally provides for use of the PAR4-binding protein or the nucleic acid or the expression construct or the cell of the present disclosure in the manufacture of a medicament for the treatment or prophylaxis of thrombosis or a thromboembolic disorder.

The present disclosure additionally provides a method for detecting PAR4 in a sample, the method comprising contacting a sample with the PAR4-binding protein or antibody of the present disclosure such that an antigen-protein complex forms and detecting the complex, wherein detecting the complex is indicative of PAR4 in the sample.

The present disclosure also provides a vaccine antigen comprising or consisting of the sequence according to SEQ ID NO:4, together with a pharmaceutically acceptable carrier for generating antagonist antibodies of human PAR4.

The present disclosure also provides PAR-4 binding proteins that do not, or only partially inhibit cleavage of PAR-4 in the presence of thrombin.

Thus, in one example, the present disclosure also provides a PAR4-binding protein comprising:

(i) a VH comprising a sequence which is at least 50% identical to the sequence set forth in SEQ ID NO:32 or a humanized, chimeric or deimmunized version thereof; and/or (ii) a VL comprising a sequence which is at least 85% identical to the sequence set forth in SEQ ID NO: 33 or a humanized, chimeric or deimmunized version thereof.

BRIEF DESCRIPTION OF THE DRAWINGS

FIG. 5 shows (A) ELISA-based screen of binding of hybridoma supernatants of 5A.RC3 (dark) and 5B.RB4 (light) over immobilised proteins corresponding to the immunogen PAR4 as well as corresponding regions of PARs 1, 2 and 3. (B) Biacore analysis of the binding affinity of the PAR4 antibody of 5A.RC3 sub-clone to human PAR4 peptide measured at different concentrations.

FIG. 6 5A.RC3 inhibits thrombin cleavage of both Ala120 and Thr120 PAR4 variants. To assess thrombin cleavage of PAR4 variants HEK293T cells were transiently transfected with either PAR4-120Ala or PAR4-120Thr variants which contained a FLAG epitope upstream of the thrombin cleavage site. (A) Cells were stimulated with increasing doses of thrombin (0.1-2 U/mL), and amount of thrombin cleavage was measured as a loss of FLAG-epitope using a FITC-conjugated anti-FLAG antibody by flow cytometry. (B) Pre-incubation of transfected cells with 5A.RC3 before thrombin stimulation provided near complete inhibition of thrombin cleavage, to the same extent regardless of PAR4 variant. Doses of 1, 10 and 100 µg/ml of 5A.RC3 were compared.

FIG. 7 5A.RC3 sub-clone inhibits the up-regulated thrombin-induced platelet aggregation response in donors with the PAR4 Thr120 variant. Human isolated platelets of different PAR4 variants were assessed for their responses to platelet aggregation responses to PAR4 agonists. As predicted, the presence of the T allele is associated with higher maximum aggregation in response to mid-range doses of (A) PAR4-AP and (B) thrombin, with a similar trend observed for (C) thrombin stimulation in the presence of PAR1 blockade with vorapaxar (90 nM). (D) Concentration-response of 5A.RC3 inhibitory activity against thrombin-induced platelet aggregation in the presence of a PAR1 antagonist (i.e. PAR4-dependant) showing efficacy against Thr120 variant, indicating antibody-mediated PAR4 inhibition is equally effective across all genotypes. (E) IC50 of 5A.RC3 inhibitory activity in PAR4-dependant thrombin-induced platelet aggregation.

FIGS. 10-1 & 10-2 shows 5A.RC3 sub-clone inhibits thrombosis regardless of donor genotype. The following thrombosis parameters were measured in real-time over a period of 10 minutes in a human whole blood thrombosis assay under conditions of coagulation: (A) platelet deposition (PE-conjugated anti-CD9), thrombin activity (FRET-based thrombin probe), fibrin volume (Dylight650-conjugated anti-fibrin antibody), and the ratio of fibrin per thrombus (data shown is at the 10 minute endpoint). Note that the direct thrombin inhibitor, hirudin (800 U/mL), abolished thrombin activity and fibrin volume despite continued platelet deposition. (B-E) we observed no significant differences in these parameters across PAR4 genotypes. Pre-treatment with 5A.RC3 (open bars, 100 µg/mL) had no effect on (F) platelet deposition, but significantly inhibited (G) thrombin activity (H) fibrin volume and (I) the ratio of fibrin per thrombus volume compared to the control (black bars). Data is mean±SEM of N=4-6 per genotype (n=15 total; colours indicate PAR4 genotype: black circles=AA, grey circles=AT, white circles=TT). For (G) and (H) data were normalized against the hirudin baseline and expressed as a percentage of the untreated control. Statistical significance was determined by one-way ANOVA (B-E) or Students T test (F-G), * indicates P<0.05.

FIG. 12 shows the VH (A) and VL (B) amino acid sequence of MoB5A-RC3.F10b.H4b (5A.RC3) with CDRs identified according to IMGT numbering. VH=heavy chain variable region, VL=light chain variable region, CDR=complementarity determining region and FWR=framework region. This Ab demonstrated PAR4 inhibitory function.

FIG. 13 shows the VH (A) and VL (B) amino acid sequence of MoB5H-RD2.A7b (5H.RD2) with CDRs identified according to IMGT numbering. VH=heavy chain variable region, VL=light chain variable region, CDR=complementarity determining region and FWR=framework region. This Ab bound to PAR4 but did not demonstrate inhibitory function against PAR4.

FIG. 14 shows the VH (A) and VL (B) amino acid sequence of MoB5F-RF3.A7b.C9 (5F.RF3) with CDRs identified according to IMGT numbering. VH=heavy chain variable region, VL=light chain variable region, CDR=complementarity determining region and FWR=framework region. This Ab demonstrated PAR4 inhibitory function.

FIGS. 20-1 & 20-2 shows sequences of the variable heavy chain of anti-PAR4 mAbs showing the complementary determining regions (CDRs) according to the IMGT numbering system.

FIGS. 21-1 & 21-2 shows sequences of the variable light chain of anti-PAR4 mAbs showing the complementary determining regions (CDRs) according to the IMGT numbering system.

FIG. 22 shows synthetic peptides for epitope mapping of anti-hPAR4 mAb's. Overlapping peptides spanning the original human PAR4 antigen were synthesised, these consisted of amino acid residues 1-9, amino acid residues 8-15 and amino acid residues 11-20. The sequence of the thrombin cleavage site is underlined. The C-terminal Cysteine residue has been removed to prevent formation of multimers.

KEY TO SEQUENCE LISTING

Figure 1:
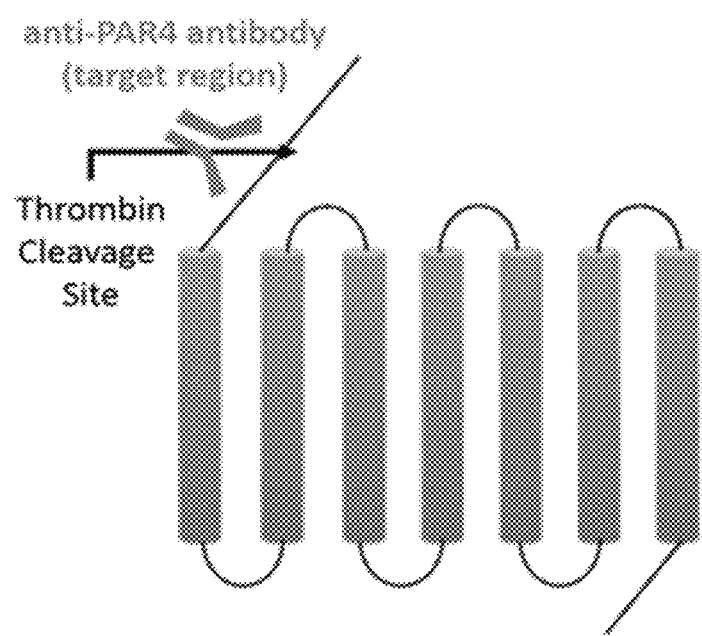
FIG. 1 shows a schematic of the extracellular location of the thrombin cleavage and activation site of PAR4 and the anti-PAR4 target region of the antibodies described herein.

SEQ ID NO:1: epitope sequence of PAR4
SEQ ID NO:2: sequence of hPAR4 (naked)
SEQ ID NO:3: sequence of mPAR4 (naked)
SEQ ID NO:4: sequence of hPAR4 (KLH) used as an immunogen
SEQ ID NO:5: sequence of mPAR4 (KLH) used as an immunogen
SEQ ID NO:6 sequence mPAR4 (Biotin)
SEQ ID NO:7: sequence of hPAR4 (Biotin)
SEQ ID NO:8: sequence of hPAR3 (Biotin)
SEQ ID NO:9: sequence of hPAR2 (Biotin)
SEQ ID NO:10: sequence of hPAR1 (Biotin)
SEQ ID NO:11: amino acid sequence of 5A.RC3 VH
SEQ ID NO:12: amino acid sequence of 5A.RC3 VL
SEQ ID NO:13: sequence of 5A.RC3 VH CDR1
SEQ ID NO:14: sequence of 5A.RC3 VH CDR2
SEQ ID NO:15: sequence of 5A.RC3 VH CDR3
SEQ ID NO:16: sequence of 5A.RC3 VL CDR1
SEQ ID NO:17: sequence of 5A.RC3 VL CDR2
SEQ ID NO:18: sequence of 5A.RC3 VL CDR3
SEQ ID NO:19: sequence of human PAR4
SEQ ID NO:20: nucleic acid sequence of 5A.RC3 VH
SEQ ID NO:21: nucleic acid sequence of 5A.RC3 VL
SEQ ID NO:22: amino acid sequence of 5A.RC3 VH
SEQ ID NO:23: amino acid sequence of 5F.RF3 VL (5F.RF3)
SEQ ID NO:24: sequence of 5F.RF3 VH CDR1
SEQ ID NO:25: sequence of 5F.RF3 VH CDR2
SEQ ID NO:26: sequence of 5F.RF3 VH CDR3
SEQ ID NO:27: sequence of 5F.RF3 VL CDR1
SEQ ID NO:28: sequence of 5F.RF3 VL CDR2
SEQ ID NO:29: sequence of 5F.RF3 VL CDR3
SEQ ID NO:30: nucleic acid sequence of 5F.RF3 VH
SEQ ID NO:31: nucleic acid sequence of 5F.RF3 VL
SEQ ID NO:32: amino acid sequence of 5H.RD2 VH
SEQ ID NO:33: amino acid sequence of 5H.RD2 VL
SEQ ID NO:34: sequence of 5H.RD2 VH CDR1
SEQ ID NO:35: sequence of 5H.RD2 VH CDR2
SEQ ID NO:36: sequence of 5H.RD2 VH CDR3
SEQ ID NO:37: sequence of 5H.RD2 VL CDR1
SEQ ID NO:38: sequence of 5H.RD2 VL CDR2
SEQ ID NO:39: sequence of 5H.RD2 VL CDR3
SEQ ID NO:40: nucleic acid sequence of 5H.RD2 VH
SEQ ID NO:41: nucleic acid sequence of 5H.RD2 VL
SEQ ID NO:42: epitope sequence
SEQ ID NO:43: epitope sequence
SEQ ID NO:44: epitope sequence
SEQ ID NO:45: amino acid sequence of 5I.RG1 VH
SEQ ID NO:46: amino acid sequence of 5I.RG1 VL
SEQ ID NO:47: sequence of 5I.RG1 VH CDR1
SEQ ID NO:48: sequence of 5I.RG1 VH CDR2
SEQ ID NO:49: sequence of 5I.RG1 VH CDR3
SEQ ID NO:50: sequence of 5I.RG1 VL CDR1
SEQ ID NO:51: sequence of 5I.RG1 VL CDR2
SEQ ID NO:52: sequence of 5I.RG1 VL CDR3
SEQ ID NO:53 amino acid sequence of 5G.RA1 VH
SEQ ID NO:54: amino acid sequence of 5G.RA1 VL
SEQ ID NO:55: sequence of 5G.RA1 VH CDR1
SEQ ID NO:14: sequence of 5G.RA1 VH CDR2
SEQ ID NO:56: sequence of 5G.RA1 VH CDR3
SEQ ID NO:57: sequence of 5G.RA1 VL CDR1
SEQ ID NO:28: sequence of 5G.RA1 VL CDR2
SEQ ID NO:58: sequence of 5G.RA1 VL CDR3
SEQ ID NO:89 amino acid sequence of 5D.RH4 VH
SEQ ID NO:90 amino acid sequence of 5D.RH4 VL SEQ ID NO:59 sequence of 5D.RH4 VH CDR1
SEQ ID NO:60 sequence of 5D.RH4 VH CDR2
SEQ ID NO:61 sequence of 5D.RH4 VH CDR3
SEQ ID NO:57 sequence of 5D.RH4 VL CDR1
SEQ ID NO:28 sequence of 5D.RH4 VL CDR2
SEQ ID NO:62 sequence of 5D.RH4 VL CDR3
SEQ ID NO:91 amino acid sequence of 5H.RH4 VH
SEQ ID NO:92 amino acid sequence of 5H.RH4 VL
SEQ ID NO:63 sequence of 5H.RH4 VH CDR1
SEQ ID NO:64 sequence of 5H.RH4 VH CDR2
SEQ ID NO:65 sequence of 5H.RH4 VH CDR3
SEQ ID NO:66 sequence of 5H.RH4 VL CDR1
SEQ ID NO:51 sequence of 5H.RH4 VL CDR2
SEQ ID NO:67 sequence of 5H.RH4 VL CDR3
SEQ ID NO:93 amino acid sequence of 5G.RF6 VH
SEQ ID NO:94 amino acid sequence of 5G.RF6 VL
SEQ ID NO:68 sequence of 5G.RF6 VH CDR1
SEQ ID NO:14 sequence of 5G.RF6 VH CDR2
SEQ ID NO:69 sequence of 5G.RF6 VH CDR3
SEQ ID NO:57 sequence of 5G.RF6 VL CDR1
SEQ ID NO:28 sequence of 5G.RF6 VL CDR2
SEQ ID NO:58 sequence of 5G.RF6 VL CDR3
SEQ ID NO:95 amino acid sequence of 5G.RD6 VH
SEQ ID NO:95 amino acid sequence of 5G.RD6 VL
SEQ ID NO:70 sequence of 5G.RD6 VH CDR1
SEQ ID NO:71 sequence of 5G.RD6 VH CDR2
SEQ ID NO:72 sequence of 5G.RD6 VH CDR3
SEQ ID NO:57 sequence of 5G.RD6 VL CDR1
SEQ ID NO:28 sequence of 5G.RD6 VL CDR2
SEQ ID NO:58 sequence of 5G.RD6 VL CDR3
SEQ ID NO:97 amino acid sequence of 5H.RA3 VH
SEQ ID NO:98 amino acid sequence of 5H.RA3 VL
SEQ ID NO:55 sequence of 5H.RA3 VH CDR1
SEQ ID NO:73 sequence of 5H.RA3 VH CDR2
SEQ ID NO:74 sequence of 5H.RA3 VH CDR3
SEQ ID NO:57 sequence of 5H.RA3 VL CDR1
SEQ ID NO:28 sequence of 5H.RA3 VL CDR2
SEQ ID NO:58 sequence of 5H.RA3 VL CDR3
SEQ ID NO:99 amino acid sequence of 5G.RG1 VH
SEQ ID NO:100 amino acid sequence of 5G.RG1 VL
SEQ ID NO:75 sequence of 5G.RG1 VH CDR1
SEQ ID NO:76 sequence of 5G.RG1 VH CDR2
SEQ ID NO:77 sequence of 5G.RG1 VH CDR3
SEQ ID NO:78 sequence of 5G.RG1 VL CDR1
SEQ ID NO:28 sequence of 5G.RG1 VL CDR2
SEQ ID NO:62 sequence of 5G.RG1 VL CDR3
SEQ ID NO:101 amino acid sequence of 5H.RG4 VH
SEQ ID NO:102 amino acid sequence of 5H.RG4 VL
SEQ ID NO:79 sequence of 5H.RG4 VH CDR1
SEQ ID NO:80 sequence of 5H.RG4 VH CDR2
SEQ ID NO:81 sequence of 5H.RG4 VH CDR3
SEQ ID NO:57 sequence of 5H.RG4 VL CDR1
SEQ ID NO:28 sequence of 5H.RG4 VL CDR2
SEQ ID NO:58 sequence of 5H.RG4 VL CDR3
SEQ ID NO:103 amino acid sequence of 5G.RC5 VH
SEQ ID NO:104 amino acid sequence of 5G.RC5 VL
SEQ ID NO:82 sequence of 5G.RC5 VH CDR1
SEQ ID NO:80 sequence of 5G.RC5 VH CDR2
SEQ ID NO:83 sequence of 5G.RC5 VH CDR3
SEQ ID NO:57 sequence of 5G.RC5 VL CDR1
SEQ ID NO:51 sequence of 5G.RC5 VL CDR2
SEQ ID NO:58 sequence of 5G.RC5 VL CDR3
SEQ ID NO:105 amino acid sequence of 5F.RE6 VH
SEQ ID NO:106 amino acid sequence of 5F.RE6 VL
SEQ ID NO:55 sequence of 5F.RE6 VH CDR1
SEQ ID NO:73 sequence of 5F.RE6 VH CDR2
SEQ ID NO:74 sequence of 5F.RE6 VH CDR3
SEQ ID NO:84 sequence of 5F.RE6 VL CDR1
SEQ ID NO:51 sequence of 5F.RE6 VL CDR2
SEQ ID NO:85 sequence of 5F.RE6 VL CDR3
SEQ ID NO:107 amino acid sequence of 5H.RF2 VH
SEQ ID NO:108 amino acid sequence of 5H.RF2 VL
SEQ ID NO:86 sequence of 5H.RF2 VH CDR1
SEQ ID NO:87 sequence of 5H.RF2 VH CDR2
SEQ ID NO:88 sequence of 5H.RF2 VH CDR3
SEQ ID NO:109 sequence of 5H.RF2 VL CDR1
SEQ ID NO:51 sequence of 5H.RF2 VL CDR2
SEQ ID NO:85 sequence of 5H.RF2 VL CDR3
SEQ ID NO:110 consensus sequence 1 of variable heavy chain
SEQ ID NO:111 consensus sequence 1 of variable light chain
SEQ ID NO:112 consensus sequence 2 of variable heavy chain
SEQ ID NO:113 consensus sequence 2 of variable light chain
SEQ ID NO:114 binding epitope sequence
SEQ ID NO:115 PAR1 screening peptide
SEQ ID NO:116 PAR2 screening peptide
SEQ ID NO:117 PAR3 screening peptide
SEQ ID NO:118 C-terminal amidated peptide PAR4 agonist
SEQ ID NO:119 hPAR4 epitope mapping peptide amino acids 1-9
SEQ ID NO:120 hPAR4 epitope mapping peptide amino acids 8-15
SEQ ID NO:121 hPAR4 epitope mapping peptide amino acids 11-20.

DETAILED DESCRIPTION OF THE INVENTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, Perbal (1984), Sambrook et al., (1989), Brown (1991), Glover and Hames (1995 and 1996), and Ausubel et al., (1988, including all updates until present), Harlow and Lane, (1988), Coligan et al., (including all updates until present) and Zola (1987).

The description and definitions of variable regions and parts thereof, immunoglobulins, antibodies and fragments thereof herein may be further clarified by the discussion in Kabat, 1987 and/or 1991, Bork et al., 1994 and/or Chothia and Lesk, 1987 and/or 1989 or Al-Lazikani et al., 1997 or the IMGT numbering of Lefranc M.-P., (1997) Immunology Today 18, 509.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

The present invention employs conventional molecule biology, microbiology and recombinant DNA techniques within the skill of the art. See for example, Sambrook et al "Molecular Cloning" A Laboratory Manual (1989).

Selected Definitions

As used herein, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent (%), up or down (higher or lower).

It will be understood that the PAR4-binding proteins and antibodies, nucleic acids, cells and vectors described herein are in isolated form. By "isolated" it is meant a polypeptide, antibody, polynucleotide, vector, or cell, that is in a form not found in nature. Isolated polypeptides, antibodies, polynucleotides, vectors, or cells include those which have been purified to a degree that they are no longer in a form in which they are found in nature. In some aspects, an antibody, polynucleotide, vector, or cell that is isolated is substantially pure. In some aspects an antibody, polynucleotide, vector, or cell that is isolated is "recombinant."

As used herein, the term "protease-activated receptor (PAR4)" is meant all or part of a vertebrate cell surface protein which is specifically activated by thrombin or a thrombin agonist thereby activating PAR4-mediated signalling events (e.g., phosphoinositide hydrolysis, Ca efflux, platelet aggregation). The polypeptide is characterized as having the ligand activating properties (including the agonist activating and antagonist inhibiting properties) and tissue distribution described herein. The term includes those portions of PAR4 capable of binding thrombin or the PAR4 receptor portion as set forth in SEQ ID NO: 2.

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%>, 20%>, 30%>, 40%>, 50%>, 60%>, 70%>, 80%>, 90%>, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models).

The term "hPAR4" or "human PAR4" refers to fully human antibodies. For the purpose of nomenclature and not limitation, an amino acid sequence of an hPAR4 is set forth in SEQ ID NO: 19.

The term "mAb" as used herein is intended to refer to monoclonal antibodies comprising mouse constant region sequences and human variable region sequences.

The term "antibody" describes an immunoglobulin whether natural or partly or wholly synthetically produced or recombinantly produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, multivalent antibodies, multispecific antibodies, chimeric antibodies, humanized antibodies, and human antibodies. The term "antibody" also refers to a protein comprising at least two immunoglobulin heavy (H) chains and two immunoglobulin light (L) chains inter-connected by disulfide bonds, or an antigen binding portion thereof. Each heavy chain is comprised of a heavy chain variable region (abbreviated herein as VH) and a heavy chain constant region (abbreviated herein as CH). The CH is normally comprised of three domains, CH1, CH2 and CH3 (IgM, e.g., has an additional constant region domain, CH4). Each light chain is comprised of a light chain variable region (abbreviated herein as VL) and a light chain constant region (abbreviated herein as CL). The CL is comprised of one domain and can be of the lambda or kappa type. The VH and VL regions can be further subdivided into regions of hypervariability, termed complementarity determining regions (CDR), interspersed with regions that are more conserved, termed framework regions (FWR). Each VH and VL is composed of three CDRs and four FWRs, arranged from amino-terminus to carboxy-terminus in the following order: FWR1, CDR1, FWR2, CDR2, FWR3, CDR3, FWR4. In certain embodiments, the VH and VL together comprise a binding domain that interacts with an antigen. In other embodiments a single VH or single VL domain can interact specifically with the antigen. The CH domain of an antibody can mediate the binding of the immunoglobulin to host tissues or factors, including various cells of the immune system (e.g., effector cells), cells lining the vascular wall, other cell expressing receptors for the CH domain of immunoglobulins and the first component (C1q) of the classical complement system. Antibody molecules can be of any class (e.g., IgG, IgE, IgM, IgD, IgA, and IgY), or subclass (e.g., IgG1, IgG2, IgG3, IgG4, IgA1, and IgA2). The term "antibody" as used herein also includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816, 567; and Morrison et al, Proc. Natl. Acad. Sci. USA 81:6851-6855 (1984)). Basic antibody structures in vertebrate systems are well understood. See, e.g., Harlow et al. (1988) Antibodies: A Laboratory Manual (2nd ed.; Cold Spring Harbor Laboratory Press). Also included within the meaning of the term "antibody" are any "antigen-binding fragments".

The term "antigen-binding fragment" refers to one or more fragments of an antibody that retain the ability to specifically bind to an antigen (e.g., PAR4). Fragments of a full-length antibody can perform the antigen-binding function of an antibody. Examples of binding fragments encompassed within the term "antigen-binding fragment" of an antibody include (i) a Fab fragment, a monovalent fragment consisting of the VL and CL, VH and CH1 domains; (ii) a F(ab)2 fragment, a bivalent fragment comprising two Fab fragments linked by a disulfide bridge at the hinge region; (iii) a Fd fragment consisting of the VH and CH1 domains; (iv) a Fv fragment consisting of the VH and CL domains of a single arm of an antibody, (v) a single domain antibody fragment or dAb (Ward et al., (1989) Nature 341:544-546), which consists of a VH domain or a VL domain only; and (vi) an isolated complementarity determining region (CDR). Furthermore, although the two domains of the Fv fragment, VH and VL, are coded for by separate genes, they can be joined, using recombinant or synthetic methods, e.g., by a synthetic linker that enables them to be made as a single protein chain in which the VH and VL regions pair to form monovalent molecules (known as single chain Fv (scFv); see e.g., Bird et al. (1988) Science 242:423-426; and Huston et al. (1988) Proc. Natl. Acad. Sci. USA 85:5879-5883). scFv are also encompassed within the term "antigen-binding fragment" of an antibody. These antibody fragments are obtained using conventional techniques known to those with skill in the art, and the fragments are screened for utility in the same manner as are intact antibodies.

As used herein, "antibody variable region" refers to the portions of the light and heavy chains of antibody molecules that include amino acid sequences of complementarity determining regions (CDRs; i.e., CDR1, CDR2 and CDR3), and framework regions (FWRs). VH refers to the variable region of the heavy chain. VL refers to the variable region of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or Chotia and Lesk 1987 J. Mol Biol. 196:901-917) or according to the IMGT numbering system.

The term "monoclonal antibody" as used herein refers to a preparation of antibody molecules of single molecular composition. A monoclonal antibody displays a single binding specificity and affinity for a particular epitope. The monoclonal antibodies can be generated from any animal, e.g., mouse, rat, rabbit, pig, etc., or can be generated synthetically and be in part or entirely of human sequence.

The term "polyclonal antibody" as used herein refers to a mixture of antibodies purified from the serum of a mammal in which an antigen is injected to generate the antibodies against the antigen. Polyclonal antibodies can be generated from any mammal, e.g., mouse, rat, rabbit, pig, human, etc., or can be generated synthetically, e.g., as a VH and VL gene phage display library.

The term "chimeric antibody" refers to antibodies in which a portion of the heavy and/or light chain is identical with or homologous to corresponding sequences in antibodies derived from a particular species (e.g. murine) or belonging to a particular antibody class or subclass, while the remainder of the chain(s) is identical with or homologous to corresponding sequences in antibodies derived from another species (e.g. primate) or belonging to another antibody class or subclass, as well as fragments of such antibodies, so long as they exhibit the desired biological activity.

The term "humanized antibody" shall be understood to refer to a chimeric molecule, generally prepared using recombinant techniques, having an epitope binding site derived from an immunoglobulin from a non-human species and the remaining immunoglobulin structure of the molecule based upon the structure and/or sequence of a human immunoglobulin. The antigen-binding site preferably comprises the complementarity determining regions (CDRs) from the non-human antibody grafted onto appropriate framework regions in the variable domains of human antibodies and the remaining regions from a human antibody.

The term "human antibody" as used herein in connection with antibody molecules and binding proteins refers to antibodies having variable (e.g. VH, VL, CDR and FR regions) and constant antibody regions derived from or corresponding to sequences found in humans, e.g. in the human germline or somatic cells.

"IMGT numbering" as used herein refers to a numbering system used to identify CDR and FWR sequences of antibody variable regions. The IMGT unique numbering has been defined to compare the variable domains whatever the antigen receptor, the chain type, or the species (Lefranc M.-P., Immunology 5 Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., ThouveninContet, V. and Lefranc, Dev. Comp. Immunol., 27, 55-77 (2003)). In the IMGT unique numbering, the conserved amino acids always have the same position, for instance cysteine 23 ($1^{st}$ CYS), tryptophan 41 (CONSERVED-TRP), hydrophobic amino acid 89, cysteine 104 ($2^{nd}$ CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths become crucial information. The IMGT unique numbering is used in 2D graphical representations, designated as IMGT Colliers de Perles (Ruiz, M. and Lefranc, M.-P., Immunogenetics, 53, 857-883 (2002)/Kaas, Q. and Lefranc, M.-P., Current Bioinformatics, 2, 21-30 (2007)), and in 3D structures in IMGT/3Dstructure-DB (Kaas, Q., Ruiz, M. and Lefranc, M.-P., T cell receptor and MHC structural data. Nucl. Acids. Res., 32, D208-D210 (2004)).

As used herein, the term "specifically binds" shall be taken to mean a protein of the disclosure reacts or associates more frequently, more rapidly, with greater duration and/or with greater affinity with a particular cell or substance than it does with alternative cells or substances. It is also understood by reading this definition that, for example, a protein that specifically binds to a first antigen may or may not specifically bind to a second antigen. As such "specific binding" does not necessarily require exclusive binding or non-detectable binding of another antigen, this is meant by the term "selective binding".

By "transfected", "transfected cell" and the like, is meant a cell into which (or into an ancestor of which) has been introduced, by means of genetic engineering, a DNA molecule encoding a PAR4 (or DNA encoding a biologically active fragment or analog, thereof). Such a DNA molecule is "positioned for expression" meaning that the DNA molecule is positioned adjacent to a DNA sequence which directs transcription and translation of the sequence (i.e., facilitates the production of the PAR4 protein, or fragment or analog, thereof).

The term "identity" and grammatical variations thereof, mean that two or more referenced entities are the same. Thus, where two antibody sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. The % identity of a polynucleotide is determined by GAP (Needleman and Wunsch, J. Mol Biol. 48: 444-453.1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 100 nucleotides in length, and the GAP analysis aligns the two sequences over a region of at least 100 nucleotides. Most preferably, the two sequences are aligned over their entire length.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., Remington: The Science and Practice of Pharmacy, 20th Edition, Mack Publishing Co., Easton, Pa. (2000).

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, the terms "treat" or "treatment" refer to both therapeutic treatment and prophylactic or preventative measures, wherein the object is to prevent or slow down (lessen) an undesired physiological change or disorder, such as the progression of an thromboembolism, e.g., acute coronary syndromes. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, "prophylaxis" or "prevention" refers to the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

The term "therapeutically effective amount" shall be taken to mean a sufficient quantity of a PAR4 binding protein or antibody to reduce or inhibit one or more symptoms of PAR4 activation to a level that is below that observed and accepted as clinically characteristic of that disorder. The skilled artisan will be aware that such an amount will vary depending on the specific antibody, fragment, and/or particular subject and/or type or severity or level of disorder Accordingly, this term is not to be construed to limit the invention to a specific quantity.

The term "PAR4 antagonist therapy" as used herein means treatment of a subject with a PAR4 antagonist.

By "subject" is meant any subject, particularly a mammalian subject, for whom diagnosis, prognosis, or therapy is desired. As used herein, the term "subject" includes any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a subject having a PAR4-mediated condition or disorder", includes subjects, such as mammalian subjects, that would benefit from the administration of a PAR4 antagonist.

As used herein, reference to a "similar" level of binding will be understood to mean that an antibody binds to an antigen at a level within about 30% or 25% or 20% of the level at which it binds to another antigen. This term can also mean that one antibody binds to an antigen at a level within about 30% or 25% or 20% of the level at which another antibody binds to the same antigen.

As used herein, reference to "substantially the same level" of binding will be understood to mean that an antibody binds to an antigen at a level within about 15% or 10% or 5% of the level at which it binds to another antigen. This term can also mean that one antibody binds to an antigen at a level within about 5% or 4% or 3% of the level at which another antibody binds to the same antigen.

The term "competitively inhibits" shall be understood to mean that a protein of the disclosure reduces or prevents binding of a recited antibody (e.g. 5A.RC3) produced to the thrombin-cleavage site of PAR4 or a fragment thereof. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to PAR4 or a fragment thereof either in the presence or absence of the protein. If less antibody binds in the presence of the protein than in the absence of the protein, the protein is considered to competitively inhibit binding of the antibody. In one example, the protein and antibody are exposed to PAR4 substantially simultaneously. Additional methods for determining competitive inhibition of binding will be apparent to the skilled artisan and/or described herein. In one example, the antigen binding domain of the protein competitively inhibits binding of the antibody.

By "overlapping" in the context of two epitopes shall be taken to mean that two epitopes share a sufficient number of amino acid residues to permit an antibody that binds to one epitope to competitively inhibit the binding of an antibody that binds to the other epitope. For example, the epitopes share at least one or two or three or four or five or six or seven or eight or nine or ten amino acids.

As used herein, the term "does not detectably bind" shall be understood to mean that a protein, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the protein is immobilized and contacted with an antigen.

Antibodies

For the avoidance of doubt, monoclonal antibody mAb ARC3 is synonymous with other designations of this antibody as shown in the examples such as MoB5A-RC3. This antibody has been further sub-cloned to derived monoclonal antibody MoB5-ARC3.F10b.H4b. This sub-clone is also referred to as mAb ARC3.H4b. Sequences corresponding to this antibody are found in SEQ ID NOs:11-18.

Functionally Equivalent Antibodies

The present disclosure also contemplates anti-PAR4 antibodies or antigen-binding fragments thereof with one or more amino acid additions, deletions, or substitutions of the heavy and light chain variable region sequences of antibody mAb ARC3.H4b but still retain the function of mAb ARC3.H4b. In some examples, the PAR4-binding protein comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity. Hydropathic indices are described, for example in Kyte and Doolittle (1982) and hydrophylic indices are described in, e.g., U.S. Pat. No. 4,554,101.

These modifications may be deliberate, such as, for example through site-directed mutagenesis, or may be accidental such as those obtained through mutations in hosts that express the antibody.

Mutant (altered) polypeptides can be prepared using any technique known in the art. For example, a polynucleotide of the disclosure can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. Products derived from mutated/altered DNA can readily be screened using techniques described herein to determine if they have receptor-binding and/or -inhibitory activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the antibody and/or immunoglobulin chain molecule, including in the variable region, removed and a different residue inserted in its place. The sites of greatest interest for substitutional mutagenesis include sites identified as important for antigen binding. These sites, especially those falling within a sequence of at least three other identically conserved sites of human antibodies and/or immunoglobulin chains, are preferably substituted in a relatively conservative manner. Such conservative substitutions are shown in Table 1 under the heading of "exemplary substitutions".

Conservative amino acid substitutions are also contemplated by the present invention. These are taken to mean amino acid substitutions set forth in the following Table.

TABLE 1

| Exemplary Substitutions | |
|---|---|
| Original Residue | Exemplary Substitutions |
| Ala (A) | val; leu; ile; gly |
| Arg (R) | Lys |
| Asn (N) | gln; his |
| Asp (D) | Glu |
| Cys (C) | Ser |
| Gln (Q) | asn; his |
| Glu (E) | Asp |
| Gly (G) | pro, ala |
| His (H) | asn; gln |
| Ile (I) | leu; val; ala |
| Leu (L) | ile; val; met; ala; phe |
| Lys (K) | Arg |
| Met (M) | leu; phe |
| Phe (F) | leu; val; ala |
| Pro (P) | Gly |
| Ser (S) | Thr |
| Thr (T) | Ser |
| Trp (W) | Tyr |
| Tyr (Y) | trp; phe |
| Val (V) | ile; leu; met; phe; ala |

The amino acids described herein are preferably in the "L" isomeric form. However, residues in the D isomeric form can be substituted for any L-amino acid residue, as long as the desired functional property of immunoglobulin binding is retained by the polypeptide. Modifications also include structural and functional analogues, for example, peptidomimetics having synthetic or non-natural amino acids or amino acid analogues and derivatized forms.

The present disclosure also contemplates non-conservative amino acid changes. For example, of particular interest are substitutions of charged amino acids with another charged amino acid and with neutral or positively charged amino acids. In some examples, the PAR4-binding protein comprises 10 or fewer, e.g., 9 or 8 or 7 or 6 or 5 or 4 or 3 or 2 or 1 non-conservative amino acid substitutions.

A mutant form of a PAR4-binding protein described herein according to any example retains the ability to specifically bind to PAR4. Methods for determining specific binding to PAR4 are described herein. For example, a labelled PAR4-binding protein is brought into contact with immobilized PAR4, or peptide comprising the thrombin-cleavage site of PAR4 (e.g. as set forth in SEQ ID NO:2). Following washing, bound label is detected. The labelled PAR4-binding protein is also brought into contact with immobilized PAR4 and a related protein or a mutant form of PAR4 or a fragment of PAR4 as discussed above and, following washing, bound label is detected. Detection of label bound to PAR4 but not to the related (e.g. PAR1, PAR2 or PAR3) or mutant protein or a fragment of PAR4 indicates that the mutant PAR4-binding protein retains the ability to specifically bind to PAR4.

In one example, the mutation(s) occur within a FWR of a PAR4-binding protein of the disclosure. In another example, the mutation(s) occur within a CDR of a PAR4-binding protein of the disclosure.

Antibody Generation

Methods for generating antibodies are known in the art and/or described in Harlow and Lane (1988) or Zola (1987). Generally, in such methods an Fnl4 protein or immunogenic fragment or epitope-containing thereof or a cell expressing and displaying same (i.e., an immunogen), optionally formulated with any suitable or desired carrier, adjuvant, or pharmaceutically acceptable excipient, is administered to a non-human animal subject, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. The term "monoclonal antibody" or "mAb" or "MAb" refers to a homogeneous antibody population capable of binding to the same antigen(s) and, for example, to the same epitope within the antigen. This term is not intended to be limited with respect to the source of the antibody or the manner in which it is made.

For the production of mAbs any one of a number of known techniques may be used, such as, for example, the procedure exemplified in U.S. Pat. No. 4,196,265 or Harlow and Lane (1988) Antibodies: A laboratory manual Cold Spring Harbor Laboratory or Zola (1987) Monoclonal antibodies: A manual of techniques.

For example, a suitable animal is immunized with an effective amount of the protein or immunogenic fragment or epitope thereof or cell expressing same under conditions sufficient to stimulate antibody producing cells. Rodents such as rabbits, mice and rats are exemplary animals, with mice being most commonly used. Mice genetically-engineered to express human immunoglobulin proteins, and not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen. B cells and immortal cells are fused by incubating a mixture of the cells types in the presence of an agent or agents (chemical or electrical) that promote the fusion of cell membranes. Fusion methods using Sendai virus have been described by Kohler and Milstein, (1975); and Kohler and Milstein, (1976). Methods using polyethylene glycol (PEG), such as 37% (v/v) PEG, are described by Gefter et al, (1977) Somatic Cell Genet. 3(2):231-6. The use of electrically induced fusion methods is also appropriate.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemistry and/or immunoassay (e.g. radioimmunoassay, enzyme immunoassay, cytotoxicity assay, plaque assay, dot immunoassay, and the like). The present disclosure also contemplates sub-cloning of antibody producing cells, e.g., as exemplified herein.

Alternatively, ABL-MYC technology (NeoClone, Madison Wis. 53713, USA) is used to produce cell lines secreting mAbs (e.g., as described in Kumar et al, (1999) Immunol Lett. 65(3):153-9).

Antibodies can also be produced or isolated by screening a display library, e.g., a phage display library, e.g., as described in U.S. Pat. No. 6,300,064 EP0368684 and/or U.S. Pat. No. 5,885,793.

Chimeric Antibodies and Proteins

In one example an antibody or PAR4-binding protein of the disclosure is a chimeric antibody or a PAR4-binding protein is a chimeric protein. The term "chimeric proteins" refers to proteins in which an antigen binding domain VH or VL is from identical with or homologous to corresponding sequences in proteins derived from a particular species (e.g., murine, such as mouse or rat) or belonging to a particular antibody class or subclass, while the remainder of the chain(s) protein is identical with or homologous to corresponding sequences in from a proteins derived from another species (e.g., primate, such as human) or belonging to another antibody class or subclass. In one example, a chimeric protein is a chimeric antibody comprising a VH and a VL from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331, 415; 5,807,715; 4,816,567 and 4,816,397). The production of such chimeric antibodies is known in the art, and may be achieved by standard means (as described, e.g., in Morrison, Science 229:1202 (1985); Oi et al, BioTechniques 4:214 (1986); Gillies et al, (1989) J. Immunol. Methods 125:191-202; U.S. Pat. Nos. 5,807,715; 4,816,567 and 4,816,397). It is further contemplated that the human constant regions of chimeric antibodies of the invention may be selected from IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant regions.

Humanized and Human Antibodies/Proteins

The PAR4-binding proteins of the present disclosure may be humanized or human.

The term "humanized protein" shall be understood to refer to a protein comprising a human-like variable region including CDRs from an antibody from a non-human species grafted onto or inserted into FRs from a human antibody (this type of antibody is also referred to a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found neither in the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized protein" also encompasses a super-humanized protein, e.g., as described in U.S. Pat. No. 7,732,578.

In one example, a humanized protein comprises the regions between 26 and 33, 51 and 58, and 97 and 110 in a heavy chain sequence disclosed herein and between 27 and 33, 51 and 53, and 90 and 97 (numbering according to the IMGT numbering system).

The term "human protein" as used herein refers to proteins having variable and, optionally, constant antibody regions derived from or corresponding to sequences found in humans, e.g. in the human germline or somatic cells. The "human" antibodies can include amino acid residues not encoded by human sequences, e.g. mutations introduced in vivo random or site directed mutations in vitro (in particular mutations which involve conservative substitutions or mutations in a small number of residues of the protein, e.g. in 1, 2, 3, 4 or 5 of the residues of the protein. These "human antibodies" do not actually need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in or U.S. Pat. No. 5,565,332). This term also encompasses affinity matured forms of such antibodies. A human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Human proteins or antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (Jespers L S et al, (1988) Biotechnology 12(9):899-903).

A human PAR4-binding protein of the disclosure comprises a variable region of a human antibody.

Synhumanized and Primatized Proteins

The PAR4-binding proteins of the present disclosure may be synhumanized proteins. The term "synhumanized protein" refers to a protein prepared by a method described in WO2007/019620. A synhumanized PAR4-binding protein includes a variable region of an antibody, wherein the variable region comprises FRs from a New World primate antibody variable region and CDRs from a non-New World primate antibody variable region. For example, a synhumanized PAR4-binding protein includes a variable region of an antibody, wherein the variable region comprises FWRs from a New World primate antibody variable region and CDRs from a mouse antibody, e.g., as described herein. In one example, the synhumanized PAR4-binding protein is an PAR4-binding antibody in which one or both of the variable regions are synhumanized.

The PAR4-binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898.

De-Immunized Antibodies and Proteins

The present disclosure also contemplates a de-immunized antibody or PAR4-binding protein. De-immunized antibodies have one or more epitopes, e.g., B cell epitopes or T cell epitopes removed (i.e., mutated) to thereby reduce the likelihood that a subject will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Antibody Variable Region Containing Proteins.

Single-Domain Antibodies

In some examples, a PAR4-binding protein of the disclosure is a single-domain antibody (which is used interchangeably with the term "domain antibody" or "dAb"). A single-domain antibody is a single polypeptide chain comprising all or a portion of the heavy chain variable region of an antibody. In certain example, a single-domain antibody is a human single-domain antibody (Domantis, Inc., Waltham, Mass.; see, e.g., U.S. Pat. No. 6,248,516; WO90/05144 and/or WO2004/058820).

Diabodies, Triabodies, Tetrabodies

Exemplary PAR4-binding proteins comprising an antibody antigen binding domain are diabodies, triabodies, tetrabodies and higher order protein complexes such as those described in WO98/044001 and WO94/007921.

For example, a diabody is a protein comprising two associated polypeptide chains, each polypeptide chain comprising the structure VL-X-VH or VH-X-VL, wherein VL is an antibody light chain variable region, VH is an antibody heavy chain variable region, X is a linker comprising insufficient residues to permit the VH and VL in a single polypeptide chain to associate (or form an Fv) or is absent, and wherein the VH of one polypeptide chain binds to a VL of the other polypeptide chain to form an antigen binding site, i.e., to form an Fv molecule capable of specifically binding to one or more antigens. The VL and VH can be the same in each polypeptide chain or the VL and VH can be different in each polypeptide chain so as to form a bispecific diabody (i.e., comprising two Fvs having different specificity).

Single Chain Fv (scFv) Fragments

The skilled artisan will be aware that scFvs comprise VH and VL regions in a single polypeptide chain. The polypeptide chain further comprises a polypeptide linker between the VH and VL which enables the scFv to form the desired structure for antigen binding (i.e., for the VH and VL of the single polypeptide chain to associate with one another to form a Fv). For example, the linker comprises in excess of 12 amino acid residues with (Gly$_4$Ser)$_3$ being one of the more favoured linkers for a scFv.

The present disclosure also contemplates a disulfide stabilized Fv (or diFv or dsFv), in which a single cysteine residue is introduced into a FR of VH and a FR of VL and the cysteine residues linked by a disulfide bond to yield a stable Fv (see, for example, Brinkmann et at, (1993) Proc Natl Acad Sci USA 90:547-551).

Alternatively, or in addition, the present disclosure provides a dimeric scFv, i.e., a protein comprising two scFv molecules linked by a non-covalent or covalent linkage, e.g., by a leucine zipper domain (e.g., derived from Fos or Jun) (see, for example, Kruif and Logtenberg, 1996). Alternatively, two scFvs are linked by a peptide linker of sufficient length to permit both scFvs to form and to bind to an antigen, e.g., as described in US20060263367.

For a review of scFv, see Ahmad Z A et al., (2012) Clinical and Developmental Immunology doi:10.1155/2012/980250.

Minibodies

The skilled artisan will be aware that a minibody comprises the VH and VL domains of an antibody fused to the (CH2 and/or (CH3 domain of an antibody. Optionally, the minibody comprises a hinge region between the VH and a VL, sometimes this conformation is referred to as a Flex Minibody. A minibody does not comprise a CH1 or a CL. In one example, the VH and VL domains are fused to the hinge region and the CH3 domain of an antibody. At least one of the variable regions of said minibody binds to PAR4 in the manner of the disclosure. Exemplary minibodies and methods for their production are described, for example, in WO94/09817.

Other Antibody Variable Region Containing Proteins

The present disclosure also contemplates other variable region containing PAR4-binding proteins, such as:
(i) "key and hole" bispecific proteins as described in U.S. Pat. No. 5,731,168; (ii) heteroconjugate proteins, e.g., as described in U.S. Pat. No. 4,676,980;
(iii) heteroconjugate proteins produced using a chemical cross-linker, e.g., as described in US4,676;
(iv) Fab'-SH fragments, e.g., as described in Shalaby (1992) j Exp Med 1; 175(1):217-25;
(v) single chain Fab; or
(vi) Fab3 (e.g., as described in EP 19930302894).

Non-Antibody Based Antigen Binding Domain Containing Proteins

Immunoglobulins and Immunoglobulin Fragments

An example of a compound of the present disclosure is a protein comprising a variable region of an immunoglobulin, such as a T cell receptor or a heavy chain immunoglobulin (e.g., an IgNA, a camelid antibody).

The term "immunoglobulin" will be understood to include any antigen binding protein comprising an immunoglobulin domain. Exemplary immunoglobulins are antibodies. Additional proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a VH, however lack a VL and are often referred to as heavy chain immunoglobulins. Other "immunoglobulins" include T cell receptors.

Heavy Chain Immunoglobulins

Heavy chain immunoglobulins differ structurally from many other forms of immunoglobulin (e.g., antibodies), in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain immunoglobulins are generally referred to as "VHH domains" in camelid Ig and V-NAR in IgNAR, in order to distinguish them from the heavy chain variable regions that are present in conventional 4-chain antibodies (which are referred to as "VH domains") and from the light chain variable regions that are present in conventional 4-chain antibodies (which are referred to as "VL domains").

Heavy chain immunoglobulins do not require the presence of light chains to bind with high affinity and with high specificity to a relevant antigen. This means that single domain binding fragments can be derived from heavy chain immunoglobulins, which are easy to express and are generally stable and soluble. A general description of heavy chain immunoglobulins from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

V-Like Proteins

An example of a PAR4-binding protein of the disclosure is a T-cell receptor. T cell receptors have two V-domains that combine into a structure similar to the Fv module of an antibody. Novotny et al, Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a PAR4-binding protein of the disclosure is an adnectin.

Adnectins are based on the tenth fibronectin type III (10Fn3) domain of human fibronectin in which the loop regions are altered to confer antigen binding. For example, three loops at one end of the β-sandwich of the 10Fn3 domain can be engineered to enable an Adnectin to specifically recognize an antigen. For further details see US20080139791 or WO2005/056764.

Anticalins

In a further example, a PAR4-binding protein of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a PAR4-binding protein of the disclosure is an affibody. An affibody is a scaffold derived from the Z domain (antigen binding domain) of Protein A of *Staphylococcus aureus* which can be engineered to bind to antigen. The Z domain consists of a three-helical bundle of approximately 58 amino acids. Libraries have been generated by randomization of surface residues. For further details see EP 1641818.

Avimers

In a further example, a PAR-binding protein of the disclosure is an Avimer. Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see WO2002088171.

DARPins

In a further example, a PAR4-binding protein of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two a-helices and a β-turn. They can be engineered to bind different target antigens by randomizing residues in the first a-helix and a β-turn of each repeat. Their binding interface can be increased by increasing the number of modules (a method of affinity maturation). For further details see US20040132028.

Other Non-Antibody Polypeptides

Other non-antibody proteins comprising binding domains include those based on human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins).

Constant Regions

The present disclosure encompasses PAR4-binding proteins comprising a variable region and a constant region or a domain(s) thereof, e.g., Fc, CH2 and/or CH3 domain. The skilled artisan will be aware of the meaning of the terms constant region and constant domain based on the disclosure herein and references discussed herein.

Constant region sequences useful for producing the PAR4-binding proteins of the present disclosure may be obtained from a number of different sources. In some examples, the constant region or portion thereof of the PAR4-binding protein is derived from a human antibody. Moreover, the constant domain or portion thereof may be derived from any antibody class, including IgM, IgG, IgD, IgA and IgE, and any antibody isotype, including IgGI, IgG2, IgG3 and IgG4. In one example, the human isotype IgGI is used.

A variety of constant region gene sequences are available in the form of publicly accessible deposits or the sequence thereof is available from publicly available databases. Constant regions can be selected having a particular effector function (or lacking a particular effector function) or with a particular modification to reduce immunogenicity.

In one example, a protein of the present disclosure has or displays an effector function that facilitates or enables at least partial depletion, substantial depletion or elimination of cells expressing PAR4. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

In one example, the PAR4-binding protein is capable of inducing an enhanced level of effector function.

In one example, the level of effector function induced by the constant region is enhanced relative to a wild-type Fc region of an IgG1 antibody or a wild-type Fc region of an IgG3 antibody.

In another example, the constant region is modified to increase the level of effector function it is capable of inducing compared to the constant region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect. Exemplary constant region modifications include amino acid substitutions, such as, S239D/I332E, numbered according to the EU index of Kabat or S239D/A330L/I332E, numbered according to the EU index of Kabat.

Additional amino acid substitutions that increase ability of an Fc region to induce effector function are known in the art and/or described, for example, in U.S. Pat. No. 6,737,056 or U.S. Pat. No. 7,317,091.

In one example, the glycosylation of the constant region is altered to increase its ability to induce enhanced effector function. In some examples, Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the Fnl4-binding protein in a cell line incapable of expressing a-1,6-fucosyltransferase (FUT8) (e.g., as described in Yumane-Ohnuki et ah, 2004). Other methods include the use of cell lines which inherently produce antibodies capable of inducing enhanced effector function (e.g. duck embryonic derived stem cells for the production of viral vaccines, WO2008/129058; Recombinant protein production in avian EBX® cells, WO 2008/142124).

PAR4-binding proteins can also comprise an Fc region capable of inducing enhanced levels of CDC. For example, hybrids of IgG1 and IgG3 produce antibodies having enhanced CDC activity (Natsume et at, 2008).

Methods for determining the ability of an antibody or antigen binding fragment thereof to induce effector function and known in the art and/or described herein.

In another example, the protein comprises one or more amino acid substitutions that increase the half-life of the PAR4-binding protein. For example, the PAR4-binding protein comprises a constant region comprising one or more amino acid substitutions that increase the affinity of the constant region for the neonatal Fc region (FcRn). For example, the constant region has increased affinity for FcRn at lower pH, e.g., about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half-life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784. Neutralizing PAR4-binding proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat. This position corresponds to position 228 of the hinge region according to the EU numbering system. In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgGI1 according to the numbering system of Kabat. Hinge regions of other IgG isotypes may be aligned with the IgGI1 sequence by placing the first and last cysteine residues forming inter-heavy chain disulphide (S—S) bonds in the same positions (see for example WO2010/080538).

Modified Proteins

The present disclosure provides a PAR4-binding protein having at least 80% identity to a sequence of the disclosure and having the same functional characteristics described or claimed herein.

In one example, a PAR4-binding protein of the disclosure comprises a sequence having at least 90% or 91% or 92% or 93% or 94% or 95% or 96% or 97% or 98% or 99% identity to a VL sequence disclosed herein, for example, SEQ ID NO:11.

In another example, a PAR4-binding protein of the disclosure comprises a sequence having at least 90% or 91% or 92% or 93% or 94% or 95% or 96% or 97% or 98% or 99% identity to a VH of the disclosure described herein, for example, SEQ ID NO:12.

The present disclosure also provides a nucleic acid encoding the foregoing proteins or nucleic acids that hybridize thereto under moderate to high stringency conditions.

The present disclosure also encompasses nucleic acids encoding a protein comprising a sequence set forth in SEQ ID NO:11 and SEQ ID NO:12, which differs from a sequence exemplified herein as a result of degeneracy of the genetic code.

The % identity of a nucleic acid or polypeptide is determined by GAP (Needleman and Wunsch. 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. In one example, the two sequences are aligned over their entire length.

The glycosylation pattern of an antibody may be altered from the original glycosylation pattern of the reference antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Modified glycoforms of antibodies of the present invention may be useful for a variety of purposes, including but not limited to enhancing or reducing effector function and/or modifying half-life of the antibody (see, for example, WO/2007/010401). Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260. Engineered glycoforms may be generated by any method known to one skilled in the art, for example by using engineered or variant expression strains, by co-expression with one or more enzymes, for example β(1,4)-N-acetylglucosaminyltransferase III (GnTII 1), by expressing an antibody or fragment thereof in various organisms or cell lines from various organisms, or by modifying carbohydrate(s) after the antibody or fragment has been expressed. Methods for generating engineered glycoforms are known in the art, and include but are not limited to those described in Umana et al, 1999, Nat. Biotechnol 17:176-180; Davies et al., 2007 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potelligent® technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1 191-1 195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. D. Alternatively, the antibody half-life may be increased by pegylation.

Affinity Maturation

In a further example, an existing PAR4-binding protein of the disclosure is affinity matured to produce an antibody capable of binding to PAR4 with increased affinity. For example, the sequence encoding the VL and/or VH is isolated and the CDR encoding region (e.g., the region encoding CDR3 of the VL and/or VH) is mutated such that one or more amino acid substitutions is introduced. The resulting mutant PAR4-binding protein is then screened for binding to PAR4, e.g., in a competitive assay.

The PAR4 binding proteins according to the disclosure may be soluble secreted proteins or may be presented as a fusion protein on the surface of a cell, or particle (e.g., a phage or other virus, a ribosome or a spore). Exemplary phage display methods are described, for example, in U.S. Pat. Nos. 5,821,047; 6,248,516 and 6,190,908. Phage display particles produced using these methods are then screened to identify a displayed PAR4-binding protein having a conformation sufficient for binding to a target antigen e.g., PAR4.

Protein Production

In one example, a PAR4-binding protein of the disclosure is produced by culturing a cell line, e.g., a hybridoma under conditions sufficient to produce the protein, e.g., as described herein and/or as is known in the art.

Recombinant Expression

In the case of a recombinant protein, nucleic acid encoding same is placed into one or more expression construct, e.g., expression vector(s), which is/are then transfected into host cells, such as cells that can produce a disulphide bridge or bond, such as E. coli cells, yeast cells, insect cells, or mammalian cells. Exemplary mammalian cells include simian COS cells, Chinese Hamster Ovary (CHO) cells, or myeloma cells that do not otherwise produce immunoglobulin protein. Molecular cloning techniques to achieve these ends are known in the art and described, for example in Ausubel or Sambrook. A wide variety of cloning and in vitro amplification methods are suitable for the construction of recombinant nucleic acids. Methods of producing recombinant antibodies are also known in the art. See U.S. Pat. No. 4,816,567; US7923221 and U.S. Pat. No. 7,022,500.

Following isolation, the nucleic acid encoding a protein of the disclosure is inserted into an expression construct or replicable vector for further cloning (amplification of the DNA) or for expression in a cell-free system or in cells. For example, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present disclosure. For example, a nucleic acid encoding an Fnl4-binding protein of the disclosure is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXPI-DEST and pEXP2-DEST vectors (Invitrogen).

Many vectors for expression in cells are available. The vector components generally include, but are not limited to, one or more of the following: a signal sequence, a sequence encoding Fnl4-binding protein of the present disclosure (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters include those active in prokaryotes (e.g., phoA promoter, 3-lactamase and lactose promoter systems, alkaline phosphatase, a tryptophan (trp) promoter system, and hybrid promoters such as the tac promoter).

Exemplary promoters active in mammalian cells include cytomegalovirus immediate early promoter (CMV-IE), human elongation factor 1-oc promoter (EF1), small nuclear RNA promoters (Ula and Ulb), oc-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, AUSTRALIAN CELL BANK CRL 1651); human embryonic kidney line (293 or 293 cells subcloned for growth in suspension culture; baby hamster kidney cells (BHK, AUSTRALIAN CELL BANK CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUPI promoter, the PH05 promoter, the nmt promoter, the RPR1 promoter, or the TEF1 promoter.

Means for introducing the isolated nucleic acid molecule or a gene construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation, viral transduction (e.g., using a lentivirus) and microparticle bombardment such as by using DNA-coated tungsten or gold particles (Agracetus Inc., WI, USA) amongst others.

The host cells used to produce the PAR4-binding protein of this disclosure may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

A PAR4-binding protein of the present disclosure may be isolated or purified.

Methods for purifying a PAR4-binding protein of the disclosure are known in the art and/or described herein.

When using recombinant techniques, the PAR4-binding protein of the disclosure may be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Zola (1997).

The skilled artisan will also be aware that a PAR4-binding protein of the disclosure can be modified to include a tag to facilitate purification or detection, e.g., a poly-histidine tag, e.g., a hexa-histidine tag, or an influenza virus hemagglutinin (HA) tag, or a Simian Virus 5 (V5) tag, or a FLAG tag, or a glutathione S-transferase (GST) tag. For example, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

The present disclosure also provides conjugates of PAR4-binding proteins described herein according to any example. Examples of compounds to which a protein can be conjugated are selected from the group consisting of a radioisotope, a detectable label, a therapeutic compound, a colloid, a toxin, a nucleic acid, a peptide, a protein, a compound that increases the half-life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid. A toxin includes any agent that is detrimental to (e.g., kills) cells. For a description of these classes of drugs which are known in the art, and their mechanisms of action, see Goodman et ah, (1990). Additional techniques relevant to the preparation of immunoglobulin-immunotoxin conjugates are provided in for instance in U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO93/21232.

In one example, a PAR4-binding protein as described herein according to any example is conjugated or linked to another protein for example, an immunomodulator or a half-life extending protein or a peptide or other protein that binds to serum albumin amongst others. Exemplary serum albumin binding peptides or protein are described in US20060228364 or US20080260757.

In another example, the protein is conjugated to a "receptor" (such as streptavidin) for utilization in cell pre-targeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The PAR4-binding proteins of the present disclosure can be modified to contain additional nonproteinaceous moieties that are known in the art and readily available. For example, the moieties suitable for derivatization of the protein are physiologically acceptable polymer, e.g., a water soluble polymer. Such polymers are useful for increasing stability and/or reducing clearance (e.g., by the kidney) and/or for reducing immunogenicity of an Fnl4-binding protein of the disclosure. Non-limiting examples of water soluble polymers include, but are not limited to, polyethylene glycol (PEG), polyvinyl alcohol (PVA), or propropylene glycol (PPG).

In one example, a PAR4-binding protein as described herein according to any example comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm). Alternatively, or in addition, the Fnl4-binding protein as described herein according to any example is labelled with, for example, a fluorescent semiconductor nanocrystal (as described, for example, in U.S. Pat. No. 6,306,610).

Alternatively, or in addition, the PAR4-binding protein is labelled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

Immobilized Proteins

In one example a PAR4-binding protein is immobilized on a solid or semi-solid matrix. The term "immobilization" is to be understood to involve various methods and techniques to fix proteins onto specific matrices, e.g. as described in WO99/56126 or WO02/26292. For example, immobilization can serve to stabilize the proteins so that its activity is not reduced or adversely modified by biological, chemical or physical exposure, especially during storage or in single-batch use. Various methods for immobilizing a protein on a matrix are known in the art and include crosslinking, binding to a carrier, retention within a semi-permeable matrix. Exemplary matrices include porous gels, aluminium oxide, bentonite, agarose, starch, nylon or polyacrylamide.

Assaying Activity of a Binding Protein of the Disclosure

Binding Assays

One form of such an assay is an antigen binding assay, e.g., as described in Scopes (1994) Protein Purification: principles and practice Springer-Verlag. Such a method generally involves labelling the PAR4-binding protein and contacting it with immobilized antigen or a fragment thereof, e.g., a protein comprising an extracellular portion of PAR4 fused to Biotin (e.g. as set forth in SEQ ID NO:6). Following washing to remove non-specific bound protein, the amount of label and, as a consequence, bound protein is detected. Of course, the PAR4-binding protein can be immobilized and the antigen labelled. Panning-type assays can also be used. The examples herein describe binding assays based on flag-tagged PAR4 which can be expressed on the surface of HEK cells. Inhibition of PAR4 cleavage by the PAR4-binding protein in the presence of thrombin can be measured by flow cytometry.

PAR4-binding proteins that competitively inhibit a PAR4 antibody of the invention for binding to an epitope can be screened and identified using conventional competition binding assays known in the art for example, enzyme linked immunosorbent assay (ELISA).

Competitive Binding Assays

Assays for determining an PAR4-binding protein that competitively inhibits binding of an antibody of the disclosure (e.g. mAb ARC3.H4b) will be apparent to the skilled artisan. For example, the antibody of the disclosure is conjugated to a detectable label, e.g., a fluorescent label or a radioactive label. The labelled antibody and the test PAR4-binding protein are then mixed and contacted with PAR4 or an extracellular domain thereof fused to an Fc region of an antibody or a peptide comprising an epitope thereof. The level of labelled antibody is then determined and compared to the level determined when the labelled antibody is contacted with the PAR4 or PAR4-Fc fusion or a peptide comprising an epitope thereof in the absence of the PAR4-binding protein. If the level of labelled antibody is reduced in the presence of the test PAR4-binding protein compared to the absence of the PAR4-binding protein, the PAR4-binding protein competitively inhibits binding of the antibody.

Optionally, the test PAR4-binding protein is conjugated to a different label than the antibody. This permits detection of the level of binding of the test PAR4-binding protein to the protein or epitope.

In another example, the test PAR4-binding protein is permitted to bind to PAR4 or PAR4-Fc fusion or a peptide comprising an epitope thereof prior to contacting the PAR4 or PAR4-Fc fusion or a peptide comprising an epitope thereof with an antibody described herein. A reduction in the amount of bound antibody in the presence of the PAR4-binding protein compared to in the absence of the PAR4-binding protein indicates that the PAR4-binding protein competitively inhibits binding of the antibody to PAR4. A reciprocal assay can also be performed using labelled PAR4-binding protein and first allowing the antibody to bind to PAR4 or PAR4-Fc fusion or a peptide comprising an epitope thereof. In this case, a reduced amount of labelled PAR4-binding protein bound to PAR4 or PAR4-Fc fusion or a peptide comprising an epitope thereof in the presence of the antibody compared to in the absence of antibody indicates that the PAR4-binding protein competitively inhibits binding of the antibody to PAR4.

Epitope Mapping Assays

In another example, the epitope bound by an PAR4-binding protein described herein is mapped. Epitope mapping methods will be apparent to the skilled artisan. For example, a series of overlapping peptides spanning the PAR4 sequence or a region thereof comprising an epitope of interest, e.g., peptides comprising 10-15 amino acids are produced. The PAR4-binding protein is then contacted to each peptide or a combination thereof and the peptide(s) to which it binds determined. This permits determination of peptide(s) comprising the epitope to which the PAR4-binding protein binds. If multiple non-contiguous peptides are bound by the PAR4-binding protein, the PAR4-binding protein may bind a conformational epitope.

In one example, random fragments of PAR4 are expressed on the surface of phage and the phage contacted with the PAR4-binding protein. Phage bound by the antibody can then be isolated and the amino acid sequence of the expressed peptide deduced by the encoding nucleic acid contained in the phage. By isolating a series of phage having overlapping peptides a peptide comprising a region of PAR4 comprising residues included in an epitope are identified.

Alternatively, or in addition, amino acid residues within PAR4 are mutated, e.g., by alanine scanning mutagenesis, and mutations that reduce or prevent PAR4-binding protein binding are determined. Any mutation that reduces or prevents binding of the PAR4-binding protein is likely to be within the epitope bound by the PAR4-binding protein.

A further method involves binding PAR4 or a region thereof to an immobilized PAR4-binding protein of the present disclosure and digesting the resulting complex with proteases. Peptide that remains bound to the immobilized PAR4-binding protein are then isolated and analyzed, e.g., using mass spectrometry, to determine their sequence.

A further method involves converting hydrogens in PAR4 or a region thereof to deutrons and binding the resulting protein to an immobilized PAR4-binding protein of the present disclosure. The deutrons are then converted back to hydrogen, the PAR4 or region thereof isolated, digested with enzymes and analyzed, e.g., using mass spectrometry to identify those regions comprising deutrons, which would have been protected from conversion to hydrogen by the binding of an PAR4-binding protein described herein.

In the foregoing paragraphs, reference to PAR4 encompasses recombinant PAR4, including the extracellular domain thereof.

Affinity Assays

Optionally, the dissociation constant (Kd) or association constant (Ka) or binding constant (KD, i.e., Ka/Kd) of an PAR4-binding protein for PAR4 or an epitope containing peptide thereof is determined. These constants for an PAR4-binding protein is in one example measured by a radiolabelled or fluorescently-labelled PAR4 binding assay. This assay equilibrates the PAR4-binding protein with a minimal concentration of labelled PAR4 in the presence of a titration series of unlabelled PAR4. Following washing to remove unbound PAR4, the amount of label is determined. According to another example the constants are measured by using surface plasmon resonance assays, e.g., using BIAcore surface plasmon resonance (BIAcore, Inc., Piscataway, N.J.) with immobilized PAR4 or a region thereof.

Protein Detection Assays

One example of the disclosure detects the presence of PAR4 or a cell expressing same (e.g. platelets). The amount, level or presence of a protein or cell is determined using any of a variety of techniques known to the skilled artisan such as, for example, a technique selected from the group consisting of flow cytometry, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one example the assay used to determine the amount or level of a protein is a semi-quantitative assay. In another example the assay used to determine the amount or level of a protein is a quantitative assay.

For example, the protein is detected with an immunoassay, e.g., using an assay selected from the group consisting of, immunohistochemistry, immunofluorescence, enzyme linked immunosorbent assay (ELISA), fluorescence linked immunosorbent assay (FLISA), Western blotting, radioimmunoassay (RIA), a biosensor assay, a protein chip assay and an immunostaining assay (e.g. immunofluorescence).

Standard solid-phase ELISA or FLISA formats are particularly useful in determining the concentration of a protein from a variety of samples.

In one form, an ELISA or FLISA comprises of immobilizing a PAR4-binding protein of the disclosure or a protein that binds to a different epitope of PAR4 on a solid matrix, such as, for example, a membrane, a polystyrene or polycarbonate microwell, a polystyrene or polycarbonate dipstick or a glass support. A sample is then brought into physical relation with the immobilized protein, PAR4 is bound or 'captured'. The bound PAR4 is then detected using a second labelled compound that binds to a different epitope of PAR4. Alternatively, a third labelled antibody can be used that binds the second (detecting) antibody. It will be apparent to the skilled person that the assay formats described herein are amenable to high throughput formats, such as, for example automation of screening processes or a microarray format. Furthermore, variations of the above-described assay will be apparent to those skilled in the art, such as, for example, a competitive ELISA.

In an alternative example, a polypeptide is detected within or on a cell, using methods known in the art, such as, for example, immunohistochemistry or immunofluorescence.

Methods using immunofluorescence are exemplary, as they are quantitative or at least semi-quantitative. Methods of quantitating the degree of fluorescence of a stained cell are known in the art and described, for example, in Cuello, 1984.

Biosensor devices generally employ an electrode surface in combination with current or impedance measuring elements to be integrated into a device in combination with the assay substrate (such as that described in U.S. Pat. No. 5,567,301). A PAR4-binding protein of the disclosure is incorporated onto the surface of a biosensor device and a biological sample contacted to said device. A change in the detected current or impedance by the biosensor device indicates protein binding to said PAR4-binding protein. Some forms of biosensors known in the art also rely on surface plasmon resonance (SPR) to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluids.

Binding of proteins to PAR4 can also be detected using flow cytometry as described herein in the examples.

Anti-PAR4 Antibody Generation and Selection

Alternative techniques for generating or selecting antibodies useful herein include in vitro exposure of lymphocytes to PAR4 protein or a PAR4 peptide (e.g. as described herein), and selection of antibody display libraries in phage or similar vectors (for instance, through use of immobilized or labeled PAR4 protein or peptide). Genes encoding polypeptides having potential PAR4 polypeptide binding domains can be obtained by screening random peptide libraries displayed on phage (phage display) or on bacteria, such as E. coli. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the PAR4 sequences disclosed herein to identify proteins which bind to PAR4. These "binding proteins" which interact with PAR4 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as PAR4 "antagonists" to block PAR4 binding and signal transduction in vitro and in vivo. These anti-PAR4 binding proteins would be useful for inhibiting cellular responses to protease-activated PAR4.

A variety of assays known to those skilled in the art can be utilized to detect antibodies which specifically bind to PAR4 proteins or peptides. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant PAR4 protein, polypeptide or fragment.

Assaying Functional Characteristics of PAR4 Binding Proteins

The anti-thrombotic activity of PAR-4 binding proteins across all PAR4 variants can be examined in an ex vivo platelet aggregation assays using blood from people genotyped as homozygous Ala120 or Thr120 or heterozygous in order to confirm pan-variant efficacy.

The usefulness of PAR4-binding proteins as anti-thrombotics can be examined by determining their anti-thrombotic effects in the absence and presence of inhibitors of existing anti-platelet drug pathways (aspirin (50 µM), $P2Y_{12}$ inhibitor 2-MeSAMP (50 µM or 100 µM)) and PAR1 inhibitor Vorapaxar (100 mM) are also used in the ex vivo platelet aggregation assay for comparative study of anti-thrombotic effects alongside PAR4-binding proteins. High shear conditions ($3000s^{-1}$) will be included where the inventors have shown that thrombosis occurs independently of these mechanisms (Neeves K B et al. 2008) J Thromb Haemost 6:2193-2201).

Additionally or alternatively, mouse in vivo thrombosis experiments (Lee H et al. (2012) Brit J Pharmacol 166:2188-2197; Mountford J K et al. (2015) Nat Commun 6:6535) can be used to examine functionality of PAR4-binding proteins. To ensure inclusion of a positive control for anti-PAR4 activity in these mouse experiments, one can examine the anti-thrombotic effects of antibodies generated using antigens corresponding to either the mouse and human receptor sequence (Table 2) and screened as outlined above. It should be noted that primates are the only species known to have platelets that express the combination of PAR1 and PAR4 only. Mouse platelets express PAR3 and PAR4, and only PAR4 is functional. As such, these studies are limited to in vivo proof-of-mechanism but, outside of human trials and preclinical studies in non-human primates, are the most appropriate in vivo examination of the anti-thrombotic activity of PAR4-binding proteins. Electrolytic injury of the carotid artery of anaesthetised mice can be used to examine the effects of PAR4-binding proteins on in vivo thrombus formation and stability (Lee H et al. (2012) Brit J Pharmacol 166:2188-2197; Lee H et al. (2012) Thromb Haemost 107). Blood flow is recorded using a Doppler flow probe. Endpoints can assess thrombus formation (time to artery occlusion) and stability (number and extent of recanalisation events after occlusion), as well as total blood flow through the injured artery and a thorough examination of thrombus histology by Carstair's stain of cross-sections of paraffin-embedded arteries.

PAR4 activation may be studied by determining phosphoinositide hydrolysis after protease stimulation. An epitope tagged PAR4 assay as described herein can also be used to examine cleavage and activation of PAR4 by the PAR4-binding proteins.

Mammalian cells (e.g. HEK293T cells) transfected with PAR4 constructs or PAR4 polymorphic variants are useful systems for studying antagonists of PAR4. A PAR4 transfected cell is used to screen for ligands for the receptor, as well as antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptors are selected and used within a variety of screening systems.

Cells expressing functional PAR4 are used within screening assays. A variety of suitable assays are known in the art. These assays are based on the detection of a biological response in a target cell. An increase in metabolism above a control value indicates a test compound that modulates PAR4 activity or responses. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, J. Immunol. Meth. 65:55-63, 1983). An additional assay method involves measuring the effect of a test compound on receptor (+) cells, containing the receptor of interest on their cell surface, and receptor (−) cells, those which do not express the receptor of interest. These cells can be engineered to express a reporter gene. The reporter gene is linked to a promoter element or response element that is responsive to the receptor-linked pathway, and the assay detects activation of transcription of the reporter gene. Suitable response elements include cyclic AMP response elements (CRE), hormone response elements (HRE), insulin response elements (IRE) (Nasrin et al., Proc. Natl. Acad. Sci. USA 87:5273-77, 1990), and serum response elements (SRE) (Shaw et al., Cell 56: 563-72, 1989). Cyclic AMP response elements are reviewed in Roestler et al., J. Biol. Chem. 263 (19):9063-66; 1988; and Habener, Molec. Endocrinol. 4(8):1087-94; 1990. Hormone response elements are reviewed in Beato, Cell 56:335-44; 1989. A preferred promoter element in this regard is a serum response element, or SRE (see, e.g., Shaw et al., Cell 56:563-72, 1989). A preferred such reporter gene is a luciferase gene (de Wet et al., Mol. Cell. Biol. 7:725, 1987). Expression of the luciferase gene is detected by luminescence using methods known in the art (e.g., Baumgartner et al., J. Biol. Chem. 269:29094-101, 1994; Schenborn and Goiffin, Promega Notes 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. Assays of this type will detect compounds that directly block PAR4 ligand binding, as well as compounds that block processes in the cellular pathway subsequent to receptor-ligand binding. In the alternative, compounds or other samples can be tested for direct blocking of PAR4 binding using moieties tagged with a detectable label (e.g., 125 I, biotin, horseradish peroxidase, FITC, and the like). Within assays of this type, the ability of a test sample to inhibit the activation PAR4 is indicative of inhibitory activity, which can be confirmed through secondary assays. The ability of a test sample to stimulate PAR4 activity may also be determined and confirmed through secondary assays.

An assay system that uses a ligand-binding receptor or an antibody, or a binding fragment thereof, and a commercially available biosensor instrument (BIAcore, Pharmacia Biosensor, Piscataway, N.J.) may be advantageously employed. Such receptor, antibody, or fragment is immobilized onto the surface of a receptor chip. Use of this instrument is disclosed by Karlsson, J. Immunol. Methods 145:229-40, 1991; and Cunningham and Wells, J. Mol. Biol. 234:554-63, 1993. A receptor, antibody, or fragment is covalently attached, using amine or sulfhydryl chemistry, to dextran fibers that are attached to gold film within the flow cell. A test sample is passed through the cell. If a ligand or epitope is present in the sample, it will bind to the immobilized receptor, or antibody respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, Ann. NY Acad. Sci. 51: 660-72, 1949) and calorimetric assays (Cunningham et al., Science 253:545-48, 1991; Cunningham et al., Science 245:821-25, 1991).

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored.

The PAR4-binding proteins of the disclosure can be tested in vitro for their ability to inhibit platelet aggregation induced by gamma-thrombin. Gamma-thrombin, a proteolytic product of alpha-thrombin which no longer interacts with PAR1, selectively cleaves and activates PAR4 (Soslau, G. et al, "Unique pathway of thrombin-induced platelet aggregation mediated by glycoprotein Ib", J. Biol. Chem., 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, ADP, or thromboxane analogue U46619.

Another example is an alpha-thrombin-induced platelet aggregation assay as shown herein in the examples. Alpha-thrombin activates both PAR1 and PAR4. The ability of a selective PAR4 antagonist to inhibit platelet aggregation can be measured using a standard optical aggregometer.

Another example is the tissue factor-induced platelet aggregation assay. The conditions in this assay mimic the physiological events during thrombus formation. In this assay, platelet aggregation in human PRP is initiated by the addition of tissue factor and $CaCl_2$). Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The efficacy of the PAR4 binding proteins of the present invention in preventing thrombosis can also be measured in a variety of in vivo assays. Exemplary mammals that can provide models of thrombosis and haemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, $FeCl_3$-induced carotid artery thrombosis and arteriovenous-shunt thrombosis. Models of kidney bleeding time, renal bleeding time and other bleeding time measurements can be used to assess the bleeding risk.

PAR4-binding proteins can be tested in an in vivo model of arterial thrombosis in cynolmolgus monkeys. PAR4-binding proteins can be tested in this model for their ability to inhibit thrombus formation induced by electrolytic injury of the carotid artery.

Platelet Aggregation Assays

Microplate-based platelet light transmission aggregometry can be used to measure aggregation of platelets (French et al (2016) Journal of Thrombosis and Haemostasis 14:1642-1654).

This test (Born G V (1962) Nature 194:927-929) assesses in vitro the platelet-to-platelet clump formation in a glycoprotein (GP) IIb/IIIa-dependent manner, ie, the aggregation, the most important function of platelets. The assay is based on the measurement of the increase in light transmission through the optically dense sample of platelet rich plasma (PRP) or washed platelets after the addition of the exogenous platelet agonist. During the assay, the PRP or washed platelet preparation after the addition of agonist becomes clearer because of the precipitation of platelet aggregates. This determines an increase in light transmission through the plasma sample. The device records the rate and maximal percentage of this increase from 0% (maximal optical density of PRP or washed platelets) to 100% (no optical density of autologous platelet-poor plasma or Tyrodes buffer, respectively) by a photometer. This signal is converted automatically in a graphic curve that parallels the increase in light transmission during the platelet aggregation. The available aggregometers are easy-to-use devices equipped with automatic setting (100% and 0%), software for storing results and disposable cuvettes with a stirring bar. The slope of the curve, the maximal extent of aggregation (%), and the latency time (lag phase) are the parameters automatically measured, and the shape change and primary and secondary aggregation may be seen graphically. To the PRP or washed platelet sample, different agonists are added to stimulate different platelet activation pathways, obtaining information about the several features of platelet function. Born's platelet aggregometry is the most widely employed methodology for detecting platelet function disorders and monitoring antiplatelet therapies.

In vivo analysis of platelet function after administration of the PAR4-binding protein can be determined using bleeding time (BT) (Duke W W et al (1910) JAMA 55:1185-1192). BT assesses the platelet ability to develop a haemostatic plug by recording the time that the platelets take to occlude an in vivo skin wound for stopping the haemorrhage.

Impedance whole blood aggregometry (WBA) allows one to assess platelet function by using the anticoagulated whole blood (WB) as milieu without any sample processing (Mackie I J, et al. (1984) J Clin Pathol. 37:874-878). It is based on the principle that activated platelets stick via their surface receptors to artificial surfaces of two electrodes within the WB sample positioned at a determined distance between them. Platelet aggregation is assessed by detecting the increase in electrical impedance generated by the aggregation of other platelets upon those fixed to the electrodes. Hence, by diminishing the current intensity, the electrical impedance increases. The degree of the increase in impedance is recorded in Ohms.

Lumiaggregometry allows simultaneous measurement of the release of adenine nucleotides from platelet granules and platelet aggregation (Holmsen H, et al. (1966) Anal Biochem. 17:456-47). The method is based on the evaluation of adenosine triphosphate (ATP) released from activated platelets by different agonists by using a luminescence technique in PRP, washed platelets (WP), or WB. The assay is based on the conversion of ADP, released from the platelet dense granules, to ATP that reacts with the luciferin-luciferase reagent. The light emitted, proportional to the ATP concentration, is quantified by the lumi-aggregometer.

Additional platelet function tests are reviewed in Paniccia R et al (2015) Vasc Health Risk Manag. 11:133-148.

Calcium Signalling Assays

Calcium flux can be measured in isolated platelets with a dual-dye ratiometric microimaging assay (Nesbitt W S et al. (2012) Methods Mol Biol 788:73-89).

Animal Models

In vivo animal models of thrombosis may be utilized by the skilled artisan to further or additionally screen, assess, and/or verify the antibodies or fragments thereof of the present disclosure, including further assessing PAR4 activation or anti-thrombotic effects in vivo. Such animal models include, but are not limited to models subject to electrolytic injury of the carotid artery and whereby thrombus formation (time to artery occlusion) and stability (number and extent of recanalization events after occlusion) and total blood flow through the injured artery are examined.

An exemplary or suitable mouse model is the PAR4−/− mouse (Sambrano G R et al. (2001) Nature 2000 407:258-64; Mao Y et. al. (2010) J Cereb Blood Flow Metab. 30(5):1044-1052).

Pharmaceutical Compositions

PAR4-binding proteins of the disclosure (syn. active ingredients) are useful for formulations into a pharmaceutical composition for parenteral, topical, oral, or local administration, aerosol administration, or transdermal administration, for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges.

The pharmaceutical compositions of this disclosure are useful for parenteral administration, such as intravenous administration or subcutaneous administration.

The compositions for administration will commonly comprise a solution of the PAR4-binding protein of the disclosure dissolved in a pharmaceutically acceptable carrier, such as an aqueous carrier. A variety of aqueous carriers can be used, e.g., buffered saline and the like. The compositions may contain pharmaceutically acceptable carriers as required to approximate physiological conditions such as pH adjusting and buffering agents, toxicity adjusting agents and the like, for example, sodium acetate, sodium chloride, potassium chloride, calcium chloride, sodium lactate and the like. The concentration of PAR4 binding proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Non-aqueous vehicles such as mixed oils and ethyl oleate may also be used. Liposomes may also be used as carriers. The vehicles may contain minor amounts of additives that enhance isotonicity and chemical stability, e.g., buffers and preservatives.

The PAR4-binding protein of the disclosure can be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains the compounds of the present disclosure as an active ingredient will be known to those of skill in the art.

Suitable pharmaceutical compositions in accordance with the disclosure will generally include an amount of the PAR4-binding protein of the present disclosure admixed with an acceptable pharmaceutical carrier, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980.

Upon formulation, compounds of the present disclosure will be administered in a manner compatible with the dosage formulation and in such amount as is therapeutically/prophylactically effective. Suitable dosages of compounds of the present disclosure will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage.

Exemplary dosages and timings of administration will be apparent to the skilled artisan based on the disclosure herein. The preferred dose of the PAR4 antagonist is a biologically active dose. A biologically active dose is a dose that will inhibit cleavage and/or signalling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis. Alternatively, the biological activity of PAR4 is measured by assessing cellular signalling elicited by PAR4 (e.g., calcium mobilization or other second messenger assays).

In some examples, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

In some examples liposomes and/or nanoparticles may also be employed with the PAR4-binding protein. The formation and use of liposomes is generally known to those of skill in the art. Liposomes can be formed from phospholipids that are dispersed in an aqueous medium and spontaneously form multilamellar concentric bilayer vesicles (also termed multilamellarvesicles (MLVs)). MLVs can generally have diameters of from 25 nm to 4 μm. Sonication of MLVs results in the formation of small unilamellar vesicles (SUVs) with diameters in the range of 200 to 500 angstrom, containing an aqueous solution in the core. Phospholipids can form a variety of structures other than liposomes when dispersed in water, depending on the molar ration of lipid to water. At low ratios the liposome is the preferred structure.

The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state.

The composition may be administered alone or in combination with other treatments, therapeutics or agents, either simultaneously or sequentially including, but not limited to:

(i) Anticoagulant agents e.g. FXa inhibitors, FXIa inhibitors such as apixaban or rivaroxaban, or thrombin inhibitors such as dabigatran;

(ii) Antiplatelet agents e.g. asprin or P2Y12 antagonist such as clopidogrel, ticagrelor, or prasugrel;

(iii) Vascularisation agents e.g. angiogenesis inhibitors.

Methods of Treatment

As discussed herein, the PAR4-binding proteins of the disclosure can be used for treating, preventing or ameliorating thrombosis or a thromboembolic disorder in a subject.

Thrombosis refers to formation or presence of a thrombus (pl. thrombi) within a blood vessel that can cause ischemia or infarction of tissues supplied by the vessel.

Thromboembolic disorders are characterised by a sudden blocking of an artery by a clot (e.g. embolism) or foreign material that has been brought to its site of lodgement by the blood current. A "thromboembolism,", refers to obstruction of a blood vessel with thrombotic material carried by the blood stream from the site of origin to plug another vessel. The term "thromboembolic disorders" entails both "thrombotic" and "embolic" disorders (defined above).

Thromboembolic disorders include arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and haemodialysis. In another embodiment, the term "thromboembolic disorders" includes acute coronary syndrome, stroke, deep vein thrombosis, and pulmonary embolism.

The term "stroke", as used herein, refers to embolic stroke or atherothrombotic stroke arising from occlusive thrombosis in the carotid communis, carotid interna, or intracerebral arteries.

Kits

The present disclosure also provides therapeutic/prophylactic/diagnostic kits comprising compounds of the present disclosure for use in the present detection/diagnostic/prognostic/treatment/prophylactic methods. Such kits will generally contain, in suitable container means, a PAR4-binding protein of the present disclosure. The kits may also contain other compounds, e.g., for detection/isolation/diagnosis/imaging or combined therapy. For example, such kits may contain any one or more of a range of anti-coagulation or anti-platelet agents.

In one example, the kit is for the treatment or prevention of a condition. In such kits, the PAR4-binding protein may be provided in solution or in a lyophilized form, optionally with a solution for resuspension. The PAR4-binding protein may be conjugated to a therapeutic compound or the kit may include a therapeutic compound for conjugation thereto.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

The present invention is described further in the following non-limiting examples.

EXAMPLES

Methods

Generation of Antibodies

Anti-PAR4 monoclonal antibodies were produced by immunisation of HumAb mice (Regeneron Pharmaceuticals) with C-terminal KLH (keyhole limpet hemocyanin) conjugated peptides as described in Table 2 below. The immunising peptides correspond to the N-terminal thrombin cleavage and activation site of hPAR4 (SEQ ID NO:2). The cleavage site is indicted by RG as shown in the underlining in the below sequence of human PAR4:

GDDSTPSILPAP<u>RG</u>YPGQVC (SEQ ID NO:2)

Screening was Performed Against Naked Peptide (SEQ ID NO:3).

Mice were immunised intraperitoneally three times at two week intervals with a combination of 16 μg of antigen and immune adjuvant (Sigma Aldrich cat #56322) in combination with methylated CpG. A serum sample was collected form the immunised mice and reactivity to the antigen was tested by ELISA at a dilution of 1:250 and 1:1250 and compared to a pre-immunisation sample. Serum titre difference pre-immune to post-immune at 1:250 and 1:1250 was required to be greater than 3-fold increase.

The mouse with the highest titre was selected for fusion.

Immunising Peptides

Immunising peptides and SKB labelled peptides (as shown in Table 2) were synthesised by Auspep, Melbourne, Australia using solid-phase synthesis.

Biotin was attached to the peptides (see Table 2) at the C-terminus using a serine (S) and lysine (K) linker (SK). Biotin was added by chemical conjugation to the C-terminal lysine residue thus generating SKB as shown in Table 2.

Mice were immunised with human PAR4 keyhole limpet hemocyanin (KLH) peptide having the sequence GDDSTP-SILPAPRGYPGQVC-KLH (SEQ ID NO: 4).

Hybridoma Expansion

To generate hybridoma cells, the mouse spleen was excised, dissociated into a single cell suspension and fused to Sp2/0-Ag14 myeloma cells using polyethylene glycol.

The resultant hybridoma cells were grown in Azaserine Hypoxantine containing medium in 20×96 well tissue culture plates.

Hybridoma colonies were grown for 10 days at which point the number of hybridoma colonies (represented as fusion efficiency) was determined and after a further 3 days incubation an aliquot of antibody supernatant taken for screening. The supernatant was assayed for reactivity to the antigen and any screening samples, firstly by microarray followed by ELISA of any IgG positive clones.

The highest responding ELISA positive clones were then expanded into a 24 well tissue culture plate for 3-4 days at which point they were expanded to a 6 well tissue culture plate. The cells were seeded at a 1:5 (supernatant wells) and 1:25 (cells wells) ratio. Once the cell wells reached 80% confluence the cells were extracted and frozen in liquid nitrogen in 10% DMSO and the supernatant from the supernatant wells was pooled and frozen at −20° C.

Clones selected for sub-cloning were subjected to at least 2 rounds of serial dilution. After each dilution stage, cells were grown for 4-5 days and single colonies producing antibody positive to the antigen were determined by supernatant ELISA and the top clones were expanded for further rounds. The final monoclonal cell-lines were expanded into 6-well cell-culture plates for 4-5 days, the supernatant was extracted and frozen down along with the cells.

The supernatant of sub-cloned cell-lines are tested by a commercially available assay kit to determine the isotype of the monoclonal antibody being produced.

Microarray Assay

Screening of hybridoma supernatants by micro-array was performed according to standards techniques.

ELISA Screening of Monoclonal Antibodies 96-well ELISA plates were coated with 50 µl of antigen diluted to a concentration of 4 µg/ml in coating buffer (0.1M Sodium Hydrogen Carbonate ($NaHCO_3$) (Merck, #1.06329.0500)). Plates were incubated overnight at 4° C.

Wells were then washed with an automated plate washer (300 µl 1×PBS, 3 times). The wells were blocked with 200 µl of blocking buffer (3% BSA/1×PBS (BSA: (Sigma, #1001647742)) for 1 hour at room temperature followed by washing as above.

50 µl of undiluted hybridoma cell culture supernatant was added into appropriate wells and incubated at room temperature for 1 hour followed by washing as above. The secondary antibody (Alkaline Phosphatase-conjugated AffiniPure Goat Anti-Mouse IgG (H+L) (Jackson ImmunoResearch Laboratories, Inc. #115-055-003)) was diluted 1:1000 in 1×PBS (8% Sodium Chloride (NaCl, Merck #1.06404.5000), 0.2% Potassium Chloride (KCl, Merck #1.04936.0500), 1.44% di-Sodium hydrogen phosphate (Na2HPO4, Merck #1.06586.0500), 0.24% Potassium dihydrogen orthophosphate ($KH_2PO_4$, Merck #1.04873.0500)) and 50 µl of diluted antibody added to each well and incubated for 1 hour at room temperature. Wells were washed as above. A set of substrate tablets (1×silver, 1×gold) into 20 ml of dd$H_2O$ by shaking vigorously on the thermomixer for 6 mins at room temperature. 50 µl of substrate (SIGMAFAST™ p-Nitrophenyl phosphate Tablets (Sigma-Aldrich, N2770-50SET)) was added into each well and incubated for 20-25 mins at room temperature. 50 µl of STOP solution (2M Sodium Hydroxide, Solid (NaOH) (Merck, Cas #1310-73-2)) was added into each well to stop the reaction. Absorbance was read at 405 nm immediately after adding STOP solution with the ELISA reader, using the 'RdrOle4' software.

Human Blood Samples

Blood was collected after informed consent had been obtained from healthy adults (aged 21-50 years of both sexes) who had not taken anti-platelet medications in the past 10 days. Blood was drawn from the antecubital vein with a 19-guage butterfly needle into syringes containing either one-seventh volume acid citrate dextrose (ACD)(7:1 v/v final concentration) for platelet isolation, or one-tenth volume trisodium citrate (0.32% w/v final concentration) for whole blood flow experiments as previously described (Mountford J K et al (2015) Nat Commun 6:6535).

Mice

HumAb mice (Murphy A J et al. (2014) Proc Natl Acad Sci USA 111:5153-5158) were obtained from Regeneron Pharmaceuticals. HumAb mice have been genetically engineered to allow for generation of human antibody responses by replacing a 3 Mb segment of the mouse heavy and K light variable Ig loci with their human counterparts (Murphy A J et al. (2014) Proc Natl Acad Sci USA 111:5153-5158). The HumAb mice exhibit normal variable segment rearrangement, somatic hypermutation, and class switching and demonstrate a robust humoral response yielding a large diversity of monoclonal antibodies and is the platform used by Regeneron to produce fully-human monoclonal antibodies against a range of targets.

Detection of PAR4 by Flow Cytometry

Human or mouse washed platelets ($5 \times 10^7$/mL) were incubated with anti-PAR4 antibody (0.1 mg/ml) for 30 mins at 37° C. and then fixed with paraformaldehyde 1% v/v final concentration). The suspension was then centrifuged at 1000×g for 2 min to obtain the platelet pellet, which was then resuspended in modified Tyrode's buffer (12 mM $NaHCO_3$, 10 mM HEPES pH 7.4, 137 mM NaCl, 2.7 mM KCl, 5.5 mM D-glucose, 1 mM $CaCl_2$)) containing a 1:50 dilution of an FITC-conjugated anti-rabbit IgG. After 30 mins at room temperature, the samples were centrifuged again, and the platelet pellet was resuspended in modified Tyrode's buffer an analysed by use of a flow cytometer (FACSCalibur, BD Biosciences).

PAR4 Thrombin Cleavage Assay $1 \times 10^6$ HEK293T cells (in Dulbecco's modified eagle's medium+10% foetal calf serum) were seeded onto 12-well plates 24 hours before transfection. When confluent, they were transiently transfected with 1 µg of DNA from one of the PAR4 variants (expression vectors pBJ-FLAG-PAR4-120A-296F or pBJ-FLAG-PAR4-120T-296F; Edelstein et al (2014) Blood 124(23):3450-8) plus 4 µL of Lipofectamine 2000, as per manufacturer's instructions. Forty-eight hours after transfection, cells were harvested and washed twice with PBS, then resuspended to a count of $1 \times 10^6$/mL. Cells (50 µL assays/$0.5 \times 10^5$ cells per condition) were then pre-treated with either 1, 10 or 100 µg/mL of 5RC3 or sub-clone 5A.RC3.F10b.H4b or 100 µg/mL matched Isotype control (mouse IgG1) for 15 minutes at 37° C. Cells were then stimulated with 2 U/mL of thrombin for 10 minutes. The reaction was stopped by the addition of 4 U/mL hirudin. Cells were then washed once and resuspended with PBS containing a 1:200 dilution of FITC anti-FLAG antibody (Sigma, clone M2) and incubated for 1 hour at room temperature in the dark. Cells were then fixed with 1% paraformaldehyde (final concentration) and read on a FACSCalibur flow cytometer to determine % of FL1/FITC-Positive events. Data were normalised against the resting sample (100%, no thrombin treatment).

Surface Plasmon Resonance (SPR) Assay

Surface Plasmon Resonance (SPR) is a biosensor technology enabling label-free and real-time measurement of protein-protein interactions. The SPR binding analysis of proteins and antibodies was performed using a Bio-Rad ProteOn XPR36 array system or a Biacore T200 (GE system) by standard techniques.

Method to Determine Kinetics of 5A.RC3

ProteOn is a SPR biosensor with a multichannel module and interaction array sensor chip for the analysis of up to 36 protein interactions in a single injection step. Analysis was performed using a ProteOn NLC biosensor chips, which contains a surface consisting of NeutrAvidin bound to the alginate polymer for capture of biotinylated proteins and peptides.

The NLC chip was conditioned with 50 mM NaOH, followed by 1M NaCl, both at a flow rate of 30 µl/minute. Conditioning was performed in both the horizontal and vertical directions (channels). Biotinylated peptides, (ligand samples), at a concentration of 25 µg/ml were captured on the chip in the vertical channels at a flow rate of 30 µl/minute (see Table 1 for ligand sample set up on the biosensor chip). Running buffer, (1×PBS, 0.005% Tween, pH7.4), was injected across the vertical channels to ensure the stable capture of peptide ligands before injection of analyte. The chip was then rotated horizontally and a dilution series of mAb5ARC3.F10b.H4b (analyte), was injected across channels A1-A6 at a flow rate of 100 µl/minute (see Table 1 for analyte concentrations tested). Note: The mAb concentration of 6.25 nM was omitted from the final analysis as it was giving higher than normal readings.

TABLE 1

Sample set-up on NLC biosensor chip

| | | Analyte (mAb5RC3.H4b mAb) | | | | | |
|---|---|---|---|---|---|---|---|
| | | A1 | A2 | A3 | A4 | A5 | A6 |
| Lane | Ligand | 100 nM | 50 nM | 25 nm | 12.5 nM | 6.25 nM | 0 nM |
| L1 | Human PAR1 peptide* | | | | | | |
| L2 | Human PAR2 peptide* | | | | | | |
| L3 | Human PAR3 peptide* | | | | | | |
| L4 | Human PAR4 peptide* | | | | | | |
| L5 | Blank (running buffer) | | | | | | |
| L6 | Unrelated peptide* | | | | | | |

*All peptides are biotinylated

Method to Determine Kinetics of Purified Anti-h PAR4 mAbs to hPAR4

Biacore analysis was performed on a Biacore T200 using two different methods either an anti-mouse Fc capture approach or using a similar method as described above using the ProteoOn system.

Antibody Capture Method

A series S CM5 sensor chip was activated with standard EDC/NHS amine coupling chemistry using the manufacturers recommended protocol with Goat anti-mouse IgG Fc. Anti-hPAR4 mAbs were captured at 1-2 ug/ml for 2 minutes at 10 ul/minute on flow cell 2 (FC2) and flow cell 1 (FC1) was used as a reference channel. Dilutions of hPAR4 peptide were prepared in running buffer (10 mM HEPES, 150 mM NaCl, 3 mM EDTA, 0.005% Tween 20 with 0.1% BSA) typically 1000, 500, 250, 125, 62.5 nM and flowed over both FC1 and 2 for 60-100 seconds at 30 ul/minute and dissociation was monitored for 80-120 seconds. Blank injections of buffer alone were also performed. All injections were performed in duplicate and in a random order. After each capture/injection/dissociation cycle the chip was regenerated with a 30 second injection of 0.1M Glycine pH2.0.

Streptavidin Capture Method

A series S sensor chip SA was conditioned using the manufacturers recommended protocol and immobilised with 1 ug/ml hPAR4-biotinylated peptide on FC2 and hPAR1-biotinylated peptide as a control onto FC1. Dilutions of anti-hPAR4 mAbs were prepared in running buffer typically 10, 5, 2.5, 1.25, 6.25 and 0 nM and flowed over both FC1 and 2 for 60 seconds at a flow rate of 100 ul/minute and dissociation was monitored for 200 seconds. Blank injections of buffer alone were also performed. All injections were performed in duplicate and in a random order. After each capture/injection/dissociation cycle the chip was regenerated with a 30 second injection of 0.1M Glycine pH2.0.

Platelet Aggregation Assay

Platelet aggregation was measured by light transmission aggregometry in a 96-well plate format. Human isolated platelets ($2 \times 10^8$/ml) were pre-treated for 10 mins at 37° C. with dimethylsulfoxide (DMSO) (1% v/v), the PAR1 antagonist vorapaxar (90 nM), the anti-PAR4 antibody 5RC3 (20-100 µg/ml), or a combination of vorapaxar and 5RC3. Platelets were treated with one of thrombin (0.1 U/ml) and aggregation was analysed at 37° C. in a FLUOstar OPTIMA plate reader (BMG Labtech) using a 595 nm excitation filter, for a period of 50 min (10 read cycles with 5 min double orbital shake period between each read). Optical density was normalised against the blank (maximum) and unstimulated platelets (minimum) and expressed as % maximum.

Whole Blood Thrombosis Assay

Human whole blood collected in citrate (3.2%) was pre-incubated for 15 min at 37° C. with PE-conjugated anti-CD9 antibody (4 µg/mL) and an anti-fibrin antibody (5 µg/ml), and one of hirudin (800 U/ml), DMSO (1% v/v), PAR-1 antagonist E5555 (1 µM), anti-PAR4 antibody (0.2 mg/ml) or the combination of both PAR inhibitors. Whole blood was re-calcified with 5-7.5 mM $CaCl_2$) (final concentration) to initiate coagulation, and drawn over glass microslides (1×0.1 mm internal diameter) coated with bovine type 1 collagen (250 µg/ml) at a fixed flow rate of 0.06 ml/min, resulting in a wall shear rate of 600 $s^{-1}$. Dual colour confocal fluorescence images were recorded at 488 and 561 nm excitation, collected through a 40× water immersion objective. Confocal z-stacks were continuously recorded for 2 min before modified, calcium-free Tyrode's buffer was flowed over the thrombi and z-stacks encompassing the entire height of the thrombus field were recorded over a period of 10 min. Platelet thrombi were defined using anti-CD9-PE and fibrin volume was quantified using average fluorescence of the thrombus field. Data were normalised against the hirudin baseline and expressed as a percentage of the control.

PCR-Based SNP Genotyping Assay for PAR4 SNP

Genomic DNA (gDNA) was extracted from the buffy coat of human whole blood using the QIAamp Blood Kit—Mini, according to the manufacturer's instructions. DNA samples were genotyped for rs773902 using a Taqman SNP Genotyping Assay (Life Technologies, Carlsbad, Calif., USA), according to manufacture instructions using 10 ng DNA. The PCR was performed on a Roche 96-well plate lightcycler, using the following thermal cycling conditions; 95° C. for 15 s, 60° C. for 60 s, repeated for 40 cycles. Endpoint genotyping analysis using (Mygo Pro) software was used to discrimination between alleles, using ratiometric analysis of the relative fluorescence signal accumulated at 465-510 nm ("A" allele)/533-580 nm ("T" allele).

Statistical Analysis

Statistical analysis was performed with GRAPHPAD PRISM (version 6.0, La Jolla, Calif., USA). Significance was defined at P<0.05 as determined with either an unpaired, two-tailed Student's t-test or one-way ANOCA with Fisher's LSD test for multiple comparisons.

Nomenclature of Antibodies

Unless, indicated to the contrary, the following nomenclature will be used to refer to the antibodies referred to herein as indicated in Table 2 below. Short-hand reference to, for example, 5A.RC3 refers to the monoclonal antibody sub-clone 5A.RC3.F10b.H4b unless indicated to the contrary.

TABLE 2

Antibody nomenclature

| Monoclonal antibody | Clonal (full name) | Isotype | SEQ ID Nos H and L chains |
|---|---|---|---|
| 5A.RC3 | 5A.RC3.F10b.H4b | IgG2a/K | 11 and 12 |
| 5D.RH4 | 5D.RH4.G7.E6.C7b.G7 | IgG2a/K | 89 and 90 |
| 5H.RA3 | 5H.RA3.D3b.A2b | IgG2a/K | 97 and 98 |
| 5F.RF3 | 5F.RF3.A7b.C9 | IgG2b/K | 22 and 23 |
| 5G.RA1 | 5G.RA1.E10.G3 | IgG2a/K | 53 and 54 |
| 5I.RG1 | 5I.RG1.D6.C1b | IgG3/K | 45 and 46 |
| 5H.RF2 | 5H.RF2.A5b.D3.C2 | IgG2a/K | 107 and 108 |
| 5H.RD2 | 5H.RD2.A7b | IgG1/K | 32 and 33 |
| 5H.RH4 | 5H RH4.C8b.A3.A6 | IgG2b/K | 91 and 92 |
| 5G.RF6 | 5G RF6.B10.E3 | IgG2a/K | 93 and 94 |
| 5G.RD6 | 5G RD6.D1.E11b | IgG2a/K | 95 and 96 |
| 5G.RG1 | 5G RG1.D3.C2b | IgG1/K | 99 and 100 |
| 5F.RE6 | 5F RE6.D3.E7 | IgG2a/K | 105 and 106 |

Example 1 Development of Antagonist Monoclonal Antibodies to Human PAR4

The inventors sought to develop monoclonal antibodies targeting human PAR4. Antibody production and screening was performed at the Monash Antibody Technology Facility (MATF) by its Director, Prof Mark Sleeman, using Regeneron Pharmaceuticals' proprietary HumAb mice (VelocImmune®) to produce high affinity antibodies to PAR4 as described in further detail below.

(i) Immunisation

KLH conjugated peptides of the N-terminal thrombin cleavage and activation site of human PAR4 (hPAR4) were generated and used to immunise HumAb mice followed by three booster immunisations according to standard protocols. Sera titre was determined by ELISA using naked hPAR4 peptides (Table 3).

Three separate immunisation programs of a total of 12 HumAb mice with the peptides were undertaken. The sequences of the peptides used for immunisation are shown in Table 3 and contained in some cases an additional C-terminal cysteine (as indicated by underlining). The peptides were conjugated at their C-terminus to keyhole limpet hemocyanin (KLH) or via a cysteine-lysine to biotin (SKB).

TABLE 3

Peptides used as immunogen and for screening and Surface plasmon resonance (SPR)

| Name | Use | Sequence |
|---|---|---|
| hPAR4 (KLH) | Immunogen | GDDSTP SILPAPRGYP GQVC KLH (SEQ ID NO: 4) |
| hPAR4 (naked) | + screen | GDDSTP SILPAPRGYP GQVC (SEQ ID NO: 2) |
| mPAR4 (KLH) | Immunogen | LKEP KSSDKPNPRGYPGKFC KLH (SEQ ID NO: 5) |
| mPAR4 (naked) | + screen | LKEP KSSDKPNPRGYPGKFC (SEQ ID NO: 3) |
| mPAR4 (Biotin) | + screen, SPR | LKEP KSSDKPNPRGYPGKFC-GGGGSKB (SEQ ID NO: 6) |
| hPAR4 (Biotin) | + screen, SPR | GDDSTP SILPAPRGYP GQVC-GGGGSKB (SEQ ID NO: 7) |
| hPAR3 (Biotin) | − screen, SPR | AKPTLPIKTF RGAPPNSF-GGGGSKB (SEQ ID NO: 8) |
| hPAR2 (Biotin) | − screen, SPR | SCSGTIQGTN RSSKGRSL-GGGGSKB (SEQ ID NO: 9) |
| hPAR1 (Biotin) | − screen, SPR | SKATNATLDP RSFLLRNP-GGGGSKB (SEQ ID NO: 10) |

The sequence of the thrombin cleavage site (RG) is shown in bold (no underlining).

(ii) Hybridoma Generation

Fusion was performed with SP2/O Ag14 as a fusion partner using standard fusion protocols (Yokoyama, W. Production of monoclonal antibodies. In: Coligan J, Kruisbeek A, Marguiles D, Shevach E M, Strober W., editors. Current Protocols in Immunology. Vol. 1. New York, N.Y: John Wiley & Sons; 1994. pp. 2.5.2-2.5.17.) and plated on twenty 96-well plates. Cells were grown in medium containing HAT as a selection marker.

TABLE 2-continued

Antibody nomenclature

| Monoclonal antibody | Clonal (full name) | Isotype | SEQ ID Nos H and L chains |
|---|---|---|---|
| 5H.RG4 | 5H RG4.H7b.F5b | IgG2a/K | 101 and 102 |
| 5G.RC5 | 5G RC5.F2.H6 | IgG3/K | 103 and 104 |

Hybridomas were expanded in RPMI-1640 medium supplemented with 10% fetal bovine serum, 50 μM beta-mercaptoethanol and 1 mM sodium pyruvate.

(iii) Screening of Hybridoma Clones

The inventors screened thousands of hybridoma supernatants for high affinity specific antigen-positive lines. The monoclonal antibodies comprise human Ig variable regions linked to mouse constant regions (hence are designated 'mAb' herein to refer to such chimeric antibodies).

Figure 2:
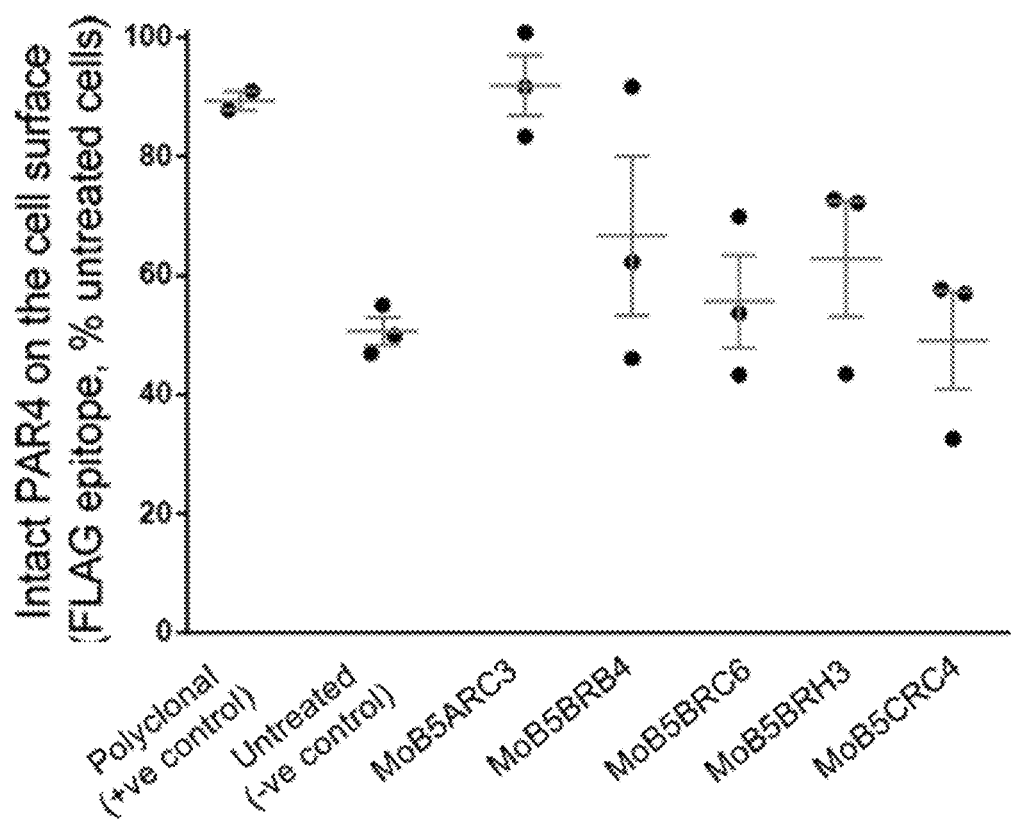
FIG. 2 shows the percentage of intact PAR4 present on the cell surface of HEK293 cells transfected with human PAR4 containing an N-terminal FLAG tag as quantified by flow cytometry. The cells were pre-treated with five different hybridoma supernatants obtained from a first hybridoma screen (MoB5ARC3, MoB5BRB4, MoB5BRC6, MoB5BBRH3 and MoB5CRC4) prior to treatment with thrombin (2 U/ml for 10 mins). Positive control was an polyclonal anti-PAR4 antibody (French et al (2016) Journal of Thrombosis and Haemostasis 14:1642-1654). Data are mean±standard error of the mean for three individual data points.

Hybridoma supernatants were initially screened for binding to the immunising PAR4 peptide sequence (GDDSTPSILPAPRGYPGQVC-KLH (SEQ ID NO: 4)) by antigen microarray, with binding determined by fluorescence intensity signal over background (signal from medium alone). The top-ranked 46 clones per splenic fusion were selected for further ELISA-based screening for binding to the PAR4 antigen (both native and KLH-linked; fold binding, native vs KLH-linked PAR4 peptide). Clones that exhibited >3-fold binding to the native PAR4 peptide over the KLH-linked PAR4 peptide were selected for similar ELISA-based screening for specificity (binding to native PAR4 peptide versus peptides corresponding to equivalent regions in PAR1 (SKATNATLDPRSFLLRNP (SEQ ID NO: 115)), PAR2 (SCSGTIQGTNRSSKGRSL (SEQ ID NO: 116)), and PAR3 (SCSGTIQGTNRSSKGRSL (SEQ ID NO: 117); fold binding PAR4 vs PAR1, 2 or 3 peptide). Clones that exhibited >3-fold binding to the PAR4 peptide over the other PAR peptides were expanded and tested in functional bioassays (inhibition of PAR4 cleavage and inhibition of PAR4-induced platelet activation/aggregation) (FIGS. 2 and 12).

Clones that exhibited both binding and function were selected for sub-cloning and re-testing. After each round of sub-cloning, clones were again tested for binding to native PAR4 peptide (vs media alone) by ELISA in order to confirm maintenance of the binding antibody in the clone.

TABLE 3

PAR4 clones first screening

| Series | clone | Fold binding native vs KLH-linked PAR4 peptide | Sub-clone (first) | Fold binding native vs KLH-linked PAR4 peptide | Fold binding PAR4 vs PAR 1, 2 or 3 | Sub-clone (second) | Fold binding native vs KLH-linked PAR4 peptide | Binding to PAR4 ratio | Binding to PAR3 ratio | Binding to PAR2 ratio | Binding to PAR1 ratio | Functional screen on hybridoma supernatants that exhibited binding# |
|---|---|---|---|---|---|---|---|---|---|---|---|---|
| MOB5AR | C3 | 19.9 | A2b | 17.6 | 19.8 | | | | | | | Yes |
| | | | F2b | 17.4 | 18.2 | | | | | | | ND |
| | | | F3b | 19.4 | 119.2 | | | | | | | ND |
| | | | G3b | 19.7 | 20.0 | | | | | | | ND |
| | | | C6b | 20.4 | 19.1 | | | | | | | ND |
| | | | C8b | 15.4 | 16.6 | | | | | | | ND |
| | | | B9b | 15.0 | 15.2 | | | | | | | ND |
| | | | D9b | 16.0 | 16.4 | | | | | | | ND |
| | | | H9b | 15.7 | 16.8 | | | | | | | ND |
| | | | F10b | 17.1 | 18.6 | E1b | 21.1 | 16.8 | 1.0 | 1.0 | 1.3 | ND |
| | | | | | | H1b | 20.2 | 16.5 | 1.0 | 1.0 | 1.1 | ND |
| | | | | | | B2b | 20.4 | 13.4 | 1.2 | 1.0 | 1.1 | ND |
| | | | | | | F2b | 19.5 | 17.2 | 1.2 | 1.2 | 1.1 | ND |
| | | | | | | H2b | 19.5 | 15.4 | 1.1 | 1.1 | 1.1 | ND |
| | | | | | | G3b | 18.7 | 14.6 | 1.1 | 1.0 | 1.2 | ND |
| | | | | | | B4b | 19.1 | 15.4 | 1.0 | 1.1 | 1.2 | ND |
| | | | | | | F4b | 19.1 | 14.6 | 1.1 | 1.0 | 1.1 | ND |
| | | | | | | G4b | 19.6 | 15.4 | 1.1 | 1.1 | 1.3 | ND |
| | | | | | | H4b^ | 19.3 | 15.2 | 1.1 | 1.0 | 1.0 | ND |
| | | | | | | B6b | 20.1 | 15.4 | 1.1 | 1.0 | 1.1 | ND |
| | | | | | | C6b | 17.6 | 16.6 | 1.1 | 1.1 | 1.2 | ND |
| | | | | | | G7b | 17.4 | 15.5 | 1.1 | 1.0 | 1.1 | ND |
| | | | | | | H7b | 16.4 | 16.0 | 1.0 | 1.1 | 1.1 | ND |
| | | | | | | G9b | 18.8 | 15.2 | 1.0 | 1.0 | 1.2 | ND |
| | | | | | | F10b | 17.7 | 15.1 | 1.1 | 1.0 | 1.2 | ND |
| | | | | | | G10b | 19.0 | 15.4 | 1.0 | 1.0 | 1.1 | ND |
| | | | | | | C12b | 18.0 | 15.4 | 1.1 | 1.0 | 1.1 | ND |
| | | | | | | | | | | | | ND |
| | | | C11b | 16.4 | 17.4 | | | | | | | ND |
| | | | D11b | 15.0 | 17.0 | | | | | | | ND |
| | | | E11b | 16.0 | 16.9 | | | | | | | ND |
| | E3 | 4.0 | | | | | | | | | | ND |
| MOB5B | C6 | 17.5 | | | | | | | | | | No |
| | H3 | 17.9 | | | | | | | | | | No |
| | B4 | 3.0 | E1b | 2.4 | 4.4 | | | | | | | No |
| | | | F5b | 1.7 | 4.2 | | | | | | | ND |
| | | | D7b | 2.9 | 3.0 | H9b | 2.1 | 2.7 | 6.9 | 5.1 | 5.5 | ND |
| | | | | | | H10b | 1.9 | 1.9 | 5.5 | 5.0 | 3.3 | ND |
| | | | | | | G1b | 1.8 | 3.0 | 3.8 | 1.7 | 3.4 | ND |
| | | | | | | H4 | 2.4 | 3.8 | 6.3 | 4.3 | 4.4 | ND |
| | | | | | | G3 | 2.3 | 3.4 | 6.7 | 4.4 | 4.9 | ND |
| MOB5C | C4 | 3.3 | | | | | | | | | | No | functional screening determined by measuring % of uncleaved PAR4 peptide expressed on HEK293 cells. Hybridoma supernatants that demonstrated greater than 70% of uncleaved PAR4 were considered positive.
ND = not determined

TABLE 4

| | | PAR4 clone second screening | | | | | |
|---|---|---|---|---|---|---|---|
| Series | clone | Fold binding native vs KLH-linked PAR4 peptide | Binding to mouse PAR4 ratio | Binding to PAR3 ratio | Binding to PAR2 ratio | Binding to PAR1 ratio | Functional screen on hybridoma supernatants# |
| MOB5F | F3 | 17.3 | 15.7 | 1.0 | 1.2 | 1.2 | Yes (++) |
| | C2 | 15.5 | 14.7 | 1.0 | 1.1 | 1.1 | Yes (++) |
| | E6 | 12.0 | 12.2 | 0.8 | 1.3 | 1.1 | Yes (+) |
| | E3 | 10.6 | 10.6 | 1.0 | 1.3 | 1.1 | no |
| | A4 | 14.9 | 12.2 | 0.9 | 1.3 | 1.0 | Yes (+) |
| | D4 | 1.2 | 1.3 | 1.0 | 1.3 | 1.1 | Yes (+) |
| MOB5G | A1 | 16.6 | 13.6 | 1.0 | 1.2 | 1.0 | Yes (+) |
| | D6 | 15.0 | 13.4 | 1.0 | 1.2 | 1.0 | No |
| | A2 | 15.4 | 15.2 | 1.0 | 1.1 | 1.0 | Yes (++=) |
| | E6 | 15.0 | 12.3 | 1.0 | 1.3 | 1.2 | Yes (+) |
| | C5 | 10.6 | 9.1 | 1.1 | 1.1 | 1.2 | Yes (+) |
| | F6 | 16.5 | 11.9 | 1.0 | 1.1 | 1.0 | ND |
| | G | 11.1 | 8.6 | 0.8 | 1.0 | 1.1 | Yes (+++) |
| | C3 | 10.5 | 12.0 | 0.9 | 1.2 | 1.0 | Yes (+) |
| | B1 | 1.2 | 1.2 | 0.9 | 1.2 | 1.1 | Yes (+) |
| | E5 | 1.8 | 1.3 | 1.2 | 1.5 | 1.5 | no |
| MOB5H | G4 | 11.6 | 12.5 | 1.0 | 1.2 | 1.2 | no |
| | A6 | 14.0 | 13.4 | 1.0 | 1.0 | 1.1 | Yes (++) |
| | C6 | 15.6 | 14.0 | 1.0 | 1.1 | 1.0 | no |
| | H4 | 16.6 | 13.6 | 0.9 | 1.0 | 1.0 | Yes (+) |
| | A3 | 15.6 | 11.2 | 0.9 | 1.1 | 1.1 | Yes (+++) |
| | F2 | 11.9 | 10.4 | 0.9 | 1.0 | 1.0 | no |
| | H1 | 7.1 | 10.5 | 0.9 | 1.1 | 1.0 | Yes (+) |
| | G2 | 10.3 | 9.5 | 0.9 | 0.9 | 0.9 | Yes (+) |
| | D4 | 10.6 | 11.1 | 1.0 | 1.0 | 1.1 | no |
| | F1 | 7.5 | 8.0 | 0.8 | 1.0 | 1.0 | no |
| | B6 | 9.6 | 10.4 | 0.9 | 1.0 | 0.9 | Yes (+) |
| | D2 | 6.0 | 6.2 | 0.9 | 1.0 | 1.0 | no |
| | D6 | 1.0 | 1.1 | 0.9 | 1.1 | 1.1 | Yes (+) |
| MOB5I | G1 | 9.2 | 9.4 | 1.0 | 1.0 | 1.0 | Yes (+) |

Functional analysis performed by platelet aggregation assay
+++ = aggregation <25% of control
++ = aggregation <50% of control
+ = aggregation between 50-80% of control
No = aggregation >80% of control
ND = not determined

Example 2 Anti-PAR4 Hybridoma Clones Block Thrombin-Induced Cleavage of PAR4

Monoclonal antibody hybridoma supernatants (MoB5ARC3, MoB5BRB4, MoB5BRC6, MoB5BRH3 and MoB5CRC4) were screened for their ability to cleave intact PAR4 present on the surface of HEK293 cells transfected with human PAR4 containing an N-terminal FLAG tag. Cleavage was quantified by flow cytometry and shown in FIG. 2.

The transfected HEK293 cells were incubated with either anti-PAR4 polyclonal antibody (described in French S L et al. (2016) J Thromb Haemost 14, 1642-1654 used as a positive control) or monoclonal antibody clone MoB5ARC3, MoB5BRB4, MoB5BRC6, MoB5BRH3 or MoB5CRC4 and untreated negative control in the presence of thrombin (0.1 U/ml) for 10 minutes at room temperature. Cleavage of PAR4 by thrombin was measured by loss of FLAG tag from the PAR4 expression HEK293T cells using flow cytometry.

Treatment of cells with thrombin (2 U/ml for 10 mins) resulted in cleavage of approx. 50% of total PAR4 (−ve control). Pre-treatment with the polyclonal anti-PAR4 antibody was found to almost completely block thrombin-induced cleavage (+ye control) (FIG. 2). An initial screen of five hybridoma supernatants showed that MoB5ARC3 almost completely blocked thrombin-induced cleavage of PAR4, with limited and variable responses to supernatants from the four other hybridomas (B5A.RC3, B5.BRB4, B5.BRC6, B5.BRH3 and B5.CRC4).

Clone B5A.RC3 blocked thrombin-induced cleavage of PAR4 by at least 90%. Clone B5.BRB4 blocked thrombin-induced cleavage by about 60%, B5BRC6 blocked thrombin-induced cleavage by about 50%, B5BRH3 blocked thrombin-induced cleavage by about 65% and B5CRC4 blocked thrombin-induced cleavage by about 50%.

Figure 3:
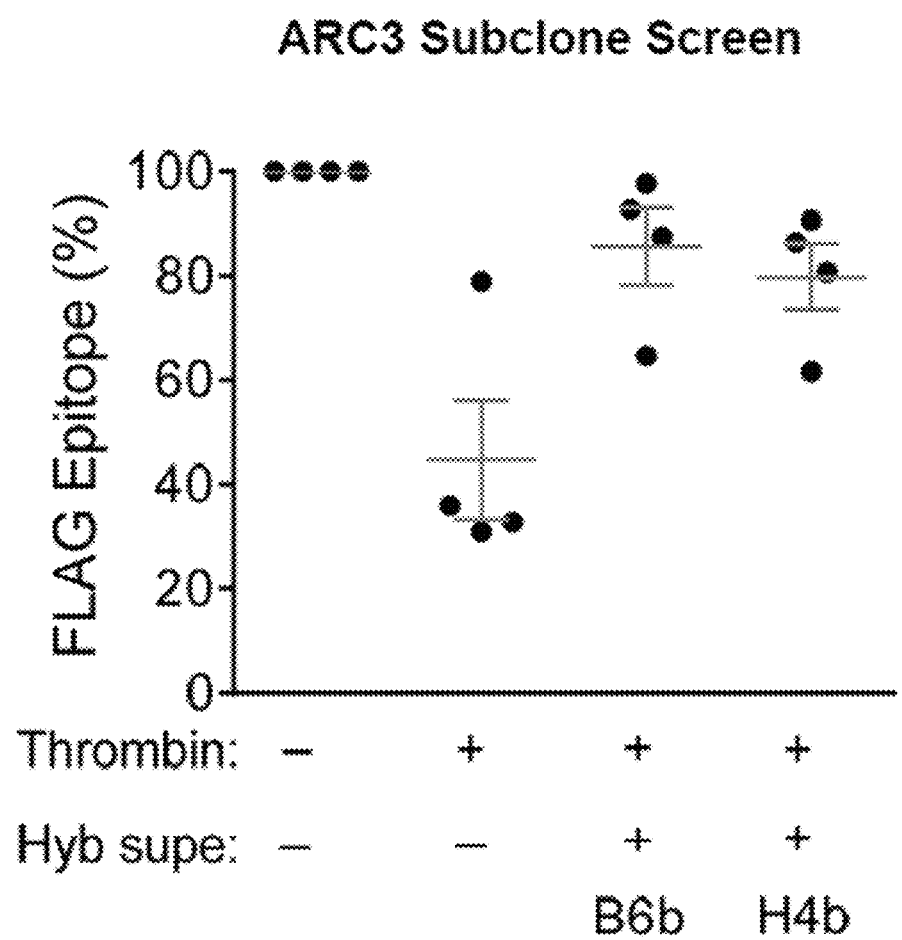
FIG. 3 shows the percentage of intact PAR4 (as measured by % FLAG epitope) present on the cell surface of HEK293 cells transfected with PAR4 containing an N-terminal FLAG tag as quantified by flow cytometry. The cells were pre-treated with supernatant from two sub-clones of 5A.RC3 (designated B6b and H4b) prior to treatment with thrombin (2 U/ml for 10 mins). Data are mean+standard error of the mean for four individual data points.

Clone 5A.RC3 was further sub-cloned by limiting dilution according to standard protocols and tested for ability to block thrombin-induced cleavage of PAR4 as shown in FIG. 3 as measured by flow cytometry. Both hybridoma supernatants from 5A.RC3 (sub-clone H4b) and 5A.RC3 (sub-clone B6b) provided at 100 µl supernatant blocked thrombin-induced cleavage of PAR4 on HEK293T cells (100 µl cell suspension) to a significant extent, over 90%.

Figure 4:
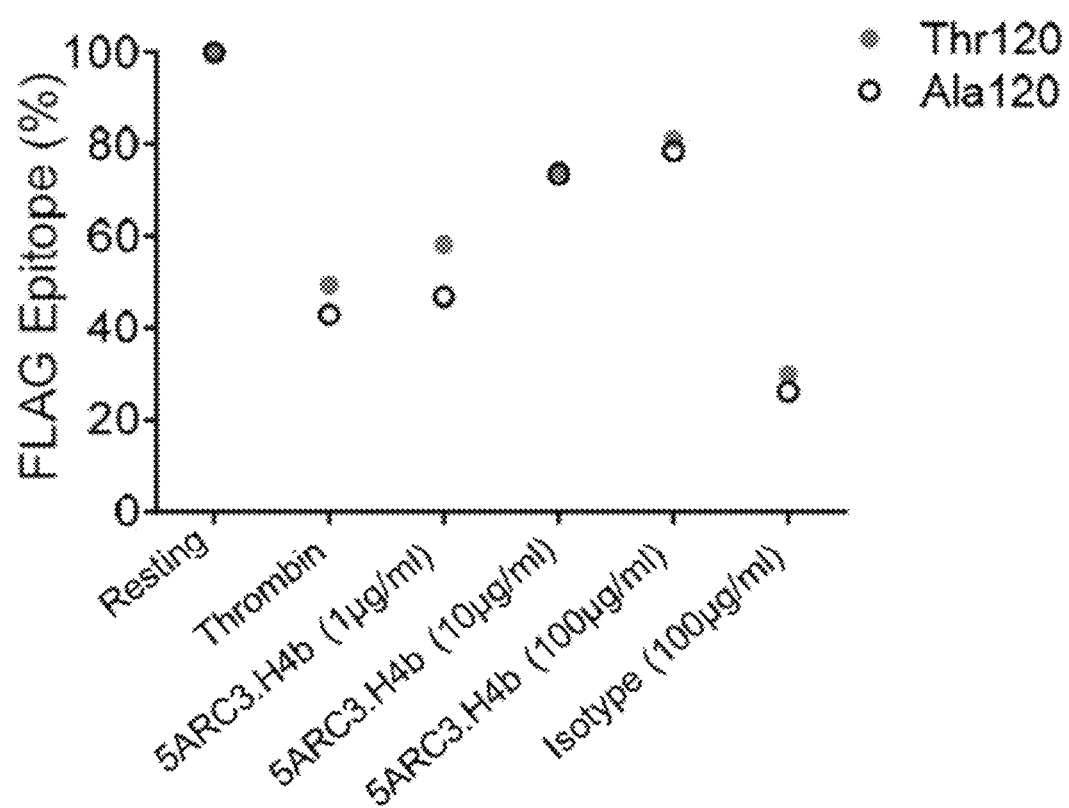
FIG. 4 shows the percentage of intact PAR4 (as measured by % FLAG epitope) present on the cell surface of HEK293 cells transfected with either the Thr120 or Ala120 variant of human PAR4 containing an N-terminal FLAG Tag as quantified by flow cytometry. The cells were pre-treated with various concentrations of 5A.RC3 sub-clone as indicated followed by treatment with thrombin (2 U/ml).

FIG. 4 shows that 5A.RC3.H4b sub-clone effectively inhibited cleavage of PAR4 expressed on the surface of HEK293 cells in a dose dependent manner and that cleavage was equally effective for both the Ala120 and the Thr120 variants of the human PAR4 receptor.

Example 3 Binding Specificity of H4b and B6b Sub-Clones of mAb-5RC3

In order to determine the specificity of the anti-hPAR4 clones to PAR4, ELISA screening was performed as described above. FIG. 5A shows the result for binding specificity of clones mAb-5ARC3 (5A.RC3) and mAb-5BRB4 (5B.RB4) against hPAR1, hPAR2, hPAR3 and hPAR4.

5A.RC3 demonstrated a 16-fold selectivity to human PAR4 peptide over PAR1, PAR2 and PAR3. mAb 5B.RB4 bound to all four human PAR peptides similarly and with lower affinity to PAR4 compared to 5A.RC3.

The inventors performed surface plasmon resonance (SPR) analysis utilising the Bio-Rad Proteon XPR36 to gain insight into the binding affinity (rate of association and dissociation) and specificity of 5A.RC3.F10b.H4b. Utilising a streptavidin chip, all biotin-coupled human PAR peptides (Table 1) were captured on the surface and different concentrations of purified 5A.RC3 passed over. Clone 5A.RC3.F10b.H4b was observed to have a dissociation constant (KD) of about 0.4 nM by SA chip SPR (FIG. 5B).

Example 4 Anti-PAR4 Hybridoma mAb-5RC3.F10b.H4b (Hereinafter 5A.RC3) Blocks Thrombin Induced Cleavage of Both Human PAR4 Variants One of the limitations of PAR4 inhibitors of the prior art is that they are specific to a particular variant of PAR4 and accordingly can only successfully inhibitor platelet aggregation in persons having the relevant PAR4 receptor variant.

In order to determine whether the anti-PAR4 clones could inhibit the effects of thrombin on PAR4 cleavage, in vitro inhibition assays were performed. HEK293T cells were transiently transfected with the PAR4-120Ala (A) or PAR4-120Thr (T) variants which contained a FLAG epitope upstream of the thrombin cleavage site. Cleavage of PAR4 by thrombin was measured by loss of Flag tag from the PAR4 expressing HEK293 cells using flow cytometry.

Figure 6:
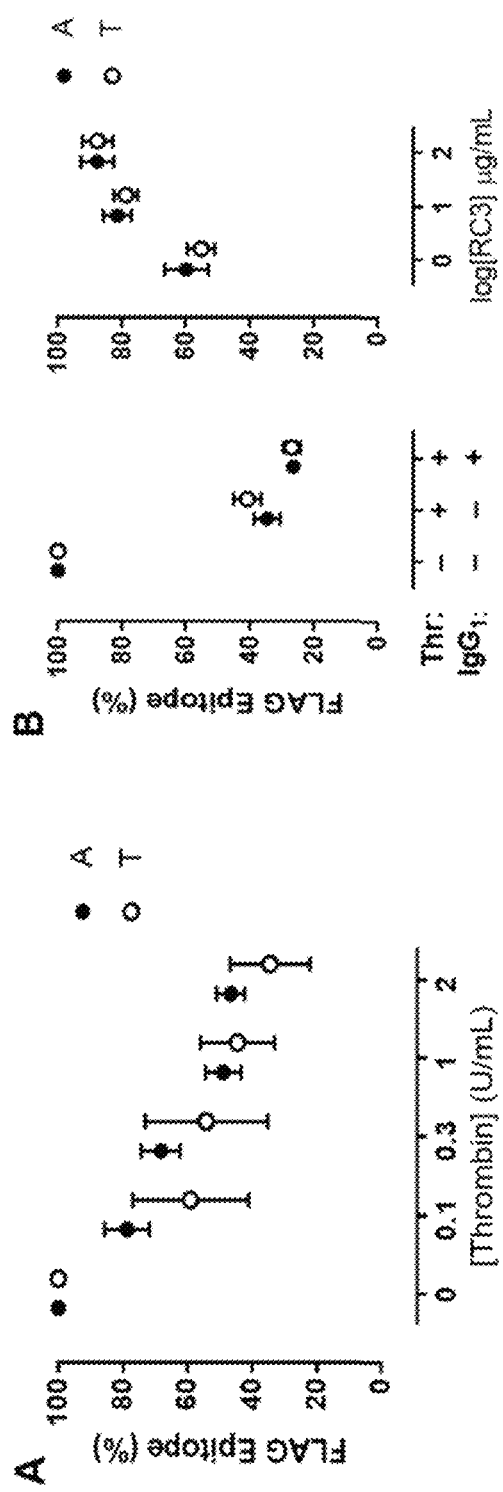

Cells were stimulated with increasing doses of thrombin (0.1-2U/ml) and the amount of thrombin cleavage was measured as a loss of FLAG epitope using a FITC-conjugated anti-FLAG antibody by flow cytometry. As shown in FIG. 6A, inhibition was dose dependent.

FIG. 6B shows that pre-incubation of transfected cells with 5A.RC3 (100 µg/ml) before thrombin stimulation provided near complete inhibition of thrombin cleavage to the same extent regardless of PAR4 variant.

FIG. 6B shows the result for 5A.RC3 (10 µg/ml) on PAR4 cleavage of HEK293 cells compared to either vehicle, isotype control and co-incubated with thrombin (0.1 U/ml) for 10 minutes.

Monoclonal antibody 5A.RC3 significantly inhibited thrombin induced PAR4 cleavage of both the Ala120 and Thr120 variant of PAR4 and activation of human PAR4. This functionality of anti-hPAR4 antibody 5A.RC3 was reversed with the addition of the immunising peptide.

Example 5 Inhibition of Platelet Aggregation

Figure 7:
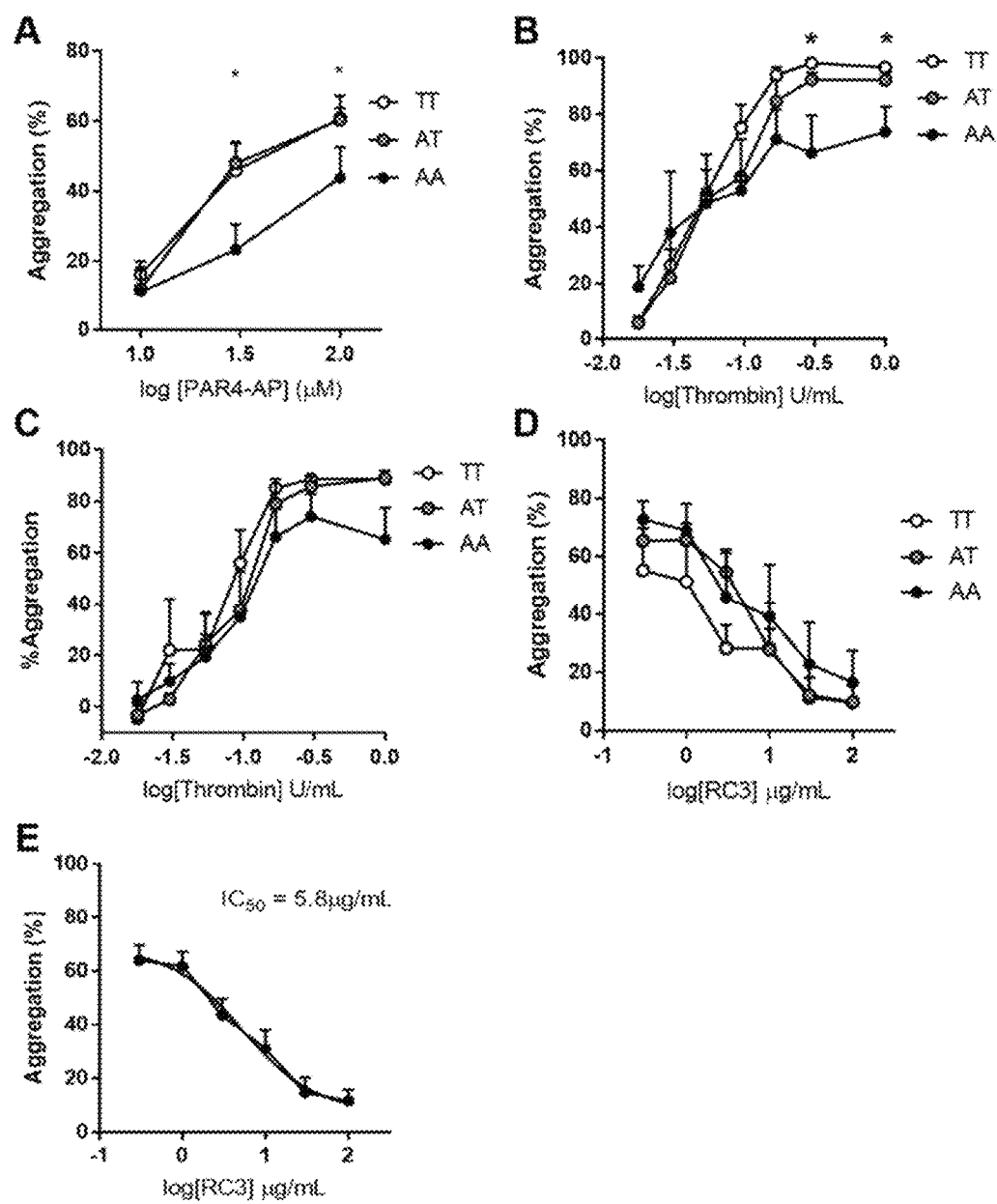

In order to determine whether the anti-hPAR4 antibody MoB5ARC3.H4b (5A.RC3) could inhibit the effects of thrombin on PAR4 observed by platelet aggregation, ex vivo platelet aggregation assays on human platelets were performed. Human isolated platelets of different PAR4 variants were assessed for their responses to PAR4 agonists. Three different genotypes were tested (TT, AT and AA) as shown in FIG. 7.

As shown in FIGS. 7A and B, the presence of the T allele was associated with higher maximum aggregation in response to mid-range doses of PAR4-activating peptide (AP) and thrombin. PAR4-AP is a selective PAR4 agonist having the C-terminal amidated peptide sequence AYPGKF-NH$_2$ (SEQ ID NO: 118).

FIG. 7C shows thrombin stimulation in the presence of PAR1 blockade with vorapaxar (90 nm).

FIG. 7D shows that platelet aggregation was inhibited in a dose dependent manner by 5A.RC3. This dose-dependent inhibition was equally effective across all genotypes.

FIG. 7E shows the inhibitory concentration (IC50) for the 5A.RC3 sub-clone.

Figure 8:
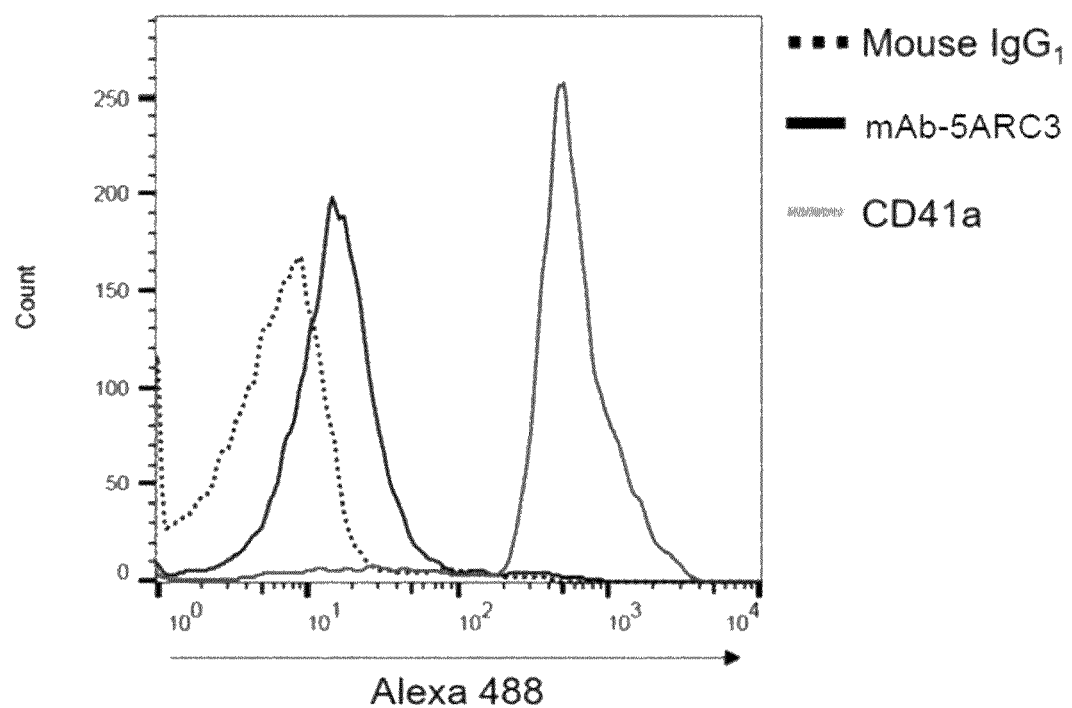
FIG. 8 shows that 5A.RC3 (10 ug/mL) binds human PAR4 in isolated platelets as shown by flow cytometry against an isotype control.

Example 6 MoB5ARC3.F10b.H4b (Hereinafter 5A.RC3) Binds to PAR4 on Human Platelets Clone 5A.RC3 was tested for binding to isolated human platelets in vitro. Analysis of binding was determined using flow cytometry. Isolated platelets were incubated with either mouse IgG1 (isotype control) or 5A.RC3 and tested for binding to PAR4. CD41a which is a marker expressed on platelets was used as a positive control. As shown in FIG. 8, 5A.RC3 (10 µg/ml) binds human PAR4 in isolated platelets.

Example 7 Inhibition of Pro-Coagulant Activity in Isolated Platelets Demonstrated by MoB5ARC3.F10b.H4b (Hereinafter 5A.RC3)

Platelet surface phosphatidylserine (PS) exposure was determined by measuring annexin V binding. Human isolated platelets ($5\times10^7$/ml) were pre-treated with 5A.RC3 (5 mins) at the concentrations indicated and were incubated with Alexa Fluor 488-conjugated annexin-V (1:100) prior to stimulation with thrombin. After stimulation, platelets were resuspended in modified Tyrode's buffer for flow cytometry analysis (FACSCalibur, BD Biosciences).

Pro-coagulant activity in isolated human platelets was examined by measuring phosphatidylserine (PS) exposure in response to stimulation with PAR4-AP or thrombin (1 U/ml) The percentage of annexin V positive cells was measured. The platelets were pre-incubated with 5A.RC3 for 5 mins. Blood is flowed for 10 mins and the data collected in real-time. The 10 min (final data point) is shown for simplicity.

Figure 9:
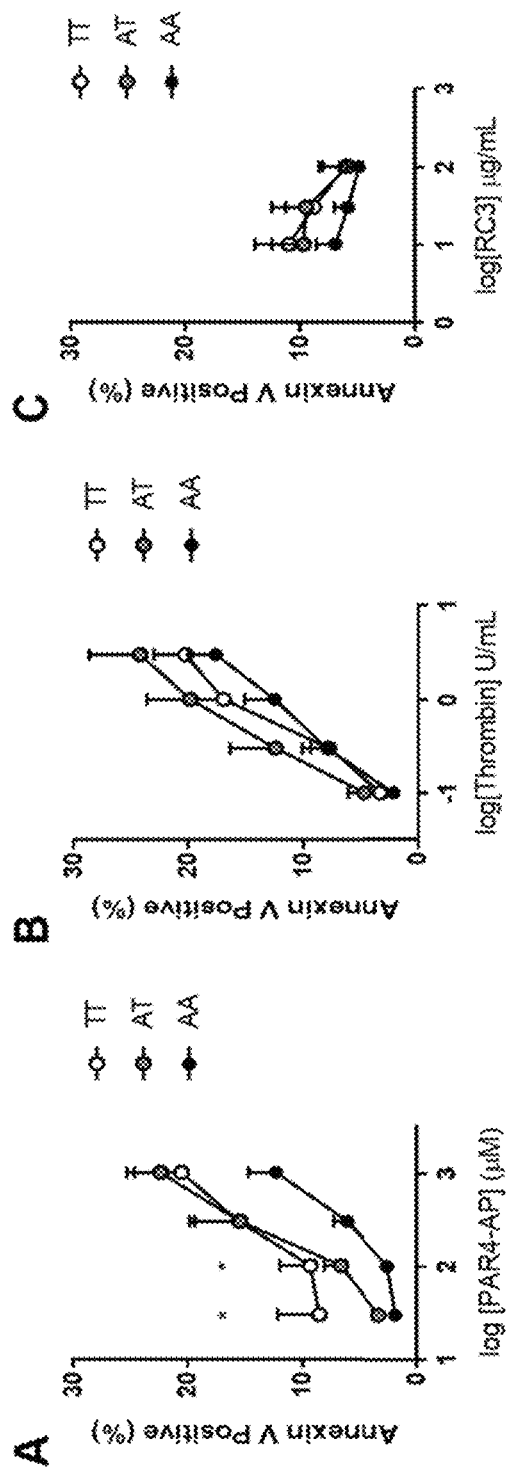
FIG. 9 shows that the PAR4 genotype is associated with an increase in a pro-coagulant platelet phenotype and is targetable by antibody-mediated inhibition. Human isolated platelets were assessed for pro-coagulant activity via measuring phosphatidylserine exposure in response to (A) PAR4-activating peptide (AP) stimulation and (B) thrombin stimulation. Note that the Thr120 variant leads to increased PS exposure in PAR4-AP stimulated platelets, with a similar trend observed in thrombin stimulated platelets. (C) Pre-treatment with 5A.RC3 sub-clone dose-dependently inhibited thrombin-induced phosphatidylserine exposure regardless of donor genotype.

FIG. 9 shows the percentage of annexin V positive cells in response to either PAR4-AP stimulation (A) or thrombin stimulation (B). The thr120 variant lead to increased PS exposure in PAR4-AP stimulated platelets, with a similar trend observed in thrombin stimulated platelets.

FIG. 9C shows that pre-treatment with 5A.RC3 (5 min) inhibited thrombin-induced phosphatidylserine exposure in a dose dependent manner regardless of donor genotype.

Example 8 Anti-Thrombotic Effect of MoB5ARC3.F10b.H4b (Hereinafter 5A. RC3)

Thrombosis parameters including platelet deposition, thrombin activity, fibrin volume and ratio of fibrin per thrombus were measured in real-time over a period of 10 minutes in a whole blood thrombosis assay as described herein under conditions of coagulation.

Platelet deposition (PE-conjugated anti-CD9), thrombin activity (FRET-based thrombin probe), fibrin volume (Dylight650-conjugated anti-fibrin antibody) and the ratio of fibrin per thrombus at the 10 minute end-point is shown in FIG. 10A by confocal microscopy (to allow for volume measurements to be taken) using a Nikon A1r with a 25× lens and 2× digital magnification.

Figures 1, 10:
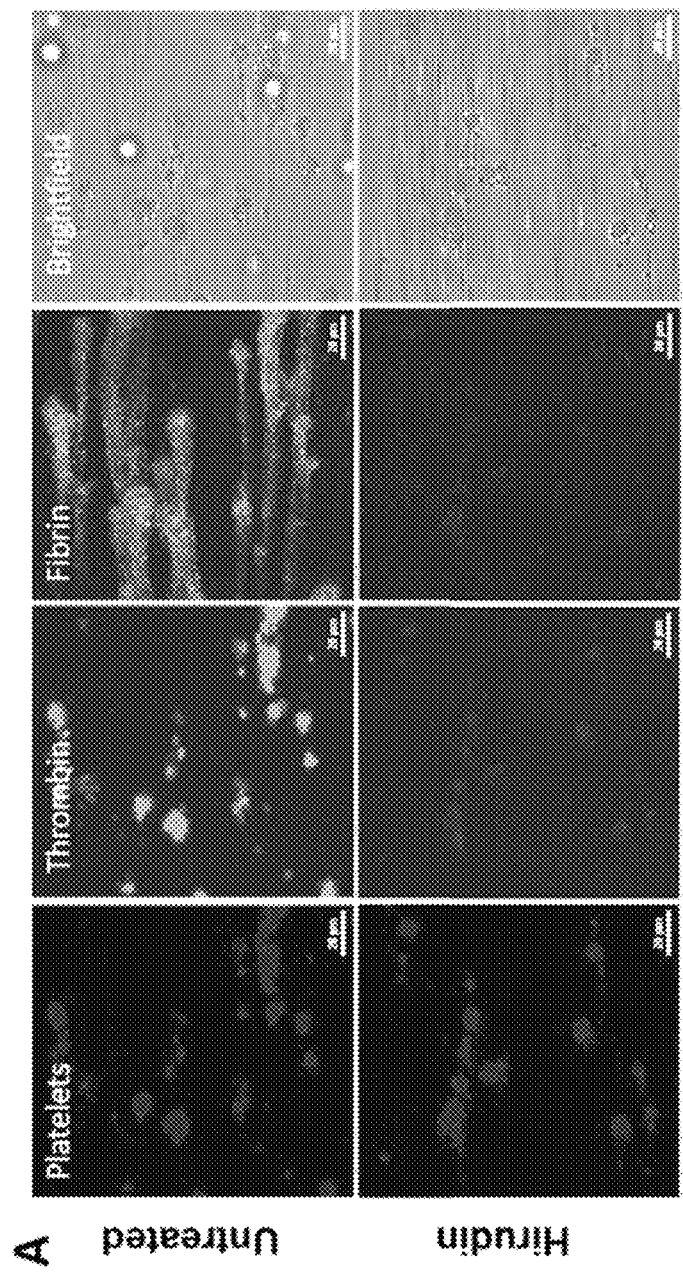
Figures 2, 10:
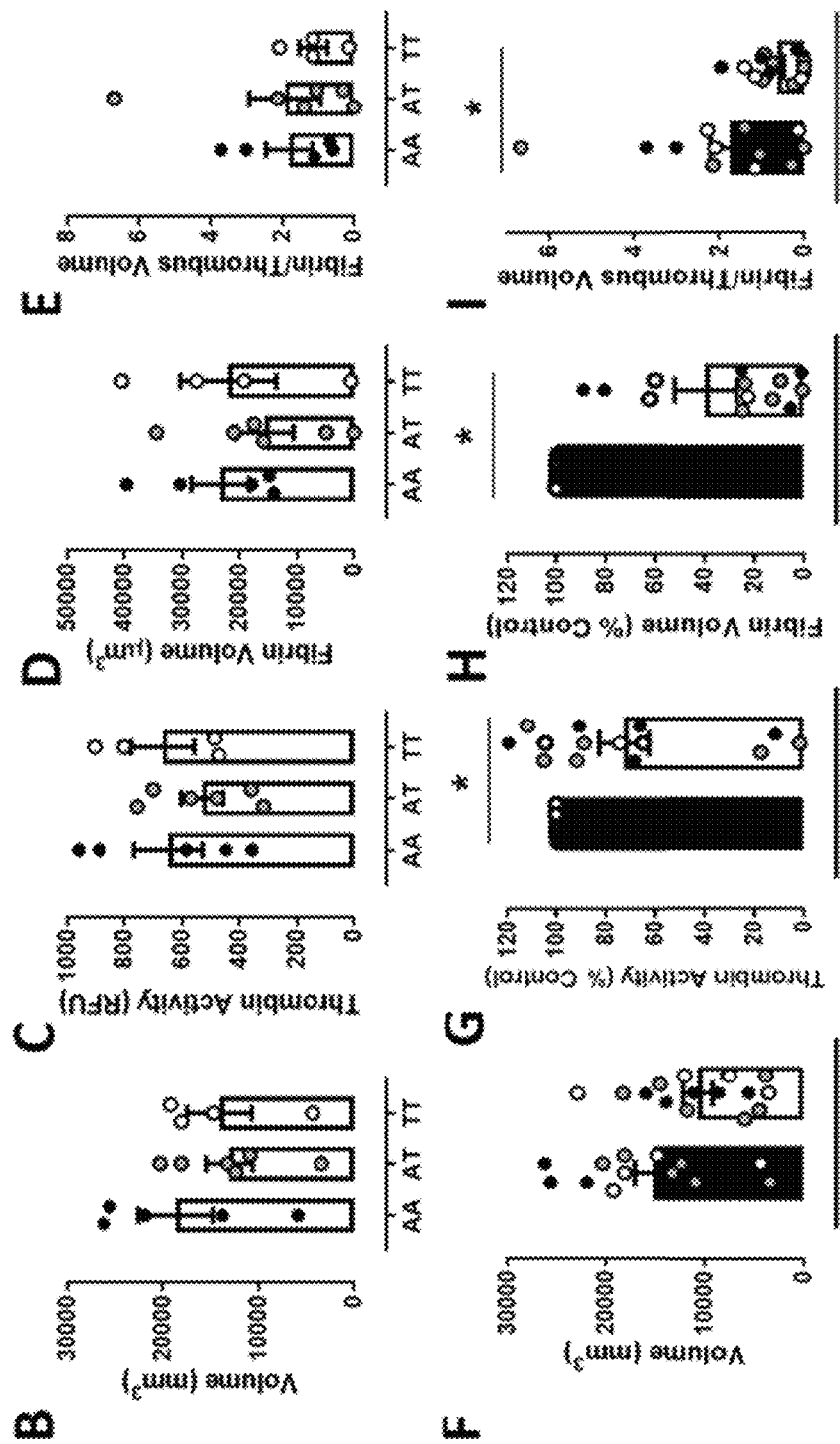

The direct thrombin inhibitor, hirudin (800 U/ml) abolished thrombin activity and fibrin volume despite continued platelet deposition. FIG. 10 B-E shows that no significant differences in the above parameters was observed across PAR4 genotypes. Pre-treatment with 5A.RC3 (100 µg/ml) as shown by the open bars had no effect on platelet deposition (F), but significantly inhibited thrombin activity (G), thrombin activity (H), fibrin volume (H) and the ration of fibrin per thrombus volume (I) compared to the control (black bars).

Example 9 Further Screening of Additional Clones

Clones that were identified from the binding screens as having reasonable affinity and specificity for human PAR4 were examined further by functional platelet aggregation assay.

Figure 11:
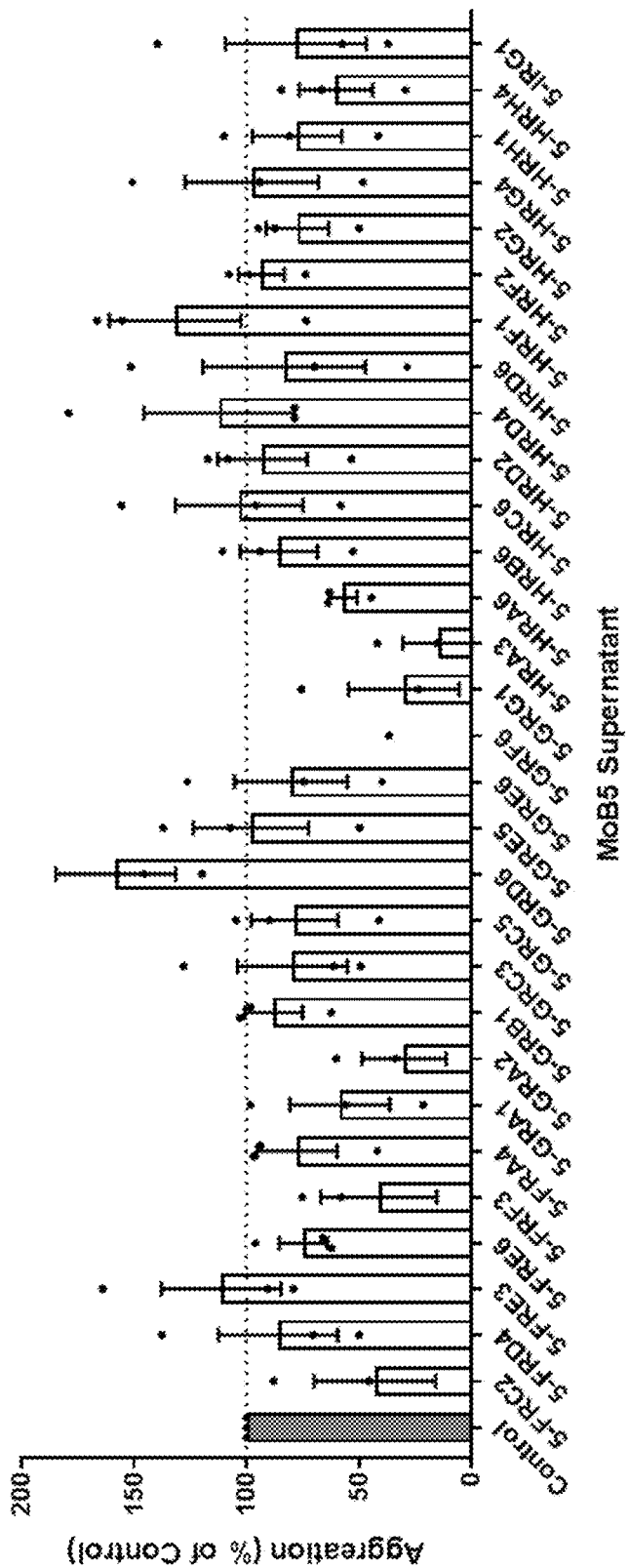
FIG. 11 shows a functional screen of initial hybridoma supernatants for platelet aggregation.

Thrombin-induced platelet aggregation in the presence of a PAR1 antagonist (i.e. PAR4-dependent aggregation) is shown for 30 monoclonal antibody supernatants binding to human platelets. Antibody supernatant was mixed with human platelets ($2 \times 10^8$ cells) at a 1:1 ratio. FIG. 11 shows the maximum aggregation achieved at 50 minutes, expressed as a percentage of control (n=3 individual donors).

Example 10 Sequences of Two Inhibitor Clones and One Non-Inhibitor Clone

Sequencing of monoclonal antibodies which were all of the IgG1 kappa isotype was undertaken at the Monash Antibody Technologies Facility at Monash University.
(i) 5A.RC3 Subclone
The nucleotide and amino acid sequence of the heavy chain variable region and the light chain variable region was determined and is provided in the sequence listing which forms part of the present disclosure and as shown in FIG. 12. This antibody is an antagonist and is of the IgG2a isotype.
The sequences of the complementary determining regions (CDRs) are shown below:
5A.RC3 Heavy Chain CDRs:
CDR1: GFTLSNYG (SEQ ID NO:13)
CDR2: IWYDGSNK (SEQ ID NO:14)
CDR3: ARESIVEVLPPFDY (SEQ ID NO:15)
5A.RC3 Light Chain CDRs:
CDR1: QRVRNNY (SEQ ID NO:16)
CDR2: GAS (SEQ ID NO:17)
CDR3: QQYGNSYT (SEQ ID NO:18)
(ii) 5F.RF3 Subclone
The nucleotide and amino acid sequence of the heavy chain variable region and the light chain variable region was determined and is provided in the sequence listing which forms part of the present disclosure and as shown in FIG. 14. This antibody is an antagonist. The antibody isotype is IgG2b kappa.

The sequences of the complementary determining regions (CDRs) are shown below:
5F.RF3 Heavy Chain CDRs:
CDR1: AYTFTNYG (SEQ ID NO: 24)
CDR2: ISPYNGNT (SEQ ID NO: 25)
CDR3: AREYNRSSRGRYYYYGMDV (SEQ ID NO:26)
5F.RF3 Light Chain CDRs:
CDR1: QSVSSNY (SEQ ID NO:27)
CDR2: GAS (SEQ ID NO:28)
CDR3: QQYGSSPWT (SEQ ID NO:29)
(iii) 5H.RD2 Subclone
The nucleotide and amino acid sequence of the heavy chain variable region and the light chain variable region was determined and is provided in the sequence listing which forms part of the present disclosure and as shown in FIG. 13. This antibody did not function as an antagonist even though it bound PAR4. The isotype of this antibody is IgG1 kappa.
The sequences of the complementary determining regions (CDRs) are shown below:
5H.RD2 Heavy Chain CDRs:
CDR1: GFTFFNTW(SEQ ID NO: 34)
CDR2: VKSKNDGGTK (SEQ ID NO: 35)
CDR3: TTDPHYDFWSAY (SEQ ID NO: 36)
5H.RD2 Light Chain CDRs:
CDR1: QSLVHSDGNT (SEQ ID NO: 37)
CDR2: KIS (SEQ ID NO:38)
CDR3: LQATQFMYT (SEQ ID NO: 39)
Designation of CDRs and framework regions were determined using the IMGT/V-Quest program.

Example 11 Measurement of Binding Kinetics of Seven Purified Monoclonal Antibody Clones by Two Different Surface Plasmon Resonance Assays (SPR)

Two different methods were used to measure the binding kinetics of seven purified anti-hPAR4 mAbs described in Table 4 below.

For the mAb capture method low levels of ligand mAb and analyte hPAR4 were used in an attempt to produce a 1:1 binding interaction, this method has been used successfully to measure kinetics and affinity KD's (Kamat V and Rafique A (2017) Analytical Biochemistry 530:75-86), despite using a whole IgG. For the streptavidin capture method despite using very low levels of analyte (mAb) there may be greater than a 1:1 interaction due to whole antibody being used in this analysis.

Purified mAbs were analysed by ELISA for binding to hPAR4 (FIG. 15) and the data expressed as ELISA positive: negative ratios. The kinetics of the binding interaction between the mAbs and hPAR4 was measured using Surface Plasmon Resonance (SPR; Biacore) by two different methods: 1. Anti-mouse Fc mAb capture method and 2. Streptavidin (SA) chip to capture biotinylated peptide. The ka(on) rate and kd(off) rates and KD were measured and fitted to a Langmuir model using the Biacore evaluation software.

TABLE 4

Characterisation of purified anti-hPAR4 mAbs

| mAb | Clonal (full name) | Isotype | ELISA Pos: Neg ratio | mAb capture SPR | | | SA chip biotin peptide SPR | | |
|---|---|---|---|---|---|---|---|---|---|
| | | | | ka (1/Ms) | kd (1/s) | KD (nM) | ka (1/Ms) | kd (1/s) | KD (nM) |
| 5A RC3 | 5A RC3.F10b.H4b | IgG2a/k | 13.9 | 3.30E+05 | 4.87E−03 | 14.8 | 1.32E+06 | 4.17E−04 | 0.32 |
| 5D RH4 | 5D RH4.G7.E6.C7b.G7 | IgG2a/k | 13.3 | 1.78E+05 | 3.90E−03 | 22 | 4.28E+05 | 9.56E−05 | 0.23 |
| 5H RA3 | 5H RA3.D3b.A2b | IgG2a/k | 14.8 | 6.95E+05 | 1.12E−03 | 16 | 2.57E+06 | 8.57E−04 | 0.34 |

TABLE 4-continued

Characterisation of purified anti-hPAR4 mAbs

| mAb | Clonal (full name) | Isotype | ELISA Pos: Neg ratio | mAb capture SPR | | | SA chip biotin peptide SPR | | |
|---|---|---|---|---|---|---|---|---|---|
| | | | | ka (1/Ms) | kd (1/s) | KD (nM) | ka (1/Ms) | kd (1/s) | KD (nM) |
| 5F RF3 | 5F RF3.A7b.C9 | IgG2b/k | 17 | 1.89E+04 | 4.27E−06 | 0.2 | 1.47E+07 | 1.50E−03 | 0.01 |
| 5G RA1 | 5G RA1.E10.G3 | IgG2a/k | 11.5 | 8.23E+04 | 5.60E−03 | 68 | 4.61E+05 | 4.49E−04 | 0.97 |
| 5I RG1 | 5I RG1.D6.C1b | IgG3/k | 6.3 | 1.40E+04 | 1.46E−03 | 105 | 1.85E+06 | 6.67E−04 | 0.36 |
| 5H RF2 | 5H RF2.A5b.D3.C2 | IgG2a/k | 8.5 | 5.84E+04 | 2.27E−03 | 38 | 1.84E+06 | 1.11E−03 | 0.61 |

Example 12 Binding of Anti-hPAR4 Monoclonal Antibodies to hPAR4 Peptide

A similar method to the ELISA screening method described in Example 11 was used to identify the reactivity of purified mAbs binding to the hPAR4 peptide. The experiment was completed with purified mAbs diluted in PBS instead of hybridoma supernatants.

Figure 15:
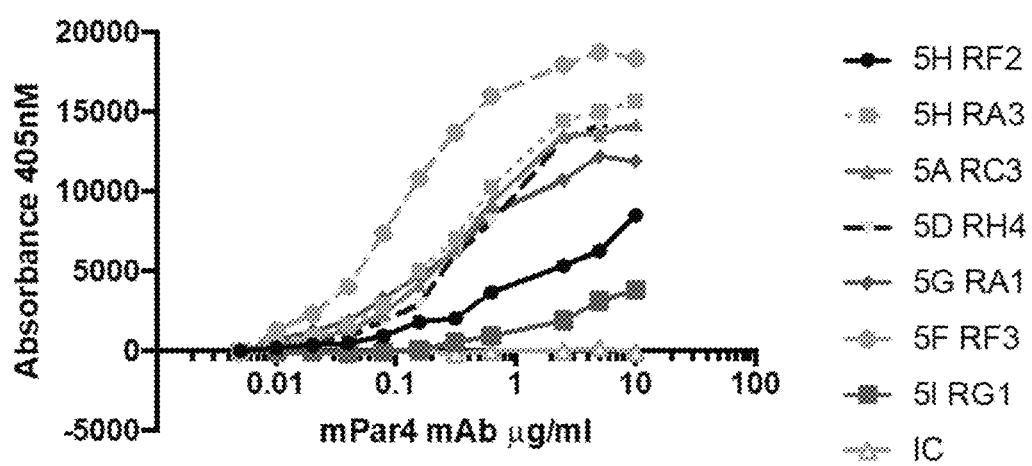
FIG. 15 shows reactivity of purified mAbs with hPAR4 peptide by ELISA. Purified mAbs bound in a dose-dependent manner to hPAR4 peptide detected with anti-mouse Fc conjugated to Alkaline Phosphatase (Ap). No binding was observed for the IC (isotype control) mAb raised against an irrelevant non-PAR4 antigen.
Figure 16:
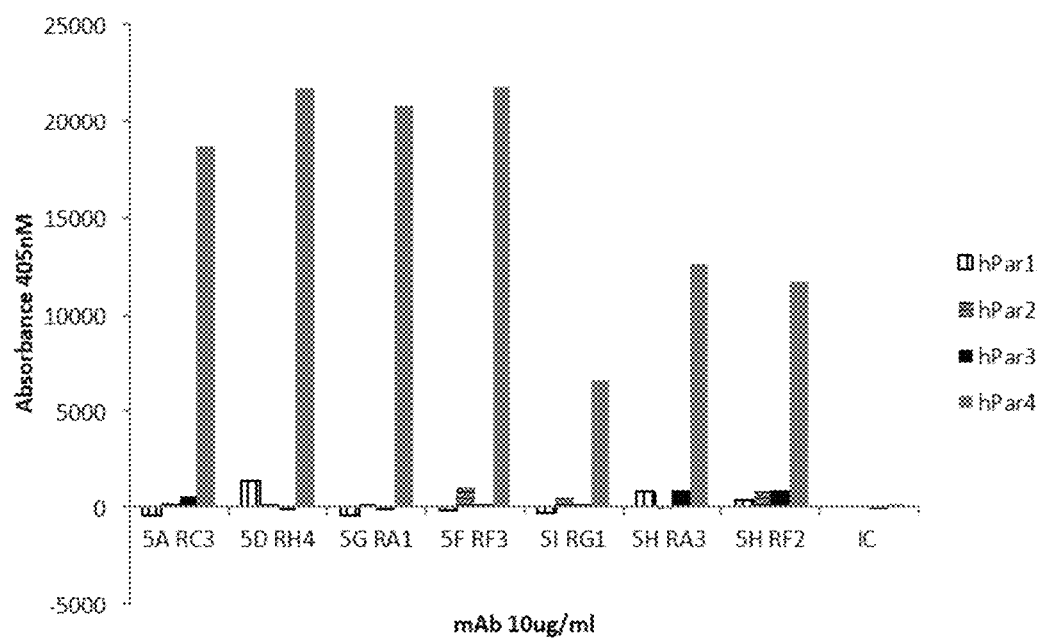
FIG. 16 shows purified anti-HPAR4 mAbs bind specifically to hPAR4 biotinylated peptide and do not react non-specifically to hPAR1, hPAR2 and hPAR3 (biotinylated peptides) at 10 μg/ml by ELISA.

The reactivity of seven purified anti-hPAR4 mAbs was analysed by ELISA (see Table 4). Dilutions of the mAbs were allowed to react with hPAR4 peptide coated wells and the binding curves are shown in FIG. 15 The strongest binding was observed for mAb 5F RF3.A7b.C9 (5F.RF3), followed by three mAbs which had very similar binding curves 5H RA3.D3b.A2b (5H. RA3), 5A RC3.F10b.H4b, (5A.RC3), 5D RH4.G7.E6.C7b.G7 (5D.RH4).

The reactivity of 5G RA1.E10.G3 (5G.RA1) mAb was slightly lower and the least reactive of the mAbs with hPAR4 peptide was 5H RF2.A5b.D3.C2 (5H.RF2) and 5I RG1.D6.C1b (5I.RG1). This data is also expressed as ELISA Positive: Negative ratio shown in TABLE 4.

Example 13 Specificity of Anti-hPAR4 Monoclonal Antibodies for Human PAR4

Wells of a Streptavidin coated plate (Thermo Scientific Pierce Streptavidin high binding capacity coated plate code #15500 blocked with Superblock) were washed 3 times with Wash buffer (PBS containing 0.05% TWEEN 20 and 0.1% Bovine serum Albumin). Biotinylated peptides (hPAR1-4) were diluted in Wash buffer and allowed to bind to the blocked Streptavidin coated wells at 10 ug/ml (100 ul per well) for 1 hour at room temperature with gentle mixing. Wells were washed 3 times as above and purified anti-hPAR4 mAbs prepared at 10 ug/ml in Wash buffer were allowed to bind (100 ul/well) for 1 hour at room temperature with gentle mixing. The plate was washed 3 times as above and anti-mouse Fc conjugated to Alkaline phosphatase (AP) at 0.3 ug/ml (100 ul) was added to the wells for 1 hour as above. Wells were washed 3 times as above and developed with Alkaline Phosphatase substrate as described for the screening supernatant ELISA.

To further characterise the purified anti-hPAR4 mAb's the specificity of the mAbs to hPAR1, hPAR2, hPAR3 and hPAR4 biotinylated peptides was performed. The binding data clearly shows that all seven purified mAb's are highly specific, binding only to hPAR4 and are not reactive with hPAR1, hPAR2 and hPAR3 peptides.

Example 14 Binding and Inhibitory Characteristics of Five Purified Anti-hPAR4 Monoclonal Antibodies The binding of five anti-PAR4 monoclonal antibodies to human platelets was examined by flow cytometry. Table 5 shows the results for each clone with regard to 1) binding to human platelets by flow cytometry (expressed as geometric mean fluorescence intensity [GMFI] observed with 10 μg/ml over that of the same concentration of an isotype control and 2) $IC_{50}$ values for inhibition of human platelet aggregation in response to 0.1 U/ml thrombin.

TABLE 5

Summary of binding and inhibitory characteristics of purified anti-HPAR4 mAbs

| mAb | Clonal (full name) | Binding to human plts FACS GMFI* at 10 ug/ml | IC50 (ug/ml) for inhibition of platelet aggregation |
|---|---|---|---|
| 5A RC3 | 5A RC3.F10b.H4b | 39 | 1.6 |
| 5D RH4 | 5D RH4.G7.E6.C7b.G7 | 33 | 2.2 |
| 5H RA3 | 5H RA3.D3b.A2b | 100 | |
| 5F RF3 | 5F RF3.A7b.C9 | 53 | |
| 5G RA1 | 5G RA1.E10.G3 | 25 | 40 |

Figure 17:
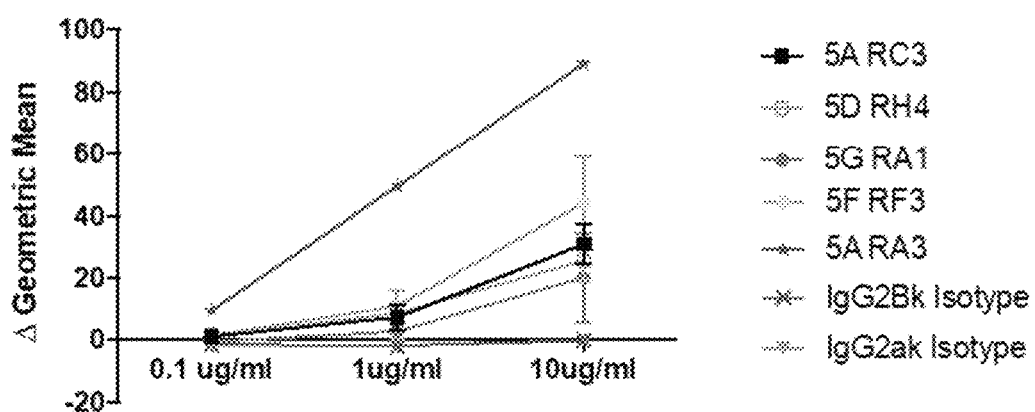
FIG. 17 shows concentration-dependent binding of purified anti-hPAR4 mAbs versus isotype controls to human isolated platelets by flow cytometry. Shown is raw data expressed as geometric mean fluorescence intensity. Each mAb bound in a concentration dependent manner. N=3-5. Data points are means±SEM.

Concentration dependent binding of purified anti-hPAR4 mAbs to human isolated platelets is shown in FIG. 17. Each antibody demonstrated concentration-dependent binding relative to relevant isotype controls.

Figure 18:
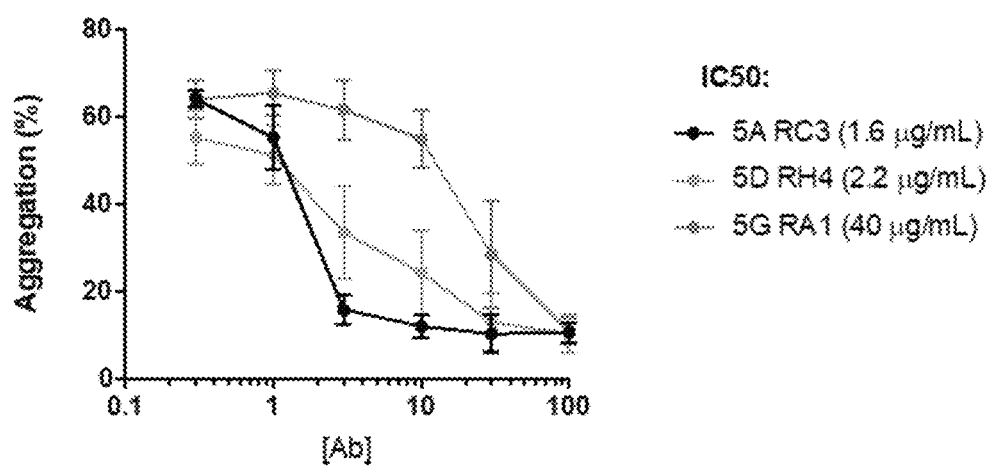
FIG. 18 shows concentration-dependent inhibition of human platelet aggregation induced by 0.1 U/ml thrombin by three anti-hPAR4 mAb clones. Near maximal inhibition was achieved by each clone at the highest concentration tested. $IC_{50}$ values (in μg/ml) determined from these concentration inhibition curves are also shown in the figure. N=4-8. Data points are mean±SEM.

Concentration dependent inhibition of human platelet aggregation induced by 0.1 U/ml thrombin is shown in FIG. 18 for three anti-hPAR4 mAb clones (5A.RC3, 5D.RH4 and 5G.RA1). Near maximal inhibition was observed for each cline at the highest concentrations tested.

Example 15 Anti-thrombotic effect of two anti-PAR4 clones (5D.RH4 and 5A.RC3)

Figure 19:
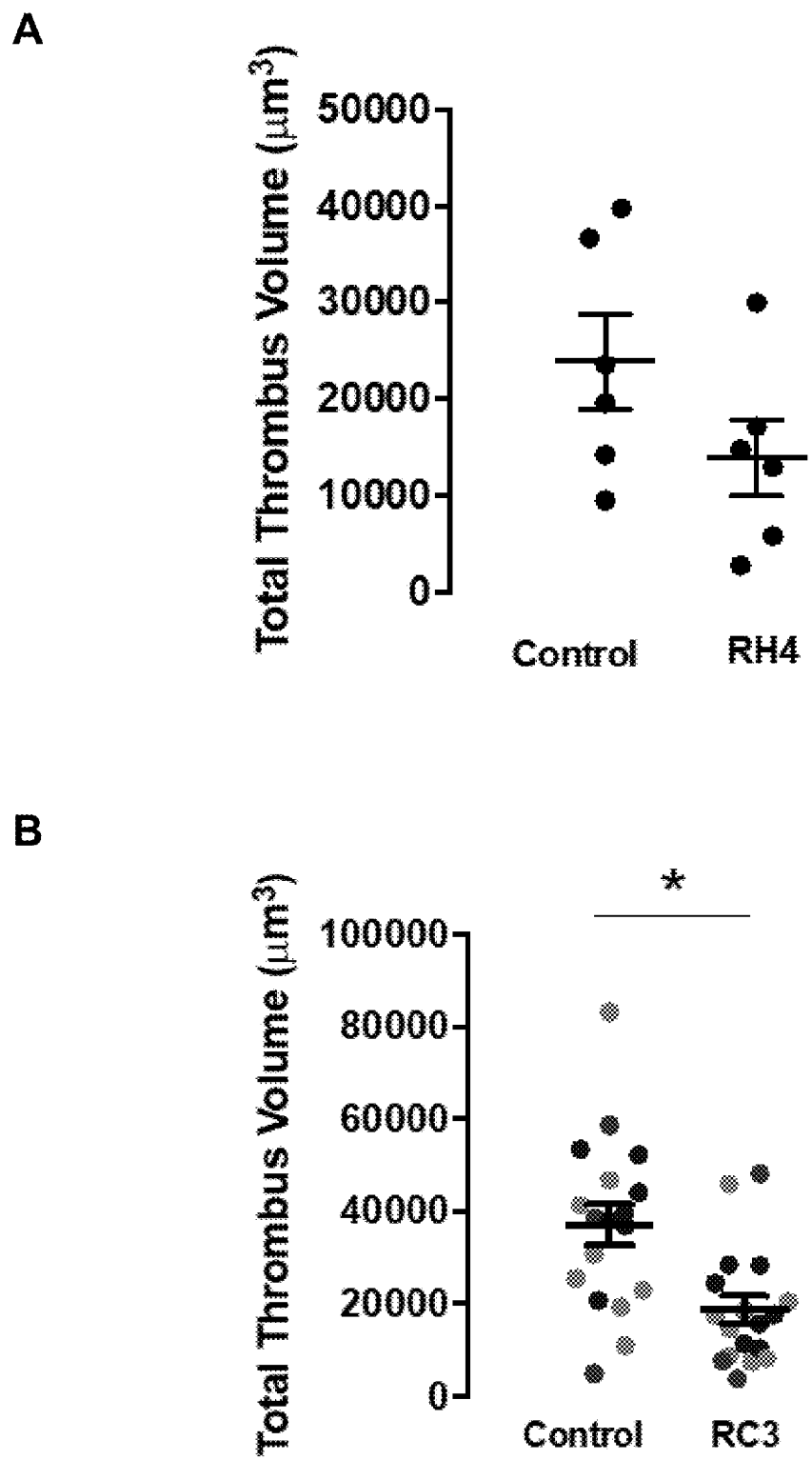
FIG. 19 shows inhibition of human thrombus formation by monoclonal antibodies 5A.RC3 and 5D.RH4. Pre-treatment of blood with either 5D.RH4 or 5A.RC3 (100 μg/ml for both) reduced total thrombus volume. Individual data points are shown. Bars are mean±SEM. *P<0.05 (unpaired Student's t-test).

The inhibition of human thrombus formation by mAb 5A.RC3 and mAb 5D.RH4 was examined by confocal microscopy. The volume of human thrombi formed after 3 min was quantified by confocal microscopy in an ex vivo human whole blood thrombosis assay. Pre-treatment of blood with either mAb at 100 μg/ml reduced total thrombus volume as shown in FIG. 19.

Example 16 Sequences of Purified Anti-hPAR4 mAb Clones

Sequencing of monoclonal antibodies which were all of the IgG1 kappa isotype was undertaken at the Monash Antibody Technologies Facility at Monash University. Designation of CDRs and framework regions were determined using the IMGT/V-Quest program.

Sequences of the variable heavy chain of purified mAbs to human PAR4 are shown in FIG. 20. The complementary determining regions (CDRs) are indicated in the figure according to the IMGT numbering system.

Figures 1, 21:
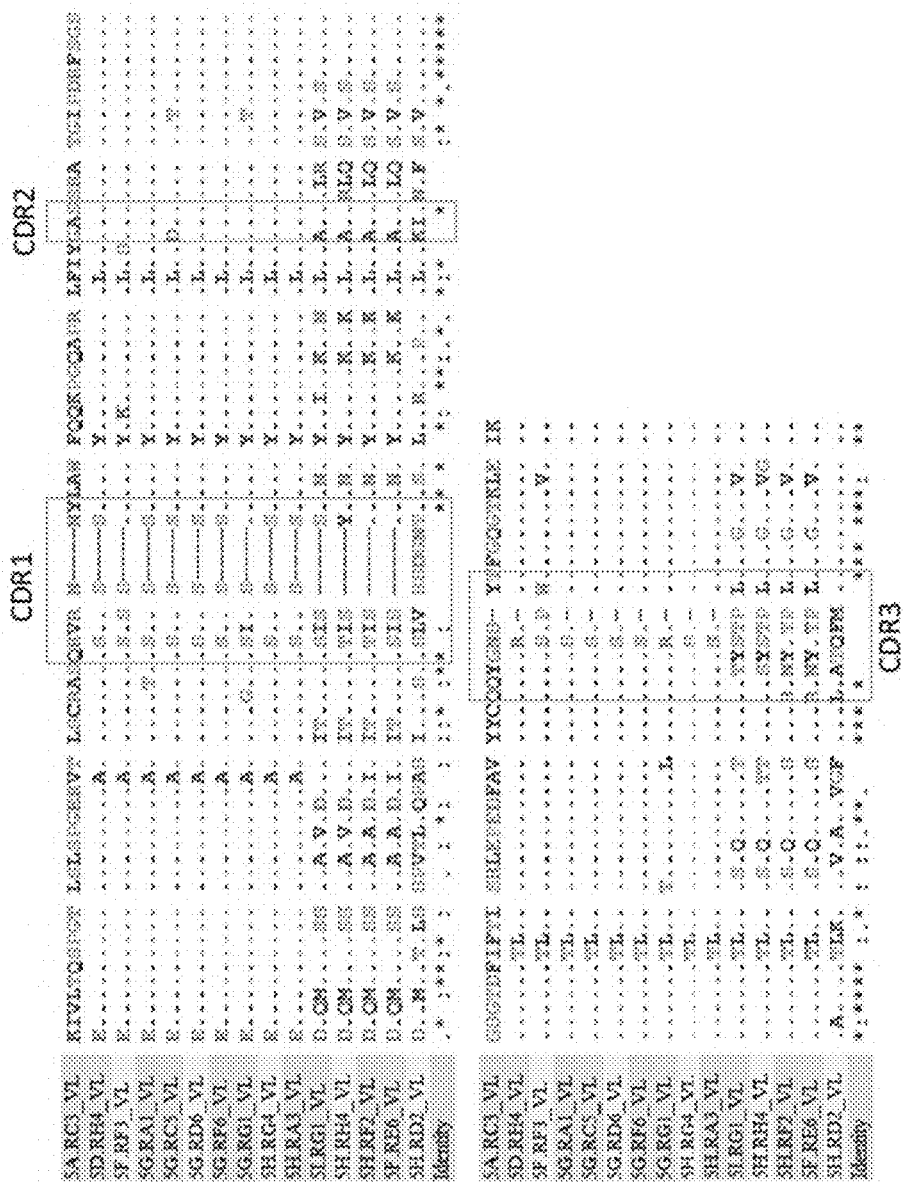

Sequences of the variable light chains of purified mAbs to human PAR4 are shown in FIG. 21. The complementary determining regions (CDRs) are indicated in the figure according to the IMGT numbering system.

The complementary determining region sequences of the antibodies are shown in Table 6 below.

TABLE 6

Complementarity determining region sequences of purified anti-PAR4 mAbs

| Antibody clone | VH CDR1 | VH CRD2 | VH CDR3 | VL CDR1 | VL CDR2 | VL CDR3 |
|---|---|---|---|---|---|---|
| 5A.RC3 | GFTLSNYG (SEQ ID NO: 13) | IWYDGSNK (SEQ ID NO: 14) | ARESIVEVLPPFDY (SEQ ID NO: 15) | QRVRNNY (SEQ ID NO: 16) | GAS (SEQ ID NO: 17) | QQYGNSYT (SEQ ID NO: 18) |
| 5I.RG1 | SGSFSTYF (SEQ ID NO: 47) | IIHTGST (SEQ ID NO: 48) | AFEYSSSGGYYYGMDV (SEQ ID NO: 49) | QSISSY (SEQ ID NO: 50) | AAS (SEQ ID NO: 51) | QQTYSTPLT (SEQ ID NO: 52) |
| 5F.RF3 | AYTFTNYG (SEQ ID NO: 24) | ISPYNGNT (SEQ ID NO: 25) | AREYNRSSRGRYYYYGMDV (SEQ ID NO: 26) | QSVSSNY (SEQ ID NO: 27) | GAS (SEQ ID NO: 28) | QQYGSSPWT (SEQ ID NO: 29) |
| 5G.RA1 | GFTFSSYG (SEQ ID NO: 55) | IWYDGSNK (SEQ ID NO: 14) | ARETALVRGVPFDY (SEQ ID NO: 56) | QSVRSSY (SEQ ID NO: 57) | GAS (SEQ ID NO: 28) | QQYGSSYT (SEQ ID NO: 58) |
| 5H.RD2 | GFTFFNTW (SEQ ID NO: 34) | VKSKNDGGTK (SEQ ID NO: 35) | TTDPHYDFWSAY (SEQ ID NO: 36) | QSLVHSDGNT (SEQ ID NO: 37) | KIS (SEQ ID NO: 38) | LQATQFMYT (SEQ ID NO: 39) |
| 5D.RH4 | GFTFSSDG (SEQ ID NO: 59) | IWFDGRNK (SEQ ID NO: 60) | ARESSISTRPPFDY (SEQ ID NO: 61) | QSVRSSY (SEQ ID NO: 57) | GAS (SEQ ID NO: 28) | QQYGRSYT (SEQ ID NO: 62) |
| 5H.RH4 | GGSFSNYY (SEQ ID NO: 63) | INHSGST (SEQ ID NO: 64) | KVEHSSSGHYYYGMDV (SEQ ID NO: 65) | QTISYY (SEQ ID NO: 66) | AAS (SEQ ID NO: 51) | QQSYSTPLT (SEQ ID NO: 67) |
| 5G.RF6 | GFTFSNYG (SEQ ID NO: 68) | IWYDGSNK (SEQ ID NO: 14) | ARETIMVRGVPFD (SEQ ID NO: 69) | QSVRSSY (SEQ ID NO: 57) | GAS (SEQ ID NO: 28) | QQYGSSYT (SEQ ID NO: 58) |
| 5G.RD6 | GFAFSSYG (SEQ ID NO: 70) | IWYDGSNR (SEQ ID NO: 71) | ARETAMVRGVPFDY (SEQ ID NO: 72) | QSVRSSY (SEQ ID NO: 57) | GAS (SEQ ID NO: 28) | QQYGSSYT (SEQ ID NO: 58) |
| 5H.RA3 | GFTFSSYG (SEQ ID NO: 55) | IWYDGTKK (SEQ ID NO: 73) | ARKGARGITGLDY (SEQ ID NO: 74) | QSVRSSY (SEQ ID NO: 57) | GAS (SEQ ID NO: 28) | QQYGSSYT (SEQ ID NO: 58) |
| 5G.RG1 | GFTLSSYG (SEQ ID NO: 75) | IWYDGSSK (SEQ ID NO: 76) | ARETILIGGVPFDY (SEQ ID NO: 77) | QSIRSNY (SEQ ID NO: 78) | GAS (SEQ ID NO: 28) | QQYGRSYT (SEQ ID NO: 62) |
| 5H.RG4 | GYTFTGHY (SEQ ID NO: 79) | INPNSGGT (SEQ ID NO: 80) | ARGYYDTSGYYYAFEF (SEQ ID NO: 81) | QSVRSSY (SEQ ID NO: 57) | GAS (SEQ ID NO: 28) | QQYGSSYT (SEQ ID NO: 58) |
| 5G.RC5 | GYSFIDYY (SEQ ID NO: 82) | INPNSGGT (SEQ ID NO: 80) | ARGHCGGDCYCFFDH (SEQ ID NO: 83) | QSVRSSY (SEQ ID NO: 57) | ASS (SEQ ID NO: 51) | QQYGSSYT (SEQ ID NO: 58) |
| 5F.RE6 | GFTFSSYG (SEQ ID NO: 55) | IWYDGTKK (SEQ ID NO: 73) | ARKGARGITGLDY (SEQ ID NO: 74) | QSISNY (SEQ ID NO: 84) | AAS (SEQ ID NO: 51) | RQNYNTPLT (SEQ ID NO: 85) |
| 5H.RF2 | GGSLSDYY (SEQ ID NO: 86) | INHSGTT (SEQ ID NO: 87) | AIEYSNSRGYYYGMDV (SEQ ID NO: 88) | QTISNY (SEQ ID NO: 109) | AAS (SEQ ID NO: 51) | RQNYNTPLT (SEQ ID NO: 85) |

TABLE 7

VH and VL sequences of purified anti-PAR4 mAbs

| Antibody clone | VH | VL |
|---|---|---|
| 5A.RC3 | QVQLVESGGGVVQPGRSLRLSCAASGFTLSNYGMHWVRQAPGKGLEWVSVIWYDGSNKHYADSVKGRFTISRDNSKNTLYLQMNSLRAEDTAVYYCARESIVEVLPPFDYWGQGTLVTVSS (SEQ ID NO: 11) | KIVLTQSPGTLSLSPGERVTLSCRASQRVRNNYLAWFQQKPGQAPRLFIYGASSRATGIPDRFSGSGSGTDFIFTISRLEPEDFAVYYCQQYGNSYTFGQGTKLEIK (SEQ ID NO: 12) |
| 5I.RG1 | QVQLQQWGAGLLKPSETLSLACAISSGSFSTYFWRWIRQPPGKGLEWIGEIIHTGSTTYNPSLKSRVTISVDTSKNQLSLKLSSVTAADTAVYYCAFEYSSSGGYYYGMDVWGQGTTVTVSS (SEQ ID NO: 45) | DIQMTQSPSSLSASVGDRVTITCRASQSISSYLNWYQQIPGKAPNLLIYAASSLRSGVPSRFSGSGSGTDFTLTISSLQPEDFATYYCQQTYSTPLTFGGGTKVEIK (SEQ ID NO: 46) |
| 5F.RF3 | QVQLVQSGAEVKKPGASVKVSCKTSAYTFTNYGISWVRQAPGQGLEWMGWISPYNGNTNYAQKLQGRVTMTTDTSTRTAYMELRSLRSDDTAVYYCAREYNRSSRGRYYYYGMDVWGQGTTVTVSS (SEQ ID NO: 22) | EIVLTQSPGTLSLSPGERATLSCRASQSVSSNYLAWYQKKPGQAPRLLISGASSRATGIPDRFSGSGSGTDFTLTISRLEPEDFAVYYCQQYGSSPWTFGQGTKVEIK (SEQ ID NO: 23) |
| 5G.RA1 | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARETALVRGVPFDYWGQGTLVTVSS (SEQ ID NO: 53) | EIVLTQSPGTLSLSPGERATLSCRTSQSVRSSYLAWYQQKPGQAPRLLIYGASSRATGIPDRFSGSGSGTDFTLTISRLEPEDFAVYYCQQYGSSYTFGQGTKLEIK (SEQ ID NO: 54) |
| 5H.RD2 | EVQLVESGGDLVKPGGSLRLSCSASGFTFFNTWMNWVRQAPGKGLEWVGRVKSNDGGTKDYAAPVTGRFTISRDDSKDTLYLQMNSLKTEDTAVYYCTTDPHYDFWSAYWGQGTLVTVSS (SEQ ID NO: 32) | DIVMTQTPLSSPVTLGQPASISCRSSQSLVHSDGNTYLSWLQQRPGQPPRLLIYKISNRFSGVPDRFSGSGAGTDFTLKISRVEAEDVGFYYCLQATQFMYTFGQGTKLEIK (SEQ ID NO: 33) |
| 5D.RH4 | QIQLVESGGGVVQPGRSLRLSCAASGFTFSSDGMHWVRQAPGKGLEWVAVIWFDGRNKYYLDSVKGRFTISRDNSKNTLYLQMNSLRAEDTAVYYCARESSISTRPPFDYWGQGTLVTVSS (SEQ ID NO: 89) | EIVLTQSPGTLSLSPGERATLSCRASQSVRSSYLAWYQQKPGQAPRLLIYGASSRATGIPDRFSGSGSGTDFTLTISRLEPEDFAVYYCQQYGRSYTFGQGTKLEIK (SEQ ID NO: 90) |
| 5H.RH4 | QVQLQQWGAGLLKPSETLSLTCAVYGGSFSNYYWSWIHQPPGKGLEWIGEINHSGSTNYNPSLKSRVTISVDTSKKQFSLNLSSVTAADTAVYYCKVEHSSSSGHYYYGMDVWGQGTTVTVSS (SEQ ID NO: 91) | DIQMTQSPSSLSASVGDRVTITCRASQTISYYLNWYQQKPGKAPKLLIYAASRLQSGVPSRFSGSGSGTDFTLTISSLQPEDFTTYYCQQSYSTPLTFGGGTKVGIK (SEQ ID NO: 92) |
| 5G.RF6 | QVQLVESGGGVVQPGRSLRLSCAASGFTFSNYGMHWVRQAPGKGLEWVAVIWYDGSNKYYADSVRGRFTISRDNSKNTQYLQMNSLRAEDTAVYYCARETIMVRGVPFDYWGQGTLVTVSS (SEQ ID NO: 93) | EIVLTQSPGTLSLSPGERATLSCRASQSVRSSYLAWYQQKPGQAPRLLIYGASSRATGIPDRFSGSGSGTDFTLTISRLEPEDFAVYYCQQYGSSFTFGQGTKLEIK (SEQ ID NO: 94) |
| 5G.RD6 | QVQLVESGGGVVQPGRSLRLSCAASGFAFSSYGMHWVRQAPGKGLEWVAVIWYDGSNRYYADSVKGRFTISRDTSKNTLFLQMNSLRAEDTAVYYCARETAMVRGVPFDYWGQGTLVTVSS (SEQ ID NO: 95) | EIVLTQSPGTLSLSPGERATLSCRASQSVRSSYLAWYQQKPGQAPRLLIYGASSRATGIPDRFSGSGSGTDFTLTISRLEPEDFAVYYCQQYGSSYTFGQGTKLEIK (SEQ ID NO: 96) |
| 5H.RA3 | QVQLVESGGGVVQPGRSLRVSCAASGFTFSSYGMLWVRQAPGKGLEWVAVIWYDGTKKYADSLKGRFTISRDNSKYTLYLQMNSLRADDTALYFCARKGARGITGLDYWGQGTLVTVSS (SEQ ID NO: 97) | EIVLTQSPGTLSLSPGERATLSCRASQSVRSSYLAWYQQKPGQAPRLLIYGASSRATGIPDRFSGSGSGTDFTLTISRLEPEDFAVYYCQQYGSSYTFGQGTKLEIK (SEQ ID NO: 98) |
| 5G.RG1 | QVQLVESGGGVVQPGRSLRLSCVASGFTLSSYGMHWVRQAPGKGLEWVAVIWYDGSSKYYTDSVKGRFDISRDNSKNTLYLQMNILRAEDTAVYYCARETILIGGVPFDYWGQGTLVTVSS (SEQ ID NO: 99) | EIVLTQSPGTLSLSPGERATLSCGASQSIRSNYLAWYQQKPGQAPRLLIYGASSRATGTPDRFSGSGSGTDFTLTITRLEPEDFALYYCQQYGRSYTFGQGTKLEIK (SEQ ID NO: 100) |
| 5H.RG4 | QVQLVQSGAEVKKPGASVKVSCKASGYTFTGHYFHWVRQAPGQGLEWMGWINPNSGGTNFAQRFQGRVTMTRVTSISTAYMELSGLRSDDTAVYYCARGYYDTSGYYYAFEFWGQGTLVIVSS (SEQ ID NO: 101) | EIVLTQSPGTLSLSPGERATLSCRASQSVRSSYLAWYQQKPGQAPRLLIYGASSRATGIPDRFSGSGSGTDFTLTISRLEPEDFAVYYCQQYGSSYTFGQGTKLEIK (SEQ ID NO: 102) |
| 5G.RC5 | QVQLVQSGAEVKKPGASVKVSCKASGYSFIDYYMHWVRQAPGQGLEWMGWINPNSGGTNYAQKFQGRVTMTRDTSISTAYMEMRRLRSDDTAVYYCARGHCGGDCYCFFDHWGQGTLVIVSS (SEQ ID NO: 103) | EIVLTQSPGTLSLSPGERATLSCRASQSVRSSYLAWYQQKPGQAPRLLIYDASSRATGTPDRFSGSGSGTDFTLTISRLEPEDFAVYYCQQYGSSYTFGQGTKLEIK (SEQ ID NO: 104) |
| 5F.RE6 | QVQLAESGGGVVQPGRSLRVSCAASGFTFSSYGMHWVRQAPGKGLEWVAVIWYDGTKKYADSLKGRFTISRDNSKYTLYLQMNSLRADDTALYFCARKGARGITGLDYWGQGTLVTVSS (SEQ ID NO: 105) | DIQMTQSPSSLSASAGDRITITCRASQSISNYLNWYQQKPGKAPKLLIYAASSLQSGVPSRFSGSGSGTDFTLTISSLQPEDFASYYCRQNYNTPLTFGGGTKVEIK (SEQ ID NO: 106) |
| 5H.RF2 | QVQLQQWGAGLLKPSETLALTCAVYGGSLSDYYWSWIRQPPGKGLEWIGEINHSGTTNYNPSLKSRVTISVDTSKKQFSLKLSSVTAADTAVYYCAIEYSNSRGYYYGMDVWGQGTTVTVSS (SEQ ID NO: 107) | DIQMTQSPSSLSASAGDRITITCRASQTISNYLNWYQQKPGKAPKLLIYAASSLQSGVPSRFSGSGSGTDFTLTISSLQPEDFASYYCRQNYNTPLTFGGGTKVEIK (SEQ ID NO: 108) |

Example 17 Epitope Mapping

To determine the minimal epitope to which the anti-hPAR4 monoclonal antibodies bind, three overlapping peptides corresponding to the hPAR4 immunising peptide were synthesised as shown below and in FIG. 22(SEQ ID NO:4; 119, 120, and 121, respectively).

```
G D D S T P S I L P A P R G Y P G Q V    hPAR4
                                         peptide
G D D S T P S I L                        hPAR4 1-9
          I L P A P R G                  hPAR4 8-15
                  A P R G Y P G Q V      hPAR4 11-20
```

The sequence of the thrombin cleavage site RG is underlined. The C-terminal Cysteine residue was removed to prevent formation of multimers, refer to Table 2 for original hPAR4 peptide (KLH and naked peptides).

Screening was performed using a ELISA assay as described in Example 11 to identify if the mAbs showed greater reactivity to any of the shorter overlapping peptides spanning the original peptide antigen. Briefly the peptides were coated onto a Nunc maxisorp ELISA plate at 10 ug/ml overnight in coating buffer (0.1 M sodium carbonate pH8.0). Purified mAbs diluted in PBS were used in place of supernatant.

Figure 23:
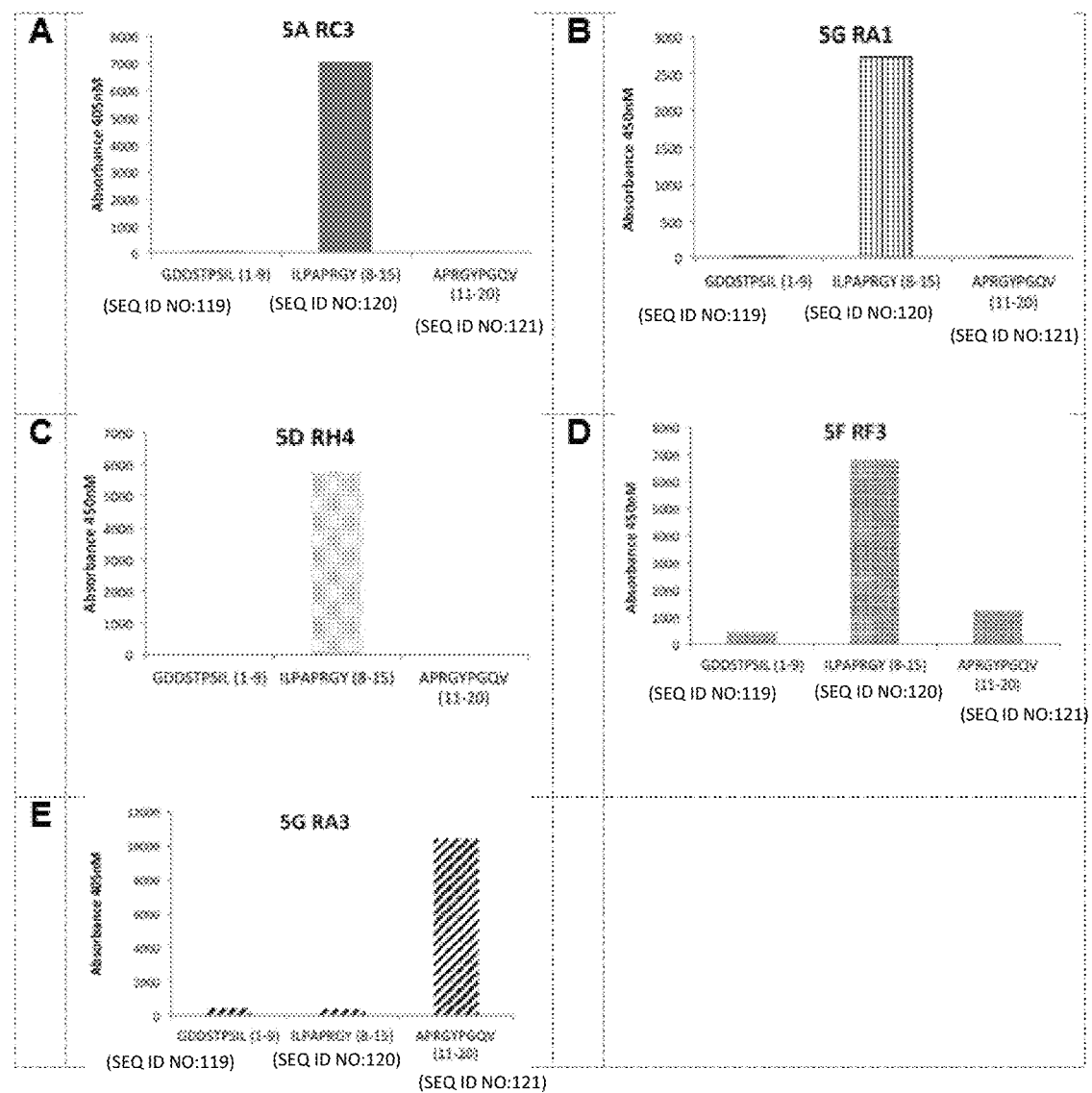
FIG. 23 shows reactivity of purified hPAR4 mAbs with peptide 1-9, peptide 8-15 and peptide 11-20. Absorbance values were subtracted from background levels and a non-hPAR4 control mAb did not react with any of the three peptides.

As shown in FIG. 23 purified mAbs 5A.RC3, 5G.RA1, 5D.RH4 and 5F.RF3 predominantly reacted with the core peptide amino acid residues 8-15, which contains the thrombin cleavage site, therefore indicating the epitope is within this region of the original hPAR4 peptide.

As shown in FIG. 23, purified mAb 5G.RA3 reacted with the peptide amino acid residues 11-20 this also contains the thrombin cleavage site however this indicates 5G.RA3 recognises a slightly different epitope of hPAR4 compared to the other mAbs.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

---

The invention claimed is:

1. A protease activated receptor 4 (PAR4) binding protein which is an anti-PAR4 recombinant or synthetic or monoclonal antibody or antigen-binding fragment thereof, wherein the protein specifically binds to an epitope which spans the thrombin cleavage site of PAR4 and comprises:
   (i) a variable heavy chain (VH) having a CDR1, CDR2 and CDR3 sequence comprising respectively SEQ ID NO:13, SEQ ID NO:14 and SEQ ID NO:15, and a variable light chain (VL) having a CDR1, CDR2 and CDR3 sequence comprising respectively SEQ ID NO:16, SEQ ID NO:17 and SEQ ID NO:18; or
   (ii) a VH having CDR1, CDR2 and CDR3 sequence comprising respectively SEQ ID NO:24, SEQ ID NO:25 and SEQ ID NO:26, and a VL having a CDR1, CDR2 and CDR3 sequence comprising respectively SEQ ID NO:27, SEQ ID NO:28 and SEQ ID NO:29.

2. The PAR4-binding protein according to claim 1, wherein the epitope comprises a sequence selected from (i) APRGY (SEQ ID NO:42); (ii) ILPAPRGY (SEQ ID NO:43); or (iii) APRGYPGQV (SEQ ID NO:44); and wherein the thrombin cleavage site corresponds to RG.

3. The PAR4-binding protein according to claim 1, comprising
   a VH sequence which is at least 95% identical to the sequence set forth in SEQ ID NO:11 or a humanized, chimeric or deimmunized version thereof, and a VL sequence which is at least 95% identical to the sequence set forth in SEQ ID NO: 12 or a humanized, chimeric or deimmunized version thereof;
   wherein the binding protein inhibits cleavage of cell surface expressed human PAR4 by equal to or greater than 50% in the presence of thrombin.

4. The PAR4-binding protein according to claim 1, comprising a VH set forth in SEQ ID NO:11 and a VL set forth in SEQ ID NO:12.

5. The PAR4-binding protein according to claim 1, which is an antigen-binding fragment selected from:
   (i) a single chain Fv fragment (scFv);
   (ii) a dimeric scFv (di-scFv); and
   (iii) at least one of (i) and/or (ii) linked to a heavy chain constant region or an Fc or a heavy chain constant domain (CH) 2 and/or CH3.

6. The PAR4-binding protein according to claim 1 which is conjugated to a moiety.

7. The PAR4-binding protein according to claim 6, wherein the moiety is selected from the group consisting of a radioisotope, a detectable label, a therapeutic compound, a colloid, a toxin, a nucleic acid, a peptide, a protein, a compound that increases the half-life of the PAR4-binding protein in a subject and mixtures thereof.

8. A nucleic acid encoding the PAR4-binding protein according to claim 1.

9. A nucleic acid sequence encoding:
   (i) a PAR4-binding protein comprising a VH sequence set forth in SEQ ID NO:20 and a VL sequence set forth in SEQ ID NO:21; or
   (ii) a PAR4-binding protein comprising a VH sequence set forth in SEQ ID NO:30 and a VL sequence set forth in SEQ ID NO:31.

10. A composition comprising the PAR4-binding protein according to claim 1 and a suitable carrier.

11. A method for treating a thrombosis or a thromboembolic disorder in a subject, the method comprising administering the PAR4-binding protein or the antibody according to claim 1.

12. A method of treating, or ameliorating thrombosis or a thromboembolic disorder comprising administering to a subject in need thereof a therapeutically effective amount of the PAR4-binding protein or the antibody according to claim 1.

13. The PAR4-binding protein according to claim 3, wherein:
   (i) the VH sequence is at least 97% identical to SEQ ID NO:11, and the VL sequence is at least 97% identical to SEQ ID NO:12; or
   (ii) the VH sequence is at least 97% identical to SEQ ID NO:22, and the VL sequence is at least 97% identical to SEQ ID NO:23.

14. The PAR4-binding protein according to claim 3, wherein the binding protein inhibits cleavage of cell surface expressed human PAR4 by equal to or greater than 90% in the presence of thrombin.

15. The PAR4-binding protein according to claim 1, wherein the PAR4-binding protein comprises a variable heavy chain (VH) having a CDR1, CDR2 and CDR3 sequence comprising respectively SEQ ID NO:13, SEQ ID NO:14 and SEQ ID NO:15, and a variable light chain (VL) having a CDR1, CDR2 and CDR3 sequence comprising respectively SEQ ID NO:16, SEQ ID NO:17 and SEQ ID NO:18.

16. The PAR4-binding protein according to claim 1, wherein the PAR4-binding protein comprises a VH having CDR1, CDR2 and CDR3 sequence comprising respectively SEQ ID NO:24, SEQ ID NO:25 and SEQ ID NO:26, and a VL having a CDR1, CDR2 and CDR3 sequence comprising respectively SEQ ID NO:27, SEQ ID NO:28 and SEQ ID NO:29.

17. The PAR4-binding protein according to claim 1, comprising
- a VH sequence which is at least 95% identical to the sequence set forth in SEQ ID NO:22 or a humanized, chimeric or deimmunized version thereof, and a VL sequence which is at least 95% identical to the sequence set forth in or SEQ ID NO:23 or a humanized, chimeric or deimmunized version thereof;

wherein the binding protein inhibits cleavage of cell surface expressed human PAR4 by equal to or greater than 50% in the presence of thrombin.

18. The PAR4-binding protein according to claim 1, comprising a VH set forth in SEQ ID NO:22 and a VL set forth in SEQ ID NO:23.

19. A method for treating a thrombosis or a thromboembolic disorder in a subject, the method comprising administering the PAR4-binding protein or the antibody according to claim 15.

20. A method of treating, or ameliorating thrombosis or a thromboembolic disorder comprising administering to a subject in need thereof a therapeutically effective amount of the PAR4-binding protein or the antibody according to claim 15.

* * * * *

SEQUENCE LISTING

```
<160> NUMBER OF SEQ ID NOS: 121

<210> SEQ ID NO 1
<211> LENGTH: 6
<212> TYPE: PRT
<213> ORGANISM: Homo sapiens

<400> SEQUENCE: 1

Pro Arg Gly Tyr Pro Gly
1               5

<210> SEQ ID NO 2
<211> LENGTH: 20
<212> TYPE: PRT
<213> ORGANISM: Homo sapiens

<400> SEQUENCE: 2

Gly Asp Asp Ser Thr Pro Ser Ile Leu Pro Ala Pro Arg Gly Tyr Pro
1               5                   10                  15

Gly Gln Val Cys
            20

<210> SEQ ID NO 3
<211> LENGTH: 20
<212> TYPE: PRT
<213> ORGANISM: Mus musculus

<400> SEQUENCE: 3

Leu Lys Glu Pro Lys Ser Ser Asp Lys Pro Asn Pro Arg Gly Tyr Pro
1               5                   10                  15

Gly Lys Phe Cys
            20

<210> SEQ ID NO 4
<211> LENGTH: 20
<212> TYPE: PRT
<213> ORGANISM: Artificial Sequence
<220> FEATURE:
<223> OTHER INFORMATION: sequence of hPAR4 (KLH) used as immunogen
<220> FEATURE:
<221> NAME/KEY: MISC_FEATURE
```

-continued

```
<222> LOCATION: (20)..(20)
<223> OTHER INFORMATION: Amino acid is conjugated to keyhole limpet
      hemocyanin (KLH) peptide

<400> SEQUENCE: 4

Gly Asp Asp Ser Thr Pro Ser Ile Leu Pro Ala Pro Arg Gly Tyr Pro
1               5                  10                  15

Gly Gln Val Cys
            20

<210> SEQ ID NO 5
<211> LENGTH: 20
<212> TYPE: PRT
<213> ORGANISM: Artificial Sequence
<220> FEATURE:
<223> OTHER INFORMATION: sequence of mPAR4 (KLH) used as an immunogen
<220> FEATURE:
<221> NAME/KEY: MISC_FEATURE
<222> LOCATION: (20)..(20)
<223> OTHER INFORMATION: Amino acid is conjugated to keyhole limpet
      hemocyanin (KLH) peptide

<400> SEQUENCE: 5

Leu Lys Glu Pro Lys Ser Ser Asp Lys Pro Asn Pro Arg Gly Tyr Pro
1               5                  10                  15

Gly Lys Phe Cys
            20

<210> SEQ ID NO 6
<211> LENGTH: 24
<212> TYPE: PRT
<213> ORGANISM: Artificial Sequence
<220> FEATURE:
<223> OTHER INFORMATION: sequence of mPAR4 biotin conjugate
<220> FEATURE:
<221> NAME/KEY: MISC_FEATURE
<222> LOCATION: (24)..(24)
<223> OTHER INFORMATION: Amino acid is conjugated to streptavidin-
      k/biotin (SKB) peptide

<400> SEQUENCE: 6

Leu Lys Glu Pro Lys Ser Ser Asp Lys Pro Asn Pro Arg Gly Tyr Pro
1               5                  10                  15

Gly Lys Phe Cys Gly Gly Gly Gly
            20

<210> SEQ ID NO 7
<211> LENGTH: 24
<212> TYPE: PRT
<213> ORGANISM: Artificial Sequence
<220> FEATURE:
<223> OTHER INFORMATION: sequence of hPAR4 biotin conjugate
<220> FEATURE:
<221> NAME/KEY: MISC_FEATURE
<222> LOCATION: (24)..(24)
<223> OTHER INFORMATION: Amino acid is conjugated to streptavidin-
      k/biotin (SKB) peptide

<400> SEQUENCE: 7

Gly Asp Asp Ser Thr Pro Ser Ile Leu Pro Ala Pro Arg Gly Tyr Pro
1               5                  10                  15

Gly Gln Val Cys Gly Gly Gly Gly
            20

<210> SEQ ID NO 8
<211> LENGTH: 22
<212> TYPE: PRT
```

```
<213> ORGANISM: Artificial Sequence
<220> FEATURE:
<223> OTHER INFORMATION: sequence of hPAR3 biotin conjugate
<220> FEATURE:
<221> NAME/KEY: MISC_FEATURE
<222> LOCATION: (22)..(22)
<223> OTHER INFORMATION: Amino acid is conjugated to streptavidin-
      k/biotin (SKB) peptide

<400> SEQUENCE: 8

Ala Lys Pro Thr Leu Pro Ile Lys Thr Phe Arg Gly Ala Pro Pro Asn
1               5                   10                  15

Ser Phe Gly Gly Gly Gly
            20

<210> SEQ ID NO 9
<211> LENGTH: 22
<212> TYPE: PRT
<213> ORGANISM: Artificial Sequence
<220> FEATURE:
<223> OTHER INFORMATION: sequence of hPAR2 biotin conjugate
<220> FEATURE:
<221> NAME/KEY: MISC_FEATURE
<222> LOCATION: (22)..(22)
<223> OTHER INFORMATION: Amino acid is conjugated to streptavidin-
      k/biotin (SKB) peptide

<400> SEQUENCE: 9

Ser Cys Ser Gly Thr Ile Gln Gly Thr Asn Arg Ser Ser Lys Gly Arg
1               5                   10                  15

Ser Leu Gly Gly Gly Gly
            20

<210> SEQ ID NO 10
<211> LENGTH: 22
<212> TYPE: PRT
<213> ORGANISM: Artificial Sequence
<220> FEATURE:
<223> OTHER INFORMATION: sequence of hPAR1 biotin conjugate
<220> FEATURE:
<221> NAME/KEY: MISC_FEATURE
<222> LOCATION: (22)..(22)
<223> OTHER INFORMATION: Amino acid is conjugated to streptavidin-
      k/biotin (SKB) peptide

<400> SEQUENCE: 10

Ser Lys Ala Thr Asn Ala Thr Leu Asp Pro Arg Ser Phe Leu Leu Arg
1               5                   10                  15

Asn Pro Gly Gly Gly Gly
            20

<210> SEQ ID NO 11
<211> LENGTH: 121
<212> TYPE: PRT
<213> ORGANISM: Artificial Sequence
<220> FEATURE:
<223> OTHER INFORMATION: VH of 5A.RC3

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Asn Tyr
            20                  25                  30

Gly Met His Trp Val Arg Gln Ala Pro Gly Lys Gly Leu Glu Trp Val
        35                  40                  45

Ser Val Ile Trp Tyr Asp Gly Ser Asn Lys His Tyr Ala Asp Ser Val
```

```
                        50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Glu Ser Ile Val Glu Val Leu Pro Pro Phe Asp Tyr Trp Gly
            100                 105                 110

Gln Gly Thr Leu Val Thr Val Ser Ser
            115                 120
```

<210> SEQ ID NO 12
<211> LENGTH: 107
<212> TYPE: PRT
<213> ORGANISM: Artificial Sequence
<220> FEATURE:
<223> OTHER INFORMATION: VL of 5A.RC3

<400> SEQUENCE: 12

```
Lys Ile Val Leu Thr Gln Ser Pro Gly Thr Leu Ser Leu Ser Pro Gly
 1               5                  10                  15

Glu Arg Val Thr Leu Ser Cys Arg Ala Ser Gln Arg Val Arg Asn Asn
             20                  25                  30

Tyr Leu Ala Trp Phe Gln Gln Lys Pro Gly Gln Ala Pro Arg Leu Phe
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Ile Phe Thr Ile Ser Arg Leu Glu
 65                  70                  75                  80

Pro Glu Asp Phe Ala Val Tyr Tyr Cys Gln Gln Tyr Gly Asn Ser Tyr
                 85                  90                  95

Thr Phe Gly Gln Gly Thr Lys Leu Glu Ile Lys
            100                 105
```

<210> SEQ ID NO 13
<211> LENGTH: 8
<212> TYPE: PRT
<213> ORGANISM: Artificial Sequence
<220> FEATURE:
<223> OTHER INFORMATION: VH CRD1 of 5A.RC3

<400> SEQUENCE: 13

```
Gly Phe Thr Leu Ser Asn Tyr Gly
 1               5
```

<210> SEQ ID NO 14
<211> LENGTH: 8
<212> TYPE: PRT
<213> ORGANISM: Artificial Sequence
<220> FEATURE:
<223> OTHER INFORMATION: VH CRD2 of 5A.RC3, 5G.RA1, 5G.RF6,

<400> SEQUENCE: 14

```
Ile Trp Tyr Asp Gly Ser Asn Lys
 1               5
```

<210> SEQ ID NO 15
<211> LENGTH: 14
<212> TYPE: PRT
<213> ORGANISM: Artificial Sequence
<220> FEATURE:
<223> OTHER INFORMATION: VH CDR3 of 5A.RC3

```
<400> SEQUENCE: 15

Ala Arg Glu Ser Ile Val Glu Val Leu Pro Pro Phe Asp Tyr
1               5                   10

<210> SEQ ID NO 16
<211> LENGTH: 7
<212> TYPE: PRT
<213> ORGANISM: Artificial Sequence
<220> FEATURE:
<223> OTHER INFORMATION: VL CDR1 of 5A.RC3

<400> SEQUENCE: 16

Gln Arg Val Arg Asn Asn Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: VL CDR2 of 5A.RC3

<400> SEQUENCE: 17

Gly Ala Ser
1

<210> SEQ ID NO 18
<211> LENGTH: 8
<212> TYPE: PRT
<213> ORGANISM: Artificial Sequence
<220> FEATURE:
<223> OTHER INFORMATION: VL CDR3 of 5A.RC3

<400> SEQUENCE: 18

Gln Gln Tyr Gly Asn Ser Tyr Thr
1               5

<210> SEQ ID NO 19
<211> LENGTH: 385
<212> TYPE: PRT
<213> ORGANISM: Homo sapiens

<400> SEQUENCE: 19

Met Trp Gly Arg Leu Leu Leu Trp Pro Leu Val Leu Gly Phe Ser Leu
1               5                   10                  15

Ser Gly Gly Thr Gln Thr Pro Ser Val Tyr Asp Glu Ser Gly Ser Thr
            20                  25                  30

Gly Gly Gly Asp Asp Ser Thr Pro Ser Ile Leu Pro Ala Pro Arg Gly
        35                  40                  45

Tyr Pro Gly Gln Val Cys Ala Asn Asp Ser Asp Thr Leu Glu Leu Pro
    50                  55                  60

Asp Ser Ser Arg Ala Leu Leu Leu Gly Trp Val Pro Thr Arg Leu Val
65                  70                  75                  80

Pro Ala Leu Tyr Gly Leu Val Leu Val Gly Leu Pro Ala Asn Gly
                85                  90                  95

Leu Ala Leu Trp Val Leu Ala Thr Gln Ala Pro Arg Leu Pro Ser Thr
            100                 105                 110

Met Leu Leu Met Asn Leu Ala Ala Ala Asp Leu Leu Leu Ala Leu Ala
        115                 120                 125

Leu Pro Pro Arg Ile Ala Tyr His Leu Arg Gly Gln Arg Trp Pro Phe
    130                 135                 140
```

Gly Glu Ala Ala Cys Arg Leu Ala Thr Ala Ala Leu Tyr Gly His Met
145                 150                 155                 160

Tyr Gly Ser Val Leu Leu Leu Ala Val Ser Leu Asp Arg Tyr Leu
            165                 170                 175

Ala Leu Val His Pro Leu Arg Ala Arg Ala Leu Arg Gly Arg Leu
            180                 185                 190

Ala Leu Gly Leu Cys Met Ala Ala Trp Leu Met Ala Ala Leu Ala
            195                 200                 205

Leu Pro Leu Thr Leu Gln Arg Gln Thr Phe Arg Leu Ala Arg Ser Asp
    210                 215                 220

Arg Val Leu Cys His Asp Ala Leu Pro Leu Asp Ala Gln Ala Ser His
225                 230                 235                 240

Trp Gln Pro Ala Phe Thr Cys Leu Ala Leu Leu Gly Cys Phe Leu Pro
                245                 250                 255

Leu Leu Ala Met Leu Leu Cys Tyr Gly Ala Thr Leu His Thr Leu Ala
                260                 265                 270

Ala Ser Gly Arg Arg Tyr Gly His Ala Leu Arg Leu Thr Ala Val Val
            275                 280                 285

Leu Ala Ser Ala Val Ala Phe Phe Val Pro Ser Asn Leu Leu Leu Leu
    290                 295                 300

Leu His Tyr Ser Asp Pro Ser Pro Ser Ala Trp Gly Asn Leu Tyr Gly
305                 310                 315                 320

Ala Tyr Val Pro Ser Leu Ala Leu Ser Thr Leu Asn Ser Cys Val Asp
                325                 330                 335

Pro Phe Ile Tyr Tyr Tyr Val Ser Ala Glu Phe Arg Asp Lys Val Arg
                340                 345                 350

Ala Gly Leu Phe Gln Arg Ser Pro Gly Asp Thr Val Ala Ser Lys Ala
            355                 360                 365

Ser Ala Glu Gly Gly Ser Arg Gly Met Gly Thr His Ser Ser Leu Leu
            370                 375                 380

Gln
385

<210> SEQ ID NO 20
<211> LENGTH: 363
<212> TYPE: DNA
<213> ORGANISM: Artificial Sequence
<220> FEATURE:
<223> OTHER INFORMATION: VH of 5A.RC3

<400> SEQUENCE: 20
caggtgcagt tggtggagtc ggggggaggc gtggtccagc ctgggaggtc cctgagactc        60
tcctgtgcag cgtctggatt caccctcagt aactatggca tgcactgggt ccgccaggct       120
ccaggcaagg ggctggaatg ggtgtcagtt atctggtatg atggaagtaa taaacactat       180
gcagactccg tgaagggccg attcaccatc tccagacaca attccaagaa cacgctttat       240
ctgcaaatga acagcctgag agccgaggac acggctgtat attattgtgc gagagagagt       300
attgtggagg tgcttcctcc ttttgactat tggggccagg gaaccctggt caccgtctcc       360
tca                                                                     363

<210> SEQ ID NO 21
<211> LENGTH: 348
<212> TYPE: DNA
<213> ORGANISM: Artificial Sequence
<220> FEATURE:
<223> OTHER INFORMATION: VL of 5A.RC3

<400> SEQUENCE: 21

```
aaaattgtgt tgacgcagtc tccaggcacc ctgtctttgt ctccagggga aagagtcacc    60
ctctcctgca gggccagtca gcgtgttagg aacaactact tagcctggtt ccaacagaaa   120
cctggccagg ctcccaggct tttcatctat ggtgcatcca gcagggccac tggcatccca   180
gacaggttca gtggcagtgg gtctgggaca gacttcattt tcaccatcag cagactggag   240
cctgaagatt ttgcagtgta ttactgtcag cagtatggta actcgtacac ttttggccag   300
gggaccaagc tggagatcaa acgggctgat gctgcaccaa ctgtatcc                348
```

<210> SEQ ID NO 22
<211> LENGTH: 126
<212> TYPE: PRT
<213> ORGANISM: Artificial Sequence
<220> FEATURE:
<223> OTHER INFORMATION: VH of 5F.RF3

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Thr Ser Ala Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Leu
    50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Tyr Asn Arg Ser Ser Arg Gly Arg Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 23
<211> LENGTH: 108
<212> TYPE: PRT
<213> ORGANISM: Artificial Sequence
<220> FEATURE:
<223> OTHER INFORMATION: VL of 5F.RF3

<400> SEQUENCE: 23

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Lys Lys Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

```
<210> SEQ ID NO 24
<211> LENGTH: 8
<212> TYPE: PRT
<213> ORGANISM: Artificial Sequence
<220> FEATURE:
<223> OTHER INFORMATION: VH CDR1 of 5F.RF3

<400> SEQUENCE: 24

Ala Tyr Thr Phe Thr Asn Tyr Gly
1               5

<210> SEQ ID NO 25
<211> LENGTH: 8
<212> TYPE: PRT
<213> ORGANISM: Artificial Sequence
<220> FEATURE:
<223> OTHER INFORMATION: VH CDR2 of 5F.RF3

<400> SEQUENCE: 25

Ile Ser Pro Tyr Asn Gly Asn Thr
1               5

<210> SEQ ID NO 26
<211> LENGTH: 19
<212> TYPE: PRT
<213> ORGANISM: Artificial Sequence
<220> FEATURE:
<223> OTHER INFORMATION: VH CDR3 of 5F.RF3

<400> SEQUENCE: 26

Ala Arg Glu Tyr Asn Arg Ser Ser Arg Gly Arg Tyr Tyr Tyr Tyr Gly
1               5                   10                  15

Met Asp Val

<210> SEQ ID NO 27
<211> LENGTH: 7
<212> TYPE: PRT
<213> ORGANISM: Artificial Sequence
<220> FEATURE:
<223> OTHER INFORMATION: VL CDR1 of 5F.RF3

<400> SEQUENCE: 27

Gln Ser Val Ser Ser Asn Tyr
1               5

<210> SEQ ID NO 28
<211> LENGTH: 3
<212> TYPE: PRT
<213> ORGANISM: Artificial Sequence
<220> FEATURE:
<223> OTHER INFORMATION: VL CDR2 of 5F.RF3, 5G.RA1, 5D.RH4, 5G.RF6,
     5G.RD6, 5H.RA3, 5G.RG1, 5H.RG4

<400> SEQUENCE: 28

Gly Ala Ser
1

<210> SEQ ID NO 29
<211> LENGTH: 9
<212> TYPE: PRT
<213> ORGANISM: Artificial Sequence
<220> FEATURE:
<223> OTHER INFORMATION: VL CDR3 of 5F.RF3

<400> SEQUENCE: 29
```

Gln Gln Tyr Gly Ser Ser Pro Trp Thr
1               5

<210> SEQ ID NO 30
<211> LENGTH: 378
<212> TYPE: DNA
<213> ORGANISM: Artificial Sequence
<220> FEATURE:
<223> OTHER INFORMATION: VH of 5F.RF3

<400> SEQUENCE: 30

```
caggttcagc tggtgcagtc tggagctgag gtgaagaagc ctggggcctc agtgaaggtc     60
tcctgcaaga cttctgctta cacctttacc aactatggta tcagctgggt gcgacaggcc    120
cctggacaag gcttgagtg gatgggatgg atcagccctt acaacggcaa cacaaactat     180
gcacagaagt tccagggcag agtcaccatg accacagaca catccacgag acagcgtac    240
atggagctga ggagcctgag atctgacgac acggccgtat attactgtgc gagagagtat    300
aacaggtcgt cgaggggccg ctactactac tacggtatgg acgtctgggg ccaagggacc    360
acggtcaccg tctcctca                                                  378
```

<210> SEQ ID NO 31
<211> LENGTH: 351
<212> TYPE: DNA
<213> ORGANISM: Artificial Sequence
<220> FEATURE:
<223> OTHER INFORMATION: VL of 5F.RF3

<400> SEQUENCE: 31

```
gaaattgtgt tgacgcagtc tccaggcacc ctgtctttgt ctccagggga aagagccacc     60
ctctcctgca gggccagtca gagtgttagt agcaactact tagcctggta ccagaagaaa    120
cctggccagg ctcccaggct cctcatctct ggtgcatcca gcagggccac tggcatccca    180
gacaggttca gcggcagtgg gtctgggaca gacttcactc tcaccatcag tagactggag    240
cctgaagatt ttgcagtgta ttactgtcag cagtatggta gctcaccgtg gacgttcggc    300
caagggacca aggtggaaat caaacgggct gatgctgcac caactgtatc c             351
```

<210> SEQ ID NO 32
<211> LENGTH: 121
<212> TYPE: PRT
<213> ORGANISM: Artificial Sequence
<220> FEATURE:
<223> OTHER INFORMATION: VH of 5H.RD2

<400> SEQUENCE: 32

Glu Val Gln Leu Val Glu Ser Gly Gly Asp Leu Val Lys Pro Gly Gly
1               5                   10                  15

Ser Leu Arg Leu Ser Cys Ser Ala Ser Gly Phe Thr Phe Phe Asn Thr
            20                  25                  30

Trp Met Asn Trp Val Arg Gln Ala Pro Gly Lys Gly Leu Glu Trp Val
        35                  40                  45

Gly Arg Val Lys Ser Lys Asn Asp Gly Gly Thr Lys Asp Tyr Ala Ala
    50                  55                  60

Pro Val Thr Gly Arg Phe Thr Ile Ser Arg Asp Asp Ser Lys Asp Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Pro His Tyr Asp Phe Trp Ser Ala Tyr Trp Gly
            100                 105                 110

```
Gln Gly Thr Leu Val Thr Val Ser Ser
        115                 120

<210> SEQ ID NO 33
<211> LENGTH: 112
<212> TYPE: PRT
<213> ORGANISM: Artificial Sequence
<220> FEATURE:
<223> OTHER INFORMATION: VL of 5H.RD2

<400> SEQUENCE: 33

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Phe Tyr Tyr Cys Leu Gln Ala
                85                  90                  95

Thr Gln Phe Met Tyr Thr Phe Gly Gln Gly Thr Lys Leu Glu Ile Lys
            100                 105                 110

<210> SEQ ID NO 34
<211> LENGTH: 8
<212> TYPE: PRT
<213> ORGANISM: Artificial Sequence
<220> FEATURE:
<223> OTHER INFORMATION: VH CDR1 of 5H.RD2

<400> SEQUENCE: 34

Gly Phe Thr Phe Phe Asn Thr Trp
1               5

<210> SEQ ID NO 35
<211> LENGTH: 10
<212> TYPE: PRT
<213> ORGANISM: Artificial Sequence
<220> FEATURE:
<223> OTHER INFORMATION: VH CDR2 of 5H.RD2

<400> SEQUENCE: 35

Val Lys Ser Lys Asn Asp Gly Gly Thr Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: VH CDR3 of 5H.RD2

<400> SEQUENCE: 36

Thr Thr Asp Pro His Tyr Asp Phe Trp Ser Ala Tyr
1               5                   10

<210> SEQ ID NO 37
<211> LENGTH: 10
<212> TYPE: PRT
<213> ORGANISM: Artificial Sequence
```

```
<220> FEATURE:
<223> OTHER INFORMATION: VL CDR1 of 5H.RD2

<400> SEQUENCE: 37

Gln Ser Leu Val His Ser Asp Gly Asn Thr
1               5                   10

<210> SEQ ID NO 38
<211> LENGTH: 3
<212> TYPE: PRT
<213> ORGANISM: Artificial Sequence
<220> FEATURE:
<223> OTHER INFORMATION: VL CDR2 of 5H.RD2

<400> SEQUENCE: 38

Lys Ile Ser
1

<210> SEQ ID NO 39
<211> LENGTH: 9
<212> TYPE: PRT
<213> ORGANISM: Artificial Sequence
<220> FEATURE:
<223> OTHER INFORMATION: VL CDR3 of 5H.RD2

<400> SEQUENCE: 39

Leu Gln Ala Thr Gln Phe Met Tyr Thr
1               5

<210> SEQ ID NO 40
<211> LENGTH: 363
<212> TYPE: DNA
<213> ORGANISM: Artificial Sequence
<220> FEATURE:
<223> OTHER INFORMATION: VH of 5H.RD2

<400> SEQUENCE: 40
gaggtgcagc tggtggagtc tgggggagac ttggtcaagc ctgggggggtc ccttagactc      60 tcctgttcag cctctggatt cactttcttt aacacctgga tgaactgggt ccgccaggct     120
ccagggaagg gctggagtg gttggccgt gttaaaagca aaatgatgg tgggacaaaa        180 gactacgctg cacccgtgac aggcagattc accatctcaa gagatgattc aaaagacacg     240
ctgtatctgc aaatgaacag cctgaaaacc gaggacacag ccgtgtatta ctgtaccaca     300 gatcccact acgattttg gagtgcctac tggggccagg aaccctggt caccgtctcc        360 tca                                                                   363

<210> SEQ ID NO 41
<211> LENGTH: 363
<212> TYPE: DNA
<213> ORGANISM: Artificial Sequence
<220> FEATURE:
<223> OTHER INFORMATION: VL of 5H.RD2

<400> SEQUENCE: 41
gatattgtga tgacccagac tccactctcc tcacctgtca cccttggaca gccggcctcc      60
atctcctgca ggtctagtca aagcctcgtt cacagtgatg gaaatacccta cttgagttgg    120 cttcagcaga ggccaggcca gcctccaaga ctcctaattt ataagatttc taaccggttc     180
tctggggtcc cagacagatt cagtggcagt ggggcaggga cagattcac actgaaaatc      240 agcagggtgg aggctgagga tgtcgggttt tattactgcc tgcaagctac acaattcatg     300 tacactttg gccaggggac caagctggag atcaaacggg ctgatgctgc accaactgta      360
```

```
tcc                                                                    363
```

<210> SEQ ID NO 42
<211> LENGTH: 5
<212> TYPE: PRT
<213> ORGANISM: Artificial Sequence
<220> FEATURE:
<223> OTHER INFORMATION: epitope PAR4 sequence

<400> SEQUENCE: 42

Ala Pro Arg Gly Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: epitope PAR4 sequence

<400> SEQUENCE: 43

Ile Leu Pro Ala Pro Arg Gly Tyr
1               5

<210> SEQ ID NO 44
<211> LENGTH: 9
<212> TYPE: PRT
<213> ORGANISM: Artificial Sequence
<220> FEATURE:
<223> OTHER INFORMATION: epitope PAR4 sequence

<400> SEQUENCE: 44

Ala Pro Arg Gly Tyr Pro Gly Gln Val
1               5

<210> SEQ ID NO 45
<211> LENGTH: 122
<212> TYPE: PRT
<213> ORGANISM: Artificial Sequence
<220> FEATURE:
<223> OTHER INFORMATION: VH of 5I.RG1

<400> SEQUENCE: 45

Gln Val Gln Leu Gln Gln Trp Gly Ala Gly Leu Leu Lys Pro Ser Glu
1               5                   10                  15

Thr Leu Ser Leu Ala Cys Ala Ile Ser Ser Gly Ser Phe Ser Thr Tyr
                20                  25                  30

Phe Trp Arg Trp Ile Arg Gln Pro Pro Gly Lys Gly Leu Glu Trp Ile
            35                  40                  45

Gly Glu Ile Ile His Thr Gly Ser Thr Thr Tyr Asn Pro Ser Leu Lys
        50                  55                  60

Ser Arg Val Thr Ile Ser Val Asp Thr Ser Lys Asn Gln Leu Ser Leu
65                  70                  75                  80

Lys Leu Ser Ser Val Thr Ala Ala Asp Thr Ala Val Tyr Tyr Cys Ala
                85                  90                  95

Phe Glu Tyr Ser Ser Ser Gly Gly Tyr Tyr Tyr Gly Met Asp Val Trp
            100                 105                 110

Gly Gln Gly Thr Thr Val Thr Val Ser Ser
        115                 120

<210> SEQ ID NO 46
<211> LENGTH: 107

```
<212> TYPE: PRT
<213> ORGANISM: Artificial Sequence
<220> FEATURE:
<223> OTHER INFORMATION: VL of 5I.RG1

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Ile Pro Gly Lys Ala Pro Asn Leu Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Leu
                85                  90                  95

Thr Phe Gly Gly Gly Thr Lys Val Glu Ile Lys
            100                 105

<210> SEQ ID NO 47
<211> LENGTH: 8
<212> TYPE: PRT
<213> ORGANISM: Artificial Sequence
<220> FEATURE:
<223> OTHER INFORMATION: VH CDR1 of 5I.RG1

<400> SEQUENCE: 47

Ser Gly Ser Phe Ser Thr Tyr Phe
1               5

<210> SEQ ID NO 48
<211> LENGTH: 7
<212> TYPE: PRT
<213> ORGANISM: Artificial Sequence
<220> FEATURE:
<223> OTHER INFORMATION: VH CDR2 of 5I.RG1

<400> SEQUENCE: 48

Ile Ile His Thr Gly Ser Thr
1               5

<210> SEQ ID NO 49
<211> LENGTH: 16
<212> TYPE: PRT
<213> ORGANISM: Artificial Sequence
<220> FEATURE:
<223> OTHER INFORMATION: VH CDR3 of 5I.RG1

<400> SEQUENCE: 49

Ala Phe Glu Tyr Ser Ser Ser Gly Gly Tyr Tyr Tyr Gly Met Asp Val
1               5                   10                  15

<210> SEQ ID NO 50
<211> LENGTH: 6
<212> TYPE: PRT
<213> ORGANISM: Artificial Sequence
<220> FEATURE:
<223> OTHER INFORMATION: VL CDR1 of 5I.RG1

<400> SEQUENCE: 50

Gln Ser Ile Ser Ser Tyr
1               5
```

```
<210> SEQ ID NO 51
<211> LENGTH: 3
<212> TYPE: PRT
<213> ORGANISM: Artificial Sequence
<220> FEATURE:
<223> OTHER INFORMATION: VL CDR2 of 5I.RG1, 5H.RH4, 5G.RC5, 5F.RE6,
      5H.RF2

<400> SEQUENCE: 51

Ala Ala Ser
1

<210> SEQ ID NO 52
<211> LENGTH: 9
<212> TYPE: PRT
<213> ORGANISM: Artificial Sequence
<220> FEATURE:
<223> OTHER INFORMATION: VL CDR3 of 5I.RG1

<400> SEQUENCE: 52

Gln Gln Thr Tyr Ser Thr Pro Leu Thr
1               5

<210> SEQ ID NO 53
<211> LENGTH: 121
<212> TYPE: PRT
<213> ORGANISM: Artificial Sequence
<220> FEATURE:
<223> OTHER INFORMATION: VH of 5G.RA1

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Ala Leu Val Arg Gly Val Pro Phe Asp Tyr Trp Gly
            100                 105                 110

Gln Gly Thr Leu Val Thr Val Ser Ser
        115                 120

<210> SEQ ID NO 54
<211> LENGTH: 107
<212> TYPE: PRT
<213> ORGANISM: Artificial Sequence
<220> FEATURE:
<223> OTHER INFORMATION: VL of 5G.RA1

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Thr Ser Gln Ser Val Arg Ser Ser
            20                  25                  30

Tyr Leu Ala Trp Tyr Gln Gln Lys Pro Gly Gln Ala Pro Arg Leu Leu
```

```
                35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Tyr
                85                  90                  95
Thr Phe Gly Gln Gly Thr Lys Leu Glu Ile Lys
            100                 105
```

<210> SEQ ID NO 55
<211> LENGTH: 8
<212> TYPE: PRT
<213> ORGANISM: Artificial Sequence
<220> FEATURE:
<223> OTHER INFORMATION: VH CDR1 of 5G.RA1, 5H.RA3, 5F.RE6

<400> SEQUENCE: 55

```
Gly Phe Thr Phe Ser Ser Tyr Gly
1               5
```

<210> SEQ ID NO 56
<211> LENGTH: 14
<212> TYPE: PRT
<213> ORGANISM: Artificial Sequence
<220> FEATURE:
<223> OTHER INFORMATION: VH CDR3 of 5G.RA1

<400> SEQUENCE: 56

```
Ala Arg Glu Thr Ala Leu Val Arg Gly Val Pro Phe Asp Tyr
1               5                   10
```

<210> SEQ ID NO 57
<211> LENGTH: 7
<212> TYPE: PRT
<213> ORGANISM: Artificial Sequence
<220> FEATURE:
<223> OTHER INFORMATION: VL CDR1 of 5G.RA1, 5D.RH4, 5G.RF6, 5G.RD6,
      5H.RA3, 5H.RG4, 5G.RC5

<400> SEQUENCE: 57

```
Gln Ser Val Arg Ser Ser Tyr
1               5
```

<210> SEQ ID NO 58
<211> LENGTH: 8
<212> TYPE: PRT
<213> ORGANISM: Artificial Sequence
<220> FEATURE:
<223> OTHER INFORMATION: VL CDR3 of 5G.RA1, 5G.RF6, 5G.RD6, 5H.RA3,
      5H.RG4, 5G.RC5

<400> SEQUENCE: 58

```
Gln Gln Tyr Gly Ser Ser Tyr Thr
1               5
```

<210> SEQ ID NO 59
<211> LENGTH: 8
<212> TYPE: PRT
<213> ORGANISM: Artificial Sequence
<220> FEATURE:
<223> OTHER INFORMATION: VH CDR1 of 5D.RH4

<400> SEQUENCE: 59

```
Gly Phe Thr Phe Ser Ser Asp Gly
```

```
<210> SEQ ID NO 60
<211> LENGTH: 8
<212> TYPE: PRT
<213> ORGANISM: Artificial Sequence
<220> FEATURE:
<223> OTHER INFORMATION: VH CDR2 of 5D.RH4

<400> SEQUENCE: 60

Ile Trp Phe Asp Gly Arg Asn Lys
1               5

<210> SEQ ID NO 61
<211> LENGTH: 14
<212> TYPE: PRT
<213> ORGANISM: Artificial Sequence
<220> FEATURE:
<223> OTHER INFORMATION: VH CDR3 of 5D.RH4

<400> SEQUENCE: 61

Ala Arg Glu Ser Ser Ile Ser Thr Arg Pro Pro Phe Asp Tyr
1               5                   10

<210> SEQ ID NO 62
<211> LENGTH: 8
<212> TYPE: PRT
<213> ORGANISM: Artificial Sequence
<220> FEATURE:
<223> OTHER INFORMATION: VL CDR3 of 5D.RH4, 5G.RG1

<400> SEQUENCE: 62

Gln Gln Tyr Gly Arg Ser Tyr Thr
1               5

<210> SEQ ID NO 63
<211> LENGTH: 8
<212> TYPE: PRT
<213> ORGANISM: Artificial Sequence
<220> FEATURE:
<223> OTHER INFORMATION: VH CDR1 of 5H.RH4

<400> SEQUENCE: 63

Gly Gly Ser Phe Ser Asn Tyr Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: VH CDR2 of 5H.RH4

<400> SEQUENCE: 64

Ile Asn His Ser Gly Ser Thr
1               5

<210> SEQ ID NO 65
<211> LENGTH: 17
<212> TYPE: PRT
<213> ORGANISM: Artificial Sequence
<220> FEATURE:
<223> OTHER INFORMATION: VH CDR3 of 5H.RH4

<400> SEQUENCE: 65

Lys Val Glu His Ser Ser Ser Gly His Tyr Tyr Tyr Gly Met Asp
1               5                   10                  15
```

Val

<210> SEQ ID NO 66
<211> LENGTH: 6
<212> TYPE: PRT
<213> ORGANISM: Artificial Sequence
<220> FEATURE:
<223> OTHER INFORMATION: VL CDR1 of 5H.RH4

<400> SEQUENCE: 66

Gln Thr Ile Ser Tyr Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: VL CDR3 of 5H.RH4

<400> SEQUENCE: 67

Gln Gln Ser Tyr Ser Thr Pro Leu Thr
1               5

<210> SEQ ID NO 68
<211> LENGTH: 8
<212> TYPE: PRT
<213> ORGANISM: Artificial Sequence
<220> FEATURE:
<223> OTHER INFORMATION: VH CDR1 of 5G.RF6

<400> SEQUENCE: 68

Gly Phe Thr Phe Ser Asn Tyr Gly
1               5

<210> SEQ ID NO 69
<211> LENGTH: 13
<212> TYPE: PRT
<213> ORGANISM: Artificial Sequence
<220> FEATURE:
<223> OTHER INFORMATION: VH CDR3 of 5G.RF6

<400> SEQUENCE: 69

Ala Arg Glu Thr Ile Met Val Arg Gly Val Pro Phe Asp
1               5                   10

<210> SEQ ID NO 70
<211> LENGTH: 8
<212> TYPE: PRT
<213> ORGANISM: Artificial Sequence
<220> FEATURE:
<223> OTHER INFORMATION: VH CDR1 of 5G.RD6

<400> SEQUENCE: 70

Gly Phe Ala Phe Ser Ser Tyr Gly
1               5

<210> SEQ ID NO 71
<211> LENGTH: 8
<212> TYPE: PRT
<213> ORGANISM: Artificial Sequence
<220> FEATURE:
<223> OTHER INFORMATION: VH CDR2 of 5G.RD6

<400> SEQUENCE: 71

Ile Trp Tyr Asp Gly Ser Asn Arg

```
<210> SEQ ID NO 72
<211> LENGTH: 14
<212> TYPE: PRT
<213> ORGANISM: Artificial Sequence
<220> FEATURE:
<223> OTHER INFORMATION: VH CDR3 of 5G.RD6

<400> SEQUENCE: 72

Ala Arg Glu Thr Ala Met Val Arg Gly Val Pro Phe Asp Tyr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: VH CDR2 of 5H.RA3, 5F.RE6

<400> SEQUENCE: 73

Ile Trp Tyr Asp Gly Thr Lys Lys
1               5

<210> SEQ ID NO 74
<211> LENGTH: 13
<212> TYPE: PRT
<213> ORGANISM: Artificial Sequence
<220> FEATURE:
<223> OTHER INFORMATION: VH CDR3 of 5H.RA3, 5F.RE6

<400> SEQUENCE: 74

Ala Arg Lys Gly Ala Arg Gly Ile Thr Gly Leu Asp Tyr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: VH CDR1 of 5G.RG1

<400> SEQUENCE: 75

Gly Phe Thr Leu Ser Ser Tyr Gly
1               5

<210> SEQ ID NO 76
<211> LENGTH: 8
<212> TYPE: PRT
<213> ORGANISM: Artificial Sequence
<220> FEATURE:
<223> OTHER INFORMATION: VH CDR2 of 5G.RG1

<400> SEQUENCE: 76

Ile Trp Tyr Asp Gly Ser Ser Lys
1               5

<210> SEQ ID NO 77
<211> LENGTH: 14
<212> TYPE: PRT
<213> ORGANISM: Artificial Sequence
<220> FEATURE:
<223> OTHER INFORMATION: VH CDR3 of 5G.RG1

<400> SEQUENCE: 77

Ala Arg Glu Thr Ile Leu Ile Gly Gly Val Pro Phe Asp Tyr
1               5                   10
```

<210> SEQ ID NO 78
<211> LENGTH: 7
<212> TYPE: PRT
<213> ORGANISM: Artificial Sequence
<220> FEATURE:
<223> OTHER INFORMATION: VL CDR1 of 5G.RG1

<400> SEQUENCE: 78

Gln Ser Ile Arg Ser Asn Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: VH CDR1 of 5H.RG4

<400> SEQUENCE: 79

Gly Tyr Thr Phe Thr Gly His Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: VH CDR2 of 5H.RG4, 5G.RC5

<400> SEQUENCE: 80

Ile Asn Pro Asn Ser Gly Gly Thr
1               5

<210> SEQ ID NO 81
<211> LENGTH: 16
<212> TYPE: PRT
<213> ORGANISM: Artificial Sequence
<220> FEATURE:
<223> OTHER INFORMATION: VH CDR3 of 5H.RG4

<400> SEQUENCE: 81

Ala Arg Gly Tyr Tyr Asp Thr Ser Gly Tyr Tyr Ala Phe Glu Phe
1               5                   10                  15

<210> SEQ ID NO 82
<211> LENGTH: 8
<212> TYPE: PRT
<213> ORGANISM: Artificial Sequence
<220> FEATURE:
<223> OTHER INFORMATION: VH CDR1 of 5G.RC5

<400> SEQUENCE: 82

Gly Tyr Ser Phe Ile Asp Tyr Tyr
1               5

<210> SEQ ID NO 83
<211> LENGTH: 15
<212> TYPE: PRT
<213> ORGANISM: Artificial Sequence
<220> FEATURE:
<223> OTHER INFORMATION: VH CDR3 of 5G.RC5

<400> SEQUENCE: 83

Ala Arg Gly His Cys Gly Gly Asp Cys Tyr Cys Phe Phe Asp His
1               5                   10                  15

<210> SEQ ID NO 84
<211> LENGTH: 6
<212> TYPE: PRT
<213> ORGANISM: Artificial Sequence
<220> FEATURE:
<223> OTHER INFORMATION: VL CDR1 of 5F.RE6

<400> SEQUENCE: 84

Gln Ser Ile Ser Asn Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: VL CDR3 of 5F.RE6, 5H.RF2

<400> SEQUENCE: 85

Arg Gln Asn Tyr Asn Thr Pro Leu Thr
1               5

<210> SEQ ID NO 86
<211> LENGTH: 8
<212> TYPE: PRT
<213> ORGANISM: Artificial Sequence
<220> FEATURE:
<223> OTHER INFORMATION: VH CDR1 of 5H.RF2

<400> SEQUENCE: 86

Gly Gly Ser Leu Ser Asp Tyr Tyr
1               5

<210> SEQ ID NO 87
<211> LENGTH: 7
<212> TYPE: PRT
<213> ORGANISM: Artificial Sequence
<220> FEATURE:
<223> OTHER INFORMATION: VH CDR2 of 5H.RF2

<400> SEQUENCE: 87

Ile Asn His Ser Gly Thr Thr
1               5

<210> SEQ ID NO 88
<211> LENGTH: 16
<212> TYPE: PRT
<213> ORGANISM: Artificial Sequence
<220> FEATURE:
<223> OTHER INFORMATION: VH CDR3 of 5H.RF2

<400> SEQUENCE: 88

Ala Ile Glu Tyr Ser Asn Ser Arg Gly Tyr Tyr Tyr Gly Met Asp Val
1               5                   10                  15

<210> SEQ ID NO 89
<211> LENGTH: 121
<212> TYPE: PRT
<213> ORGANISM: Artificial Sequence
<220> FEATURE:
<223> OTHER INFORMATION: VH of 5D.RH4

<400> SEQUENCE: 89

Gln Ile Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asp

```
                20                  25                  30
Gly Met His Trp Val Arg Gln Ala Pro Gly Lys Gly Leu Glu Trp Val
            35                  40                  45

Ala Val Ile Trp Phe Asp Gly Arg Asn Lys Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Ser Ile Ser Thr Arg Pro Pro Phe Asp Tyr Trp Gly
            100                 105                 110

Gln Gly Thr Leu Val Thr Val Ser Ser
            115                 120

<210> SEQ ID NO 90
<211> LENGTH: 107
<212> TYPE: PRT
<213> ORGANISM: Artificial Sequence
<220> FEATURE:
<223> OTHER INFORMATION: VL of 5D.RH4

<400> SEQUENCE: 90

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Tyr
                85                  90                  95

Thr Phe Gly Gln Gly Thr Lys Leu Glu Ile Lys
            100                 105

<210> SEQ ID NO 91
<211> LENGTH: 123
<212> TYPE: PRT
<213> ORGANISM: Artificial Sequence
<220> FEATURE:
<223> OTHER INFORMATION: VH of 5H.RH4

<400> SEQUENCE: 91

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asn Tyr
            20                  25                  30

Tyr Trp Ser Trp Ile His Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Lys Gln Phe Ser Leu
65                  70                  75                  80

Asn Leu Ser Ser Val Thr Ala Ala Asp Thr Ala Val Tyr Tyr Cys Lys
                85                  90                  95
```

Val Glu His Ser Ser Ser Gly His Tyr Tyr Gly Met Asp Val
            100                 105                 110

Trp Gly Gln Gly Thr Thr Val Thr Val Ser Ser
        115                 120

<210> SEQ ID NO 92
<211> LENGTH: 107
<212> TYPE: PRT
<213> ORGANISM: Artificial Sequence
<220> FEATURE:
<223> OTHER INFORMATION: VL of 5H.RH4

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Tyr Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Ser Tyr Ser Thr Pro Leu
                85                  90                  95

Thr Phe Gly Gly Gly Thr Lys Val Gly Ile Lys
            100                 105

<210> SEQ ID NO 93
<211> LENGTH: 121
<212> TYPE: PRT
<213> ORGANISM: Artificial Sequence
<220> FEATURE:
<223> OTHER INFORMATION: VH of 5G.RF6

<400> SEQUENCE: 93

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Arg Gly Arg Phe Thr Ile Ser Arg Asp Asn Ser Lys Asn Thr Gln Tyr
65                  70                  75                  80

Leu Gln Met Asn Ser Leu Arg Ala Glu Asp Thr Ala Val Tyr Tyr Cys
                85                  90                  95

Ala Arg Glu Thr Ile Met Val Arg Gly Val Pro Phe Asp Tyr Trp Gly
            100                 105                 110

Gln Gly Thr Leu Val Thr Val Ser Ser
        115                 120

<210> SEQ ID NO 94
<211> LENGTH: 107
<212> TYPE: PRT
<213> ORGANISM: Artificial Sequence
<220> FEATURE:
<223> OTHER INFORMATION: VL of 5G.RF6

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 95
<211> LENGTH: 121
<212> TYPE: PRT
<213> ORGANISM: Artificial Sequence
<220> FEATURE:
<223> OTHER INFORMATION: VH of 5G.RD6

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Thr Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Thr Ala Met Val Arg Gly Val Pro Phe Asp Tyr Trp Gly
            100                 105                 110

Gln Gly Thr Leu Val Thr Val Ser Ser
        115                 120

<210> SEQ ID NO 96
<211> LENGTH: 107
<212> TYPE: PRT
<213> ORGANISM: Artificial Sequence
<220> FEATURE:
<223> OTHER INFORMATION: VL of 5G.RD6

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 97
<211> LENGTH: 120
<212> TYPE: PRT
<213> ORGANISM: Artificial Sequence
<220> FEATURE:
<223> OTHER INFORMATION: VH of 5H.RA3

<400> SEQUENCE: 97

Gln Val Gln Leu Val Glu Ser Gly Gly Val Val Gln Pro Gly Arg
1               5                   10                  15

Ser Leu Arg Val Ser Cys Ala Ala Ser Gly Phe Thr Phe Ser Ser Tyr
                20                  25                  30

Gly Met Leu Trp Val Arg Gln Ala Pro Gly Lys Gly Leu Glu Trp Val
            35                  40                  45

Ala Val Ile Trp Tyr Asp Gly Thr Lys Lys Tyr Tyr Ala Asp Ser Leu
        50                  55                  60

Lys Gly Arg Phe Thr Ile Ser Arg Asp Asn Ser Lys Tyr Thr Leu Tyr
65                  70                  75                  80

Leu Gln Met Asn Ser Leu Arg Ala Asp Asp Thr Ala Leu Tyr Phe Cys
                85                  90                  95

Ala Arg Lys Gly Ala Arg Gly Ile Thr Gly Leu Asp Tyr Trp Gly Gln
            100                 105                 110

Gly Thr Leu Val Thr Val Ser Ser
        115                 120

<210> SEQ ID NO 98
<211> LENGTH: 107
<212> TYPE: PRT
<213> ORGANISM: Artificial Sequence
<220> FEATURE:
<223> OTHER INFORMATION: VL of 5H.RA3

<400> SEQUENCE: 98

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 99
<211> LENGTH: 121
<212> TYPE: PRT
<213> ORGANISM: Artificial Sequence

```
<220> FEATURE:
<223> OTHER INFORMATION: VH of 5G.RG1

<400> SEQUENCE: 99

Gln Val Gln Leu Val Glu Ser Gly Gly Val Val Gln Pro Gly Arg
1               5                   10                  15

Ser Leu Arg Leu Ser Cys Val Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Lys Tyr Tyr Thr Asp Ser Val
    50                  55                  60

Lys Gly Arg Phe Asp Ile Ser Arg Asp Asn Ser Lys Asn Thr Leu Tyr
65                  70                  75                  80

Leu Gln Met Asn Ile Leu Arg Ala Glu Asp Thr Ala Val Tyr Tyr Cys
                85                  90                  95

Ala Arg Glu Thr Ile Leu Ile Gly Gly Val Pro Phe Asp Tyr Trp Gly
            100                 105                 110

Gln Gly Thr Leu Val Thr Val Ser Ser
        115                 120

<210> SEQ ID NO 100
<211> LENGTH: 107
<212> TYPE: PRT
<213> ORGANISM: Artificial Sequence
<220> FEATURE:
<223> OTHER INFORMATION: VL of 5G.RG1

<400> SEQUENCE: 100

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Gln Ser Ile Arg Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Thr Pro Asp Arg Phe Ser
    50                  55                  60

Gly Ser Gly Ser Gly Thr Asp Phe Thr Leu Thr Ile Thr Arg Leu Glu
65                  70                  75                  80

Pro Glu Asp Phe Ala Leu Tyr Tyr Cys Gln Gln Tyr Gly Arg Ser Tyr
                85                  90                  95

Thr Phe Gly Gln Gly Thr Lys Leu Glu Ile Lys
            100                 105

<210> SEQ ID NO 101
<211> LENGTH: 123
<212> TYPE: PRT
<213> ORGANISM: Artificial Sequence
<220> FEATURE:
<223> OTHER INFORMATION: VH of 5H.RG4

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
            20                  25                  30

Tyr Phe His Trp Val Arg Gln Ala Pro Gly Gln Gly Leu Glu Trp Met
        35                  40                  45
```

```
Gly Trp Ile Asn Pro Asn Ser Gly Gly Thr Asn Phe Ala Gln Arg Phe
    50                  55                  60

Gln Gly Arg Val Thr Met Thr Arg Val Thr Ser Ile Ser Thr Ala Tyr
65                  70                  75                  80

Met Glu Leu Ser Gly Leu Arg Ser Asp Asp Thr Ala Val Tyr Tyr Cys
                85                  90                  95

Ala Arg Gly Tyr Tyr Asp Thr Ser Gly Tyr Tyr Tyr Ala Phe Glu Phe
                100                 105                 110

Trp Gly Gln Gly Thr Leu Val Ile Val Ser Ser
            115                 120
```

<210> SEQ ID NO 102
<211> LENGTH: 107
<212> TYPE: PRT
<213> ORGANISM: Artificial Sequence
<220> FEATURE:
<223> OTHER INFORMATION: VL of 5H.RG4

<400> SEQUENCE: 102

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
                100                 105
```

<210> SEQ ID NO 103
<211> LENGTH: 122
<212> TYPE: PRT
<213> ORGANISM: Artificial Sequence
<220> FEATURE:
<223> OTHER INFORMATION: VH of 5G.RC5

<400> SEQUENCE: 103

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ile Asp Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Met Arg Arg Leu Arg Ser Asp Asp Thr Ala Val Tyr Tyr Cys
                85                  90                  95

Ala Arg Gly His Cys Gly Gly Asp Cys Tyr Cys Phe Phe Asp His Trp
                100                 105                 110

Gly Gln Gly Thr Leu Val Ile Val Ser Ser
            115                 120
```

<210> SEQ ID NO 104
<211> LENGTH: 107
<212> TYPE: PRT
<213> ORGANISM: Artificial Sequence
<220> FEATURE:
<223> OTHER INFORMATION: VL of 5G.RC5

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Thr Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105

<210> SEQ ID NO 105
<211> LENGTH: 120
<212> TYPE: PRT
<213> ORGANISM: Artificial Sequence
<220> FEATURE:
<223> OTHER INFORMATION: VH of 5F.RE6

<400> SEQUENCE: 105

Gln Val Gln Leu Ala Glu Ser Gly Gly Gly Val Val Gln Pro Gly Arg
1               5                   10                  15

Ser Leu Arg Val Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Lys Lys Tyr Tyr Ala Asp Ser Leu
50                  55                  60

Lys Gly Arg Phe Thr Ile Ser Arg Asp Asn Ser Lys Tyr Thr Leu Tyr
65                  70                  75                  80

Leu Gln Met Asn Ser Leu Arg Ala Asp Asp Thr Ala Leu Tyr Phe Cys
                85                  90                  95

Ala Arg Lys Gly Ala Arg Gly Ile Thr Gly Leu Asp Tyr Trp Gly Gln
            100                 105                 110

Gly Thr Leu Val Thr Val Ser Ser
        115                 120

<210> SEQ ID NO 106
<211> LENGTH: 107
<212> TYPE: PRT
<213> ORGANISM: Artificial Sequence
<220> FEATURE:
<223> OTHER INFORMATION: VL of 5F.RE6

<400> SEQUENCE: 106

Asp Ile Gln Met Thr Gln Ser Pro Ser Ser Leu Ser Ala Ser Ala Gly
1               5                   10                  15

```
Asp Arg Ile Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Arg Gln Asn Tyr Asn Thr Pro Leu
                85                  90                  95

Thr Phe Gly Gly Gly Thr Lys Val Glu Ile Lys
            100                 105

<210> SEQ ID NO 107
<211> LENGTH: 122
<212> TYPE: PRT
<213> ORGANISM: Artificial Sequence
<220> FEATURE:
<223> OTHER INFORMATION: VH of 5H.RF2

<400> SEQUENCE: 107

Gln Val Gln Leu Gln Gln Trp Gly Ala Gly Leu Leu Lys Pro Ser Glu
1               5                   10                  15

Thr Leu Ala Leu Thr Cys Ala Val Tyr Gly Gly Ser Leu Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Thr Thr Asn Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Ile Glu Tyr Ser Asn Ser Arg Gly Tyr Tyr Tyr Gly Met Asp Val Trp
            100                 105                 110

Gly Gln Gly Thr Thr Val Thr Val Ser Ser
        115                 120

<210> SEQ ID NO 108
<211> LENGTH: 107
<212> TYPE: PRT
<213> ORGANISM: Artificial Sequence
<220> FEATURE:
<223> OTHER INFORMATION: VL of 5H.RF2

<400> SEQUENCE: 108

Asp Ile Gln Met Thr Gln Ser Pro Ser Ser Leu Ser Ala Ser Ala Gly
1               5                   10                  15

Asp Arg Ile Thr Ile Thr Cys Arg Ala Ser Gln Thr Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Arg Gln Asn Tyr Asn Thr Pro Leu
                85                  90                  95
```

```
Thr Phe Gly Gly Gly Thr Lys Val Glu Ile Lys
            100                 105

<210> SEQ ID NO 109
<211> LENGTH: 6
<212> TYPE: PRT
<213> ORGANISM: Artificial Sequence
<220> FEATURE:
<223> OTHER INFORMATION: VL CDR1 of 5H.RF2

<400> SEQUENCE: 109

Gln Thr Ile Ser Asn Tyr
1               5

<210> SEQ ID NO 110
<211> LENGTH: 121
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (2)..(2)
<223> OTHER INFORMATION: V or I
<220> FEATURE:
<221> NAME/KEY: X
<222> LOCATION: (23)..(23)
<223> OTHER INFORMATION: A or V
<220> FEATURE:
<221> NAME/KEY: X
<222> LOCATION: (28)..(28)
<223> OTHER INFORMATION: T or A
<220> FEATURE:
<221> NAME/KEY: X
<222> LOCATION: (29)..(29)
<223> OTHER INFORMATION: L or F
<220> FEATURE:
<221> NAME/KEY: X
<222> LOCATION: (31)..(31)
<223> OTHER INFORMATION: N or S
<220> FEATURE:
<221> NAME/KEY: X
<222> LOCATION: (32)..(32)
<223> OTHER INFORMATION: Y or D
<220> FEATURE:
<221> NAME/KEY: X
<222> LOCATION: (49)..(49)
<223> OTHER INFORMATION: S or A
<220> FEATURE:
<221> NAME/KEY: X
<222> LOCATION: (53)..(53)
<223> OTHER INFORMATION: Y or F
<220> FEATURE:
<221> NAME/KEY: X
<222> LOCATION: (56)..(56)
<223> OTHER INFORMATION: S or R
<220> FEATURE:
<221> NAME/KEY: X
<222> LOCATION: (57)..(57)
<223> OTHER INFORMATION: S or A
<220> FEATURE:
<221> NAME/KEY: X
<222> LOCATION: (58)..(58)
<223> OTHER INFORMATION: K or R
<220> FEATURE:
<221> NAME/KEY: X
<222> LOCATION: (59)..(59)
<223> OTHER INFORMATION: H or Y
<220> FEATURE:
<221> NAME/KEY: X
<222> LOCATION: (61)..(61)
<223> OTHER INFORMATION: A, L or T
<220> FEATURE:
<221> NAME/KEY: X
<222> LOCATION: (65)..(65)
```

```
<223> OTHER INFORMATION: K or R
<220> FEATURE:
<221> NAME/KEY: X
<222> LOCATION: (69)..(69)
<223> OTHER INFORMATION: T or D
<220> FEATURE:
<221> NAME/KEY: X
<222> LOCATION: (74)..(74)
<223> OTHER INFORMATION: N or T
<220> FEATURE:
<221> NAME/KEY: X
<222> LOCATION: (79)..(79)
<223> OTHER INFORMATION: L or Q
<220> FEATURE:
<221> NAME/KEY: X
<222> LOCATION: (80)..(80)
<223> OTHER INFORMATION: Y or F
<220> FEATURE:
<221> NAME/KEY: X
<222> LOCATION: (85)..(85)
<223> OTHER INFORMATION: S or I
<220> FEATURE:
<221> NAME/KEY: X
<222> LOCATION: (100)..(100)
<223> OTHER INFORMATION: S or T
<220> FEATURE:
<221> NAME/KEY: X
<222> LOCATION: (101)..(101)
<223> OTHER INFORMATION: I, S, or A
<220> FEATURE:
<221> NAME/KEY: X
<222> LOCATION: (102)..(102)
<223> OTHER INFORMATION: V, I, M, or L
<220> FEATURE:
<221> NAME/KEY: X
<222> LOCATION: (103)..(103)
<223> OTHER INFORMATION: E, S, V, or I
<220> FEATURE:
<221> NAME/KEY: X
<222> LOCATION: (104)..(104)
<223> OTHER INFORMATION: V, T, R, or G
<220> FEATURE:
<221> NAME/KEY: X
<222> LOCATION: (105)..(105)
<223> OTHER INFORMATION: L, R or G
<220> FEATURE:
<221> NAME/KEY: X
<222> LOCATION: (106)..(106)
<223> OTHER INFORMATION: P or V

<400> SEQUENCE: 110

Gln Xaa Gln Leu Val Glu Ser Gly Gly Val Val Gln Pro Gly Arg
1               5                   10                  15

Ser Leu Arg Leu Ser Cys Xaa Ala Ser Gly Phe Xaa Xaa Ser Xaa Xaa
            20                  25                  30

Gly Met His Trp Val Arg Gln Ala Pro Gly Lys Gly Leu Glu Trp Val
            35                  40                  45

Xaa Val Ile Trp Xaa Asp Gly Xaa Xaa Xaa Xaa Tyr Xaa Asp Ser Val
50                  55                  60

Xaa Gly Arg Phe Xaa Ile Ser Arg Asp Xaa Ser Lys Asn Thr Xaa Xaa
65                  70                  75                  80

Leu Gln Met Asn Xaa Leu Arg Ala Glu Asp Thr Ala Val Tyr Tyr Cys
                85                  90                  95

Ala Arg Glu Xaa Xaa Xaa Xaa Xaa Xaa Pro Phe Asp Tyr Trp Gly
            100                 105                 110

Gln Gly Thr Leu Val Thr Val Ser Ser
            115                 120

<210> SEQ ID NO 111
<211> LENGTH: 107
```

```
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (1)..(1)
<223> OTHER INFORMATION: K or E
<220> FEATURE:
<221> NAME/KEY: X
<222> LOCATION: (19)..(19)
<223> OTHER INFORMATION: V or A
<220> FEATURE:
<221> NAME/KEY: X
<222> LOCATION: (24)..(24)
<223> OTHER INFORMATION: R or G
<220> FEATURE:
<221> NAME/KEY: X
<222> LOCATION: (25)..(25)
<223> OTHER INFORMATION: A or T
<220> FEATURE:
<221> NAME/KEY: X
<222> LOCATION: (28)..(28)
<223> OTHER INFORMATION: R or S
<220> FEATURE:
<221> NAME/KEY: X
<222> LOCATION: (29)..(29)
<223> OTHER INFORMATION: V or I
<220> FEATURE:
<221> NAME/KEY: X
<222> LOCATION: (31)..(31)
<223> OTHER INFORMATION: N or S
<220> FEATURE:
<221> NAME/KEY: X
<222> LOCATION: (32)..(32)
<223> OTHER INFORMATION: N or S
<220> FEATURE:
<221> NAME/KEY: X
<222> LOCATION: (37)..(37)
<223> OTHER INFORMATION: N or Y
<220> FEATURE:
<221> NAME/KEY: X
<222> LOCATION: (48)..(48)
<223> OTHER INFORMATION: F or L
<220> FEATURE:
<221> NAME/KEY: X
<222> LOCATION: (59)..(59)
<223> OTHER INFORMATION: I or T
<220> FEATURE:
<221> NAME/KEY: X
<222> LOCATION: (73)..(73)
<223> OTHER INFORMATION: I or T
<220> FEATURE:
<221> NAME/KEY: X
<222> LOCATION: (74)..(74)
<223> OTHER INFORMATION: F or L
<220> FEATURE:
<221> NAME/KEY: X
<222> LOCATION: (77)..(77)
<223> OTHER INFORMATION: S or T
<220> FEATURE:
<221> NAME/KEY: X
<222> LOCATION: (86)..(86)
<223> OTHER INFORMATION: V or L
<220> FEATURE:
<221> NAME/KEY: X
<222> LOCATION: (94)..(94)
<223> OTHER INFORMATION: N, R or S

<400> SEQUENCE: 111

Xaa Ile Val Leu Thr Gln Ser Pro Gly Thr Leu Ser Leu Ser Pro Gly
1               5                   10                  15

Glu Arg Xaa Thr Leu Ser Cys Xaa Xaa Ser Gln Xaa Xaa Arg Xaa Xaa
                20                  25                  30

Tyr Leu Ala Trp Xaa Gln Gln Lys Pro Gly Gln Ala Pro Arg Leu Xaa
            35                  40                  45
```

```
Ile Tyr Gly Ala Ser Ser Arg Ala Thr Gly Xaa Pro Asp Arg Phe Ser
    50                  55                  60

Gly Ser Gly Ser Gly Thr Asp Phe Xaa Xaa Thr Ile Xaa Arg Leu Glu
65                  70                  75                  80

Pro Glu Asp Phe Ala Xaa Tyr Tyr Cys Gln Gln Tyr Gly Xaa Ser Tyr
                85                  90                  95

Thr Phe Gly Gln Gly Thr Lys Leu Glu Ile Lys
            100                 105
```

<210> SEQ ID NO 112
<211> LENGTH: 123
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (19)..(19)
<223> OTHER INFORMATION: A or S
<220> FEATURE:
<221> NAME/KEY: X
<222> LOCATION: (21)..(21)
<223> OTHER INFORMATION: T or A
<220> FEATURE:
<221> NAME/KEY: X
<222> LOCATION: (24)..(24)
<223> OTHER INFORMATION: V or I
<220> FEATURE:
<221> NAME/KEY: X
<222> LOCATION: (25)..(25)
<223> OTHER INFORMATION: Y or S
<220> FEATURE:
<221> NAME/KEY: X
<222> LOCATION: (26)..(26)
<223> OTHER INFORMATION: G or S
<220> FEATURE:
<221> NAME/KEY: X
<222> LOCATION: (29)..(29)
<223> OTHER INFORMATION: L or F
<220> FEATURE:
<221> NAME/KEY: X
<222> LOCATION: (31)..(31)
<223> OTHER INFORMATION: N, D or T
<220> FEATURE:
<221> NAME/KEY: X
<222> LOCATION: (33)..(33)
<223> OTHER INFORMATION: Y or F
<220> FEATURE:
<221> NAME/KEY: X
<222> LOCATION: (35)..(35)
<223> OTHER INFORMATION: S or R
<220> FEATURE:
<221> NAME/KEY: X
<222> LOCATION: (38)..(38)
<223> OTHER INFORMATION: R or H
<220> FEATURE:
<221> NAME/KEY: X
<222> LOCATION: (52)..(52)
<223> OTHER INFORMATION: N or I
<220> FEATURE:
<221> NAME/KEY: X
<222> LOCATION: (54)..(54)
<223> OTHER INFORMATION: S or T
<220> FEATURE:
<221> NAME/KEY: X
<222> LOCATION: (56)..(56)
<223> OTHER INFORMATION: T or S
<220> FEATURE:
<221> NAME/KEY: X
<222> LOCATION: (58)..(58)
<223> OTHER INFORMATION: N or T
<220> FEATURE:
<221> NAME/KEY: X
<222> LOCATION: (76)..(76)

```
<223> OTHER INFORMATION: K or N
<220> FEATURE:
<221> NAME/KEY: X
<222> LOCATION: (78)..(78)
<223> OTHER INFORMATION: F or L
<220> FEATURE:
<221> NAME/KEY: X
<222> LOCATION: (81)..(81)
<223> OTHER INFORMATION: K or N
<220> FEATURE:
<221> NAME/KEY: X
<222> LOCATION: (96)..(96)
<223> OTHER INFORMATION: A or K
<220> FEATURE:
<221> NAME/KEY: X
<222> LOCATION: (97)..(97)
<223> OTHER INFORMATION: I, F or V
<220> FEATURE:
<221> NAME/KEY: X
<222> LOCATION: (99)..(99)
<223> OTHER INFORMATION: Y or H
<220> FEATURE:
<221> NAME/KEY: X
<222> LOCATION: (101)..(101)
<223> OTHER INFORMATION: N or S
<220> FEATURE:
<221> NAME/KEY: X
<222> LOCATION: (103)..(103)
<223> OTHER INFORMATION: R, G, or S
<220> FEATURE:
<221> NAME/KEY: X
<222> LOCATION: (105)..(105)
<223> OTHER INFORMATION: V or H

<400> SEQUENCE: 112

Gln Val Gln Leu Gln Gln Trp Gly Ala Gly Leu Leu Lys Pro Ser Glu
1               5                   10                  15

Thr Leu Xaa Leu Xaa Cys Ala Xaa Xaa Xaa Gly Ser Xaa Ser Xaa Tyr
            20                  25                  30

Xaa Trp Xaa Trp Ile Xaa Gln Pro Pro Gly Lys Gly Leu Glu Trp Ile
        35                  40                  45

Gly Glu Ile Xaa His Xaa Gly Xaa Thr Xaa Tyr Asn Pro Ser Leu Lys
    50                  55                  60

Ser Arg Val Thr Ile Ser Val Asp Thr Ser Lys Xaa Gln Xaa Ser Leu
65                  70                  75                  80

Xaa Leu Ser Ser Val Thr Ala Ala Asp Thr Ala Val Tyr Tyr Cys Xaa
                85                  90                  95

Xaa Glu Xaa Ser Xaa Ser Xaa Gly Xaa Tyr Tyr Tyr Gly Met Asp Val
            100                 105                 110

Trp Gly Gln Gly Thr Thr Val Thr Val Ser Ser
        115                 120

<210> SEQ ID NO 113
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: X
<222> LOCATION: (15)..(15)
<223> OTHER INFORMATION: V or A
<220> FEATURE:
<221> NAME/KEY: X
<222> LOCATION: (19)..(19)
<223> OTHER INFORMATION: V or I
<220> FEATURE:
<221> NAME/KEY: X
<222> LOCATION: (28)..(28)
<223> OTHER INFORMATION: S or T
```

```
<220> FEATURE:
<221> NAME/KEY: X
<222> LOCATION: (31)..(31)
<223> OTHER INFORMATION: S, Y or N
<220> FEATURE:
<221> NAME/KEY: X
<222> LOCATION: (39)..(39)
<223> OTHER INFORMATION: K or I
<220> FEATURE:
<221> NAME/KEY: X
<222> LOCATION: (45)..(45)
<223> OTHER INFORMATION: N or K
<220> FEATURE:
<221> NAME/KEY: X
<222> LOCATION: (53)..(53)
<223> OTHER INFORMATION: R or S
<220> FEATURE:
<221> NAME/KEY: X
<222> LOCATION: (55)..(55)
<223> OTHER INFORMATION: R or Q
<220> FEATURE:
<221> NAME/KEY: X
<222> LOCATION: (84)..(84)
<223> OTHER INFORMATION: T or A
<220> FEATURE:
<221> NAME/KEY: X
<222> LOCATION: (85)..(85)
<223> OTHER INFORMATION: T or S
<220> FEATURE:
<221> NAME/KEY: X
<222> LOCATION: (89)..(89)
<223> OTHER INFORMATION: Q or R
<220> FEATURE:
<221> NAME/KEY: X
<222> LOCATION: (91)..(91)
<223> OTHER INFORMATION: T, S or N
<220> FEATURE:
<221> NAME/KEY: X
<222> LOCATION: (93)..(93)
<223> OTHER INFORMATION: N or S
<220> FEATURE:
<221> NAME/KEY: X
<222> LOCATION: (104)..(104)
<223> OTHER INFORMATION: E or G

<400> SEQUENCE: 113

Asp Ile Gln Met Thr Gln Ser Pro Ser Ser Leu Ser Ala Ser Xaa Gly
1               5                   10                  15

Asp Arg Xaa Thr Ile Thr Cys Arg Ala Ser Gln Xaa Ile Ser Xaa Tyr
            20                  25                  30

Leu Asn Trp Tyr Gln Gln Xaa Pro Gly Lys Ala Pro Xaa Leu Leu Ile
        35                  40                  45

Tyr Ala Ala Ser Xaa Leu Xaa Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Xaa Xaa Tyr Tyr Cys Xaa Gln Xaa Tyr Xaa Thr Pro Leu
                85                  90                  95

Thr Phe Gly Gly Gly Thr Lys Xaa Ile Lys
            100                 105

<210> SEQ ID NO 114
<211> LENGTH: 5
<212> TYPE: PRT
<213> ORGANISM: Artificial sequence
<220> FEATURE:
<223> OTHER INFORMATION: Synthetic peptide

<400> SEQUENCE: 114

Ala Pro Arg Gly Tyr
```

```
<210> SEQ ID NO 115
<211> LENGTH: 18
<212> TYPE: PRT
<213> ORGANISM: Artificial sequence
<220> FEATURE:
<223> OTHER INFORMATION: Synethtic peptide

<400> SEQUENCE: 115

Ser Lys Ala Thr Asn Ala Thr Leu Asp Pro Arg Ser Phe Leu Leu Arg
1               5                   10                  15

Asn Pro

<210> SEQ ID NO 116
<211> LENGTH: 18
<212> TYPE: PRT
<213> ORGANISM: Artificial sequence
<220> FEATURE:
<223> OTHER INFORMATION: Synthetic peptide

<400> SEQUENCE: 116

Ser Cys Ser Gly Thr Ile Gln Gly Thr Asn Arg Ser Ser Lys Gly Arg
1               5                   10                  15

Ser Leu

<210> SEQ ID NO 117
<211> LENGTH: 18
<212> TYPE: PRT
<213> ORGANISM: Artificial sequence
<220> FEATURE:
<223> OTHER INFORMATION: Synthetic peptide

<400> SEQUENCE: 117

Ser Cys Ser Gly Thr Ile Gln Gly Thr Asn Arg Ser Ser Lys Gly Arg
1               5                   10                  15

Ser Leu

<210> SEQ ID NO 118
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: C terminal NH-2

<400> SEQUENCE: 118

Ala Tyr Pro Gly Lys Phe
1               5

<210> SEQ ID NO 119
<211> LENGTH: 9
<212> TYPE: PRT
<213> ORGANISM: Artificial sequence
<220> FEATURE:
<223> OTHER INFORMATION: Synthetic peptide

<400> SEQUENCE: 119

Gly Asp Asp Ser Thr Pro Ser Ile Leu
1               5

<210> SEQ ID NO 120
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 120

Ile Leu Pro Ala Pro Arg Gly Tyr
1               5

<210> SEQ ID NO 121
<211> LENGTH: 9
<212> TYPE: PRT
<213> ORGANISM: Artificial sequence
<220> FEATURE:
<223> OTHER INFORMATION: Synthetic peptide

<400> SEQUENCE: 121

Ala Pro Arg Gly Tyr Pro Gly Gln Val
1               5
```